United States Patent
Ohline et al.

(10) Patent No.: US 8,882,657 B2
(45) Date of Patent: Nov. 11, 2014

(54) INSTRUMENT HAVING RADIO FREQUENCY IDENTIFICATION SYSTEMS AND METHODS FOR USE

(75) Inventors: Robert M. Ohline, Redwood City, CA (US); Katherine Whitin, Redwood City, CA (US); Amir Belson, Sunnyvale, CA (US); Christopher D. Justice, Prairie Village, KS (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1530 days.

(21) Appl. No.: 11/648,408

(22) Filed: Dec. 28, 2006

(65) Prior Publication Data

US 2007/0249901 A1    Oct. 25, 2007

Related U.S. Application Data

(63) Continuation-in-part of application No. 10/384,252, filed on Mar. 7, 2003, now abandoned.

(60) Provisional application No. 60/755,255, filed on Dec. 30, 2005.

(51) Int. Cl.
*A61B 1/005* (2006.01)
*A61B 5/06* (2006.01)
*A61B 1/31* (2006.01)
*A61B 19/00* (2006.01)

(52) U.S. Cl.
CPC ......... *A61B 1/005* (2013.01); *A61B 2019/5251* (2013.01); *A61B 1/31* (2013.01); *A61B 2019/462* (2013.01); *A61B 19/5212* (2013.01); *A61B 19/5244* (2013.01); *A61B 2019/5483* (2013.01); *A61B 2019/547* (2013.01); *A61B 2019/448* (2013.01); *A61B 5/064* (2013.01)
USPC ......................................... 600/117; 600/424

(58) Field of Classification Search
USPC .......... 600/101, 117, 118, 424, 145, 151, 152
See application file for complete search history.

(56) References Cited

U.S. PATENT DOCUMENTS

| | | | |
|---|---|---|---|
| 616,672 | A | 12/1898 | Kelling |
| 2,510,198 | A | 6/1950 | Tesmer |

(Continued)

FOREIGN PATENT DOCUMENTS

| | | |
|---|---|---|
| DE | 2823025 | 12/1979 |
| DE | 3707787 | 9/1988 |

(Continued)

OTHER PUBLICATIONS

Belson et al; U.S. Appl. No. 11/796,220 entitled "Steerable segmented endoscope and method of insertion," filed Apr. 27, 2007.

(Continued)

*Primary Examiner* — John P Leubecker

(57) ABSTRACT

One RFID equipped instrument includes an elongate body with a plurality of uniquely identified radio frequency identification chips spaced along the length of the elongate body. One system used for determining the position of an instrument includes an instrument; a plurality of radio frequency identification chips attached to the instrument; a reader connected to an antenna and adapted to communicate with each radio frequency identification chip using the antenna. One method for determining the position of an instrument using radio frequency identification chips includes providing a radio frequency identification chip reader and antenna; providing an instrument having a longitudinal axis and comprising a plurality of radio frequency identification chips placed along the longitudinal axis; moving the instrument relative to the antenna; and using information about a radio frequency identification chip detected by the antenna to determine the position of the instrument.

32 Claims, 44 Drawing Sheets

(56) References Cited

U.S. PATENT DOCUMENTS

| | | | |
|---|---|---|---|
| 2,533,494 A | 12/1950 | Mitchell, Jr. |
| 2,767,705 A | 10/1956 | Moore |
| 3,060,972 A | 10/1962 | Sheldon |
| 3,071,161 A | 1/1963 | Ulrich |
| 3,096,962 A | 7/1963 | Meijs |
| 3,162,214 A | 12/1964 | Bazinet, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,497,083 A | 2/1970 | Anderson |
| 3,546,961 A | 12/1970 | Marton |
| 3,610,231 A | 10/1971 | Takahashi |
| 3,625,084 A | 12/1971 | Low |
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada |
| 3,990,434 A | 11/1976 | Free |
| 4,054,128 A | 10/1977 | Seufert |
| 4,176,662 A | 12/1979 | Frazer |
| 4,233,981 A | 11/1980 | Schomacher |
| 4,236,509 A | 12/1980 | Takahashi |
| 4,240,435 A | 12/1980 | Yazawa et al. |
| 4,273,111 A | 6/1981 | Tsukaya |
| 4,299,230 A | 11/1981 | Kubota |
| 4,327,711 A | 5/1982 | Takagi |
| 4,366,810 A | 1/1983 | Slanetz, Jr. |
| 4,393,728 A | 7/1983 | Larson |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka |
| 4,577,621 A | 3/1986 | Patel |
| 4,592,341 A | 6/1986 | Omagari et al. |
| 4,601,283 A | 7/1986 | Chikama |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III |
| 4,788,967 A | 12/1988 | Ueda |
| 4,793,326 A | 12/1988 | Shishido |
| 4,796,607 A | 1/1989 | Allred, III |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,917,114 A | 4/1990 | Green et al. |
| 4,919,112 A | 4/1990 | Siegmund |
| 4,930,494 A * | 6/1990 | Takehana et al. ............ 600/145 |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,166,787 A | 11/1992 | Irion |
| 5,174,276 A | 12/1992 | Crockard |
| 5,174,277 A | 12/1992 | Matsumaru |
| 5,188,111 A | 2/1993 | Yates et al. |
| 5,207,695 A | 5/1993 | Trout, III |
| 5,217,001 A | 6/1993 | Nakao et al. |
| 5,220,911 A | 6/1993 | Tamura |
| 5,228,429 A | 7/1993 | Hatano |
| 5,234,448 A | 8/1993 | Wholey et al. |
| 5,243,967 A | 9/1993 | Hibino |
| 5,250,058 A | 10/1993 | Miller et al. |
| 5,251,611 A | 10/1993 | Zehel et al. |
| 5,253,647 A | 10/1993 | Takahashi |
| 5,254,809 A | 10/1993 | Martin |
| 5,257,617 A | 11/1993 | Takahashi |
| 5,259,364 A | 11/1993 | Bob et al. |
| 5,271,381 A | 12/1993 | Ailinger et al. |
| 5,271,382 A | 12/1993 | Chikama |
| 5,279,610 A | 1/1994 | Park et al. |
| 5,297,443 A | 3/1994 | Wentz |
| 5,325,845 A | 7/1994 | Adair |
| 5,337,732 A | 8/1994 | Grundfest et al. |
| 5,337,733 A | 8/1994 | Bauerfeind |
| 5,343,874 A | 9/1994 | Picha |
| 5,347,987 A | 9/1994 | Feldstin et al. |
| 5,348,259 A | 9/1994 | Blanco et al. |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A | 6/1995 | Gustafson et al. |
| 5,429,118 A | 7/1995 | Cole et al. |
| 5,437,290 A * | 8/1995 | Bolger et al. ............ 128/898 |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,489,256 A | 2/1996 | Adair |
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |

(56) References Cited

U.S. PATENT DOCUMENTS

| | | |
|---|---|---|
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,599,347 A | 2/1997 | Hart et al. |
| 5,601,087 A | 2/1997 | Gunderson et al. |
| 5,602,449 A | 2/1997 | Krause |
| 5,608,639 A * | 3/1997 | Twardowski et al. ......... 700/125 |
| 5,620,408 A | 4/1997 | Vennes et al. |
| 5,624,380 A * | 4/1997 | Takayama et al. ............ 600/146 |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |
| 5,765,561 A | 6/1998 | Chen et al. |
| 5,769,792 A | 6/1998 | Palcic et al. |
| 5,772,597 A | 6/1998 | Goldberg |
| 5,773,835 A | 6/1998 | Sinofsky |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee |
| 5,810,717 A | 9/1998 | Maeda |
| 5,810,776 A | 9/1998 | Bacich et al. |
| 5,813,976 A | 9/1998 | Filipi et al. |
| 5,827,190 A | 10/1998 | Palcic et al. |
| 5,842,973 A | 12/1998 | Bullard |
| 5,860,581 A | 1/1999 | Robertson et al. |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,893,369 A | 4/1999 | LeMole |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,916,147 A | 6/1999 | Boury |
| 5,921,915 A | 7/1999 | Aznoian et al. |
| 5,928,136 A | 7/1999 | Barry |
| 5,936,527 A * | 8/1999 | Isaacman et al. .......... 340/572.1 |
| 5,941,815 A | 8/1999 | Chang |
| 5,941,908 A | 8/1999 | Goldsteen et al. |
| 5,957,833 A | 9/1999 | Shan |
| 5,968,052 A | 10/1999 | Sullivan et al. |
| 5,971,767 A | 10/1999 | Kaufman et al. |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,993,447 A | 11/1999 | Blewett et al. |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,042,155 A | 3/2000 | Lockwood |
| 6,048,307 A | 4/2000 | Grundl et al. |
| 6,063,022 A | 5/2000 | Ben-Haim |
| 6,066,102 A | 5/2000 | Townsend et al. |
| 6,066,132 A | 5/2000 | Chen et al. |
| 6,068,638 A | 5/2000 | Makower |
| 6,069,564 A * | 5/2000 | Hatano et al. ............... 340/572.7 |
| 6,096,289 A | 8/2000 | Goldenberg |
| 6,099,464 A | 8/2000 | Shimizu et al. |
| 6,099,465 A | 8/2000 | Inoue |
| 6,099,485 A | 8/2000 | Patterson |
| 6,106,510 A | 8/2000 | Lunn et al. |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Roland |
| 6,149,581 A | 11/2000 | Klingenstein |
| 6,162,171 A | 12/2000 | Ng et al. |
| 6,174,280 B1 | 1/2001 | Oneda |
| 6,174,291 B1 | 1/2001 | McMahon et al. |
| 6,179,776 B1 | 1/2001 | Adams |
| 6,185,448 B1 | 2/2001 | Borovsky |
| 6,201,989 B1 | 3/2001 | Whitehead |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,232,870 B1 * | 5/2001 | Garber et al. ................. 340/10.1 |
| 6,241,657 B1 | 6/2001 | Chen et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker |
| 6,333,699 B1 * | 12/2001 | Zierolf ........................ 340/854.8 |
| 6,335,686 B1 * | 1/2002 | Goff et al. .................. 340/572.4 |
| 6,348,058 B1 | 2/2002 | Melkent |
| 6,352,503 B1 | 3/2002 | Matsui et al. |
| 6,366,799 B1 | 4/2002 | Acker |
| 6,396,438 B1 * | 5/2002 | Seal ............................. 342/127 |
| 6,402,687 B1 | 6/2002 | Ouchi |
| 6,408,889 B1 | 6/2002 | Komachi |
| 6,428,203 B1 | 8/2002 | Danley |
| 6,432,041 B1 * | 8/2002 | Taniguchi et al. ............ 600/118 |
| 6,443,888 B1 | 9/2002 | Ogura et al. |
| 6,453,190 B1 | 9/2002 | Acker |
| 6,459,481 B1 | 10/2002 | Schaack |
| 6,468,203 B2 | 10/2002 | Belson |
| 6,482,149 B1 | 11/2002 | Torii |
| 6,485,413 B1 | 11/2002 | Boppart |
| 6,490,467 B1 | 12/2002 | Bucholz |
| 6,511,417 B1 | 1/2003 | Taniguchi et al. |
| 6,511,418 B2 | 1/2003 | Shahidi |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,554,793 B1 | 4/2003 | Pauker et al. |
| 6,569,173 B1 | 5/2003 | Blatter et al. |
| 6,610,007 B2 | 8/2003 | Benson et al. |
| 6,616,600 B2 | 9/2003 | Pauker |
| 6,638,213 B2 | 10/2003 | Ogura et al. |
| 6,641,528 B2 | 11/2003 | Torii |
| 6,656,110 B1 | 12/2003 | Irion et al. |
| 6,689,049 B1 * | 2/2004 | Miyagi et al. ................. 600/117 |
| 6,699,183 B1 | 3/2004 | Wimmer |
| 6,750,769 B1 * | 6/2004 | Smith ........................ 340/572.1 |
| 6,761,685 B2 | 7/2004 | Adams et al. |
| 6,783,491 B2 | 8/2004 | Saadat et al. |
| 6,790,173 B2 | 9/2004 | Saadat et al. |
| 6,800,056 B2 | 10/2004 | Tartaglia et al. |
| 6,808,499 B1 | 10/2004 | Churchill et al. |
| 6,808,520 B1 | 10/2004 | Fourkas et al. |
| 6,817,973 B2 | 11/2004 | Merril et al. |
| 6,837,846 B2 | 1/2005 | Jaffe |
| 6,837,847 B2 | 1/2005 | Ewers et al. |
| 6,837,849 B2 | 1/2005 | Ogura et al. |
| 6,843,793 B2 | 1/2005 | Brock et al. |
| 6,850,794 B2 | 2/2005 | Shahidi |
| 6,858,005 B2 | 2/2005 | Ohline et al. |

(56) References Cited

U.S. PATENT DOCUMENTS

| | | |
|---|---|---|
| 6,869,396 B2 | 3/2005 | Belson |
| 6,875,170 B2 | 4/2005 | Francois et al. |
| 6,890,297 B2 | 5/2005 | Belson |
| 6,902,528 B1 | 6/2005 | Garibaldi et al. |
| 6,942,613 B2 | 9/2005 | Ewers et al. |
| 6,960,161 B2 | 11/2005 | Amling et al. |
| 6,960,162 B2 | 11/2005 | Saadat et al. |
| 6,960,163 B2 | 11/2005 | Ewers et al. |
| 6,974,411 B2 | 12/2005 | Belson |
| 6,984,203 B2 | 1/2006 | Tartaglia et al. |
| 7,018,331 B2 | 3/2006 | Chang et al. |
| 7,087,013 B2 | 8/2006 | Belson et al. |
| 7,618,374 B2* | 11/2009 | Barnes et al. ............ 600/466 |
| 2001/0051766 A1* | 12/2001 | Gazdzinski ............... 600/309 |
| 2002/0016607 A1 | 2/2002 | Bonadio et al. |
| 2002/0062062 A1 | 5/2002 | Belson et al. |
| 2002/0120254 A1 | 8/2002 | Julian |
| 2002/0147385 A1 | 10/2002 | Butler et al. |
| 2002/0151767 A1 | 10/2002 | Sonnenschein |
| 2002/0169361 A1 | 11/2002 | Taniguchi |
| 2002/0193662 A1 | 12/2002 | Belson |
| 2003/0045798 A1 | 3/2003 | Hular et al. |
| 2003/0083550 A1 | 5/2003 | Miyagi |
| 2003/0099158 A1* | 5/2003 | De la Huerga ............ 368/10 |
| 2003/0130598 A1 | 7/2003 | Manning et al. |
| 2003/0156401 A1* | 8/2003 | Komine et al. ............ 361/815 |
| 2003/0167007 A1 | 9/2003 | Belson |
| 2003/0182091 A1 | 9/2003 | Kukuk |
| 2003/0195387 A1 | 10/2003 | Kortenbach et al. |
| 2003/0233056 A1 | 12/2003 | Saadat et al. |
| 2003/0236505 A1 | 12/2003 | Bonadio et al. |
| 2003/0236549 A1 | 12/2003 | Bonadio et al. |
| 2004/0019254 A1 | 1/2004 | Belson |
| 2004/0044270 A1 | 3/2004 | Barry |
| 2004/0049251 A1 | 3/2004 | Knowlton |
| 2004/0097788 A1 | 5/2004 | Mourlas et al. |
| 2004/0106852 A1 | 6/2004 | Windheuser et al. |
| 2004/0176683 A1 | 9/2004 | Whitin et al. |
| 2004/0186350 A1 | 9/2004 | Brenneman et al. |
| 2004/0193008 A1 | 9/2004 | Jaffe et al. |
| 2004/0193009 A1 | 9/2004 | Jaffe et al. |
| 2004/0204645 A1* | 10/2004 | Saadat et al. ............ 600/424 |
| 2004/0210109 A1 | 10/2004 | Jaffe et al. |
| 2004/0220450 A1 | 11/2004 | Jaffe et al. |
| 2004/0230096 A1 | 11/2004 | Stefanchik et al. |
| 2004/0250819 A1* | 12/2004 | Blair et al. ............... 128/899 |
| 2005/0020901 A1 | 1/2005 | Belson et al. |
| 2005/0085693 A1 | 4/2005 | Belson et al. |
| 2005/0124855 A1 | 6/2005 | Jaffe et al. |
| 2005/0137454 A1 | 6/2005 | Saadat et al. |
| 2005/0137455 A1 | 6/2005 | Ewers et al. |
| 2005/0137456 A1 | 6/2005 | Saadat et al. |
| 2005/0154258 A1 | 7/2005 | Tartaglia et al. |
| 2005/0154261 A1 | 7/2005 | Ohline et al. |
| 2005/0165276 A1 | 7/2005 | Belson |
| 2005/0168571 A1 | 8/2005 | Lia et al. |
| 2005/0203339 A1 | 9/2005 | Butler et al. |
| 2005/0209506 A1 | 9/2005 | Butler et al. |
| 2005/0209509 A1 | 9/2005 | Belson |
| 2005/0222497 A1 | 10/2005 | Belson |
| 2005/0222498 A1 | 10/2005 | Belson |
| 2005/0250990 A1 | 11/2005 | Le et al. |
| 2006/0009678 A1 | 1/2006 | Jaffe et al. |
| 2006/0009679 A1* | 1/2006 | Ito et al. ................... 600/117 |
| 2006/0052664 A1 | 3/2006 | Julian et al. |
| 2006/0173289 A1* | 8/2006 | Aizawa et al. ............ 600/424 |
| 2006/0187044 A1* | 8/2006 | Fabian et al. ............ 340/572.1 |
| 2006/0235457 A1 | 10/2006 | Belson |
| 2006/0235458 A1 | 10/2006 | Belson |
| 2006/0258912 A1 | 11/2006 | Belson et al. |
| 2007/0043259 A1 | 2/2007 | Jaffe et al. |
| 2007/0093858 A1 | 4/2007 | Gambale et al. |
| 2007/0129602 A1* | 6/2007 | Bettesh et al. ............ 600/118 |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0270650 A1 | 11/2007 | Eno et al. |
| 2008/0154288 A1 | 6/2008 | Belson |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 0165718 A2 | 12/1985 |
| EP | 0382974 A1 | 8/1990 |
| EP | 0478394 A1 | 4/1992 |
| EP | 0497781 B1 | 1/1994 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 2347685 A | 9/2000 |
| IE | 2000/0225 | 3/2000 |
| IE | 2000/0559 | 7/2000 |
| IE | 2002/0170 | 3/2002 |
| JP | 47-12705 | 5/1972 |
| JP | 55116330 A | 9/1980 |
| JP | 63136014 | 6/1988 |
| JP | 63194218 A | 8/1988 |
| JP | 63272322 | 11/1988 |
| JP | 1152413 | 6/1989 |
| JP | 1229220 | 9/1989 |
| JP | 01-262372 | 10/1989 |
| JP | 2246986 | 10/1990 |
| JP | 2296209 | 12/1990 |
| JP | 3136630 | 6/1991 |
| JP | 4054970 | 2/1992 |
| JP | 4259438 A | 9/1992 |
| JP | 5011196 | 1/1993 |
| JP | 5111458 | 5/1993 |
| JP | 5305073 | 11/1993 |
| JP | 06-007287 | 1/1994 |
| JP | 07-116104 | 5/1995 |
| JP | 08-322786 | 12/1996 |
| JP | 09-028662 | 2/1997 |
| JP | 10337274 | 12/1998 |
| JP | 11042258 | 2/1999 |
| JP | 2000051216 A | 2/2000 |
| JP | 2000508223 A | 7/2000 |
| JP | 2001-046318 | 2/2001 |
| JP | 3322356 | 9/2002 |
| SU | 871786 | 10/1981 |
| SU | 1256955 | 9/1986 |
| SU | 1301701 | 4/1987 |
| WO | WO 93/17751 A1 | 9/1993 |
| WO | WO 94/19051 A1 | 9/1994 |
| WO | WO 95/04556 A2 | 2/1995 |
| WO | WO 95/09562 A1 | 4/1995 |
| WO | WO 96/05768 A1 | 2/1996 |
| WO | WO 97/10746 A1 | 3/1997 |
| WO | WO 97/25101 A2 | 7/1997 |
| WO | WO 97/29701 A1 | 8/1997 |
| WO | WO 97/29710 A1 | 8/1997 |
| WO | WO 98/17185 A1 | 4/1998 |
| WO | WO 98/24017 A2 | 6/1998 |
| WO | WO 98/29032 A1 | 7/1998 |
| WO | WO 98/49938 A1 | 11/1998 |
| WO | WO 99/16359 A1 | 4/1999 |
| WO | WO 99/33392 A1 | 7/1999 |
| WO | WO 99/51283 A2 | 10/1999 |
| WO | WO 99/59664 A1 | 11/1999 |
| WO | WO 00/10456 A1 | 3/2000 |
| WO | WO 00/27462 A1 | 5/2000 |
| WO | WO 00/54653 A1 | 9/2000 |
| WO | WO 00/74565 A1 | 12/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 A1 | 10/2001 |
| WO | WO 01/80935 A1 | 11/2001 |
| WO | WO 02/24058 A2 | 3/2002 |
| WO | WO 02/39909 A1 | 5/2002 |

(56) References Cited

FOREIGN PATENT DOCUMENTS

| WO | WO 02/47549 | A1 | 6/2002 |
|---|---|---|---|
| WO | WO 02/064028 | A1 | 8/2002 |
| WO | WO 02/068988 | A1 | 9/2002 |
| WO | WO 02/069841 | A2 | 9/2002 |
| WO | WO 02/089692 | A1 | 11/2002 |
| WO | WO 02/096276 | A1 | 12/2002 |
| WO | WO 03/028547 | A2 | 4/2003 |
| WO | WO 03/073920 | A2 | 9/2003 |
| WO | WO 03/073921 | A1 | 9/2003 |
| WO | WO 03/092476 | A2 | 11/2003 |
| WO | WO 2004/006980 | A2 | 1/2004 |
| WO | WO 2004/019769 | A1 | 3/2004 |
| WO | WO 2004/049905 | A2 | 6/2004 |
| WO | WO 2004/071284 | A1 | 8/2004 |
| WO | WO 2004/080313 | A1 | 9/2004 |
| WO | WO 2004/084702 | A1 | 10/2004 |
| WO | WO 2005/084542 | A1 | 9/2005 |
| WO | WO2006/134881 | | 12/2006 |

OTHER PUBLICATIONS

Woodley et al; U.S. Appl. No. 11/871,104 entitled "System for managing bowden cables in articulating instruments," filed Oct. 11, 2007.

Berger, W. L. et al. Sigmoid Stiffener for Decompression Tube Placement in Colonic Pseudo-Obstruction. Endoscopy. 2000; 32 (1): 54-57.

Hasson, H.M. "Technique of open laparoscopy:equipment and technique. (from step 1 to step 9)." May 1979, 2424 North Clark Street, Chicago, IL 60614. 3 pages.

Lee, et al. A highly redundant robot system for inspection. Proceedings of Conference on Intelligent Robotics in Field, Factory, Service, and Space (CIRFFSS "94). Mar. 21-24, 1994. 1:142-148. Houston, Texas.

McKernan, et al. Laparoscopic general surgery. Journal of the Medical Association of Georgia. 1990; 79 (3):157-159.

Science & Technology, Laptop Magazine. Oct. 2002. p. 98.

Slatkin, et al. The development of a robotic endoscope. Proceedings 1995 IEEE/RSJ International Conference on Intelligent Robots and Systems. Aug. 5-9, 1995. 2:162-171. Pittsburgh, Pennsylvania.

Durant, et al.; U.S. Appl. No. 12/036,976 entitled "Systems and methods for articulating an elongate body," filed Feb. 25, 2008.

EP04749353 Office Action dated Oct. 1, 2009, 5 pages.

EP04749353 Office Action dated Sep. 17, 2010, 3 pages.

EP04749353 Supplementary Partial European Search Report dated Mar. 31, 2008, 9 pages.

EP10004306 Office Action dated Sep. 19, 2011, 5 pages.

EP10004306 Search Report and Search Opinion dated Jun. 16, 2010, 8 pages.

Japanese Application No. 2006-509221 Final Rejection mailed Apr. 26, 2011, 6 pages including translation.

Japanese Application No. 2006-509221 Final Rejection mailed Jun. 1, 2010, 5 pages including translation.

Japanese Application No. 2006-509221 Rejection mailed Oct. 27, 2009, 9 pages including translation.

PCT/US04/06939 International Search Report and Written Opinion of the International Search Authority, mailed Feb. 28, 2005, 4 pages.

\* cited by examiner

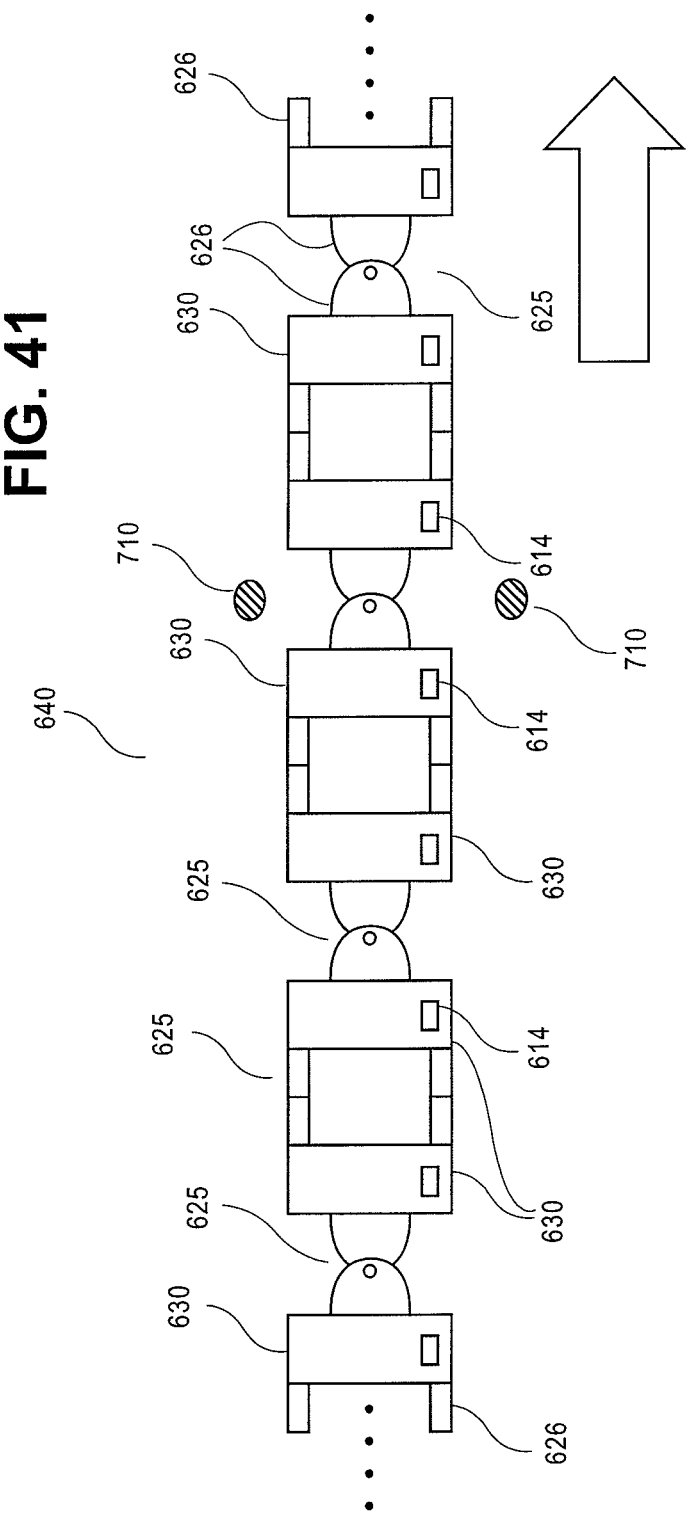

INSTRUMENT HAVING RADIO FREQUENCY IDENTIFICATION SYSTEMS AND METHODS FOR USE

CROSS REFERENCE TO RELATED APPLICATIONS

This application claims the benefit of U.S. Provisional Patent application Ser. No. 60/755,255 entitled "Endoscope Having Radio Frequency Identification Systems and Methods" filed Dec. 30, 2005 and is a continuation in part of U.S. patent application Ser. No. 10/384,252 entitled: "Method and Apparatus For Tracking Insertion Depth" filed Mar. 7, 2003, now abandoned each of which are incorporated herein by reference in its entirety.

FIELD OF THE INVENTION

The present invention relates generally to endoscopes and endoscopic medical procedures. More particularly, it relates to methods and apparatus for tracking the insertion and/or withdrawal of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135-185 cm in length and 12-19 mm in diameter, and includes a fiberoptic imaging bundle or a miniature camera located at the instrument's tip, illumination fibers, one or two instrument channels that may also be used for insufflation or irrigation, air and water channels, and vacuum channels. The colonoscope is usually inserted via the patient's anus and advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all of the way through the colon.

Another problem which arises, for example, in colonoscope procedures, is the formation of loops in the long and narrow tube of the colonoscope. Such loops may arise when the scope encounters an obstacle, or gets stuck in a narrow passage. Instead of progressing, the scope forms loops within the patient. In an attempt to proceed in insertion of the colonoscope, excess force may be exerted, damaging delicate tissue in the patient's body. The physician may proceed with the attempted insertion of the endoscope without realizing there is a problem.

Through a visual imaging device the user can observe images transmitted from the distal end of the endoscope. From these images and from knowledge of the path the endoscope has followed, the user can ordinarily determine the position of the endoscope. However, it is difficult to determine the endoscope position within a patient's body with any great degree of accuracy. This becomes even more difficult when attempting to determine endoscopic positioning using, e.g., automatically controlled endoscopic devices, as described in U.S. Pat. No. 6,468,203; U.S. patent application Ser. No. 09/969,927 filed Oct. 2, 2001; U.S. patent application Ser. No. 10/229,577 filed Aug. 27, 2002; U.S. patent application Ser. No. 10/087,100 filed Mar. 1, 2002; and U.S. patent application Ser. No. 10/139,289 filed May 2, 2002, each of which is incorporated herein by reference in its entirety.

Another method used to determine the configuration of the endoscope is x-ray imaging. Yet another method used is magnetic field positioning, which avoids the x-ray exposure to the patient and the operator. Such a method typically uses magnetic position determination via low frequency magnetic fields to determine the position of a miniature sensor embedded within the endoscope tube. Based on the position of the sensor at sequential time periods, an image of the configuration of the endoscope tube is produced.

Another method involves the placement of a series of markings on the endoscope that can aid the physician in proper placement of the device in the patient's body during a procedure. These markings can include bands, dots, lettering, numbering, colors, or other types of indicia to indicate position or movement of the device within the body. Visually distinguishable marks are often located at regular predetermined intervals. Such a system of indicia can be made to be visible under fluoroscopy by the use of certain radiopaque metals, or compounds incorporated into or printed on the device.

However, each of these methods are limited in their flexibility and applicability when the position of the endoscope within a patient's body is desired with any accuracy. Furthermore, such conventional position determination methods in many cases may also fail to account for the real-time position of the endoscope during advancement and/or withdrawal into the patient.

SUMMARY OF THE INVENTION

The information on the length of an endoscope or colonoscope inserted into a body organ within a patient may be used to aid in mapping the body organ, anatomical landmarks, anomalies, etc., and/or to maintain real-time knowledge along the entire length of the endoscope position within the body. This is particularly useful when used in conjunction with various endoscopes and/or colonoscopes having a distal steerable portion and an automatically controlled proximal portion which may be automatically controlled by, e.g., a controller. Examples of such devices are described in detail in the following granted patents and co-pending applications: U.S. Pat. No. 6,468,203; U.S. patent application Ser. No. 09/969,927 filed Oct. 2, 2001; U.S. patent application Ser. No. 10/229,577 filed Aug. 27, 2002; U.S. patent application Ser. No. 10/087,100 filed Mar. 1, 2002; and U.S. patent application Ser. No. 10/139,289 filed May 2, 2002, each of which has been incorporated by reference above.

One method for determining endoscopic insertion depth and/or position is to utilize a fully instrumented endoscopic device which incorporates features or elements configured to determine the endoscope's depth of insertion without the need for a separate or external sensing device and to relay this information to the operator, surgeon, nurse, or technician involved in carrying out a procedure. Another method is to utilize a sensing device separate from and external to the endoscope that may or may not be connected to the endoscope and which interacts with the endoscope to determine which portion of the endoscope has passed through or by a reference boundary. The external sensing device may also be referred to herein interchangeably as a datum or datum device as it may function, in part, as a point of reference relative to a position of the endoscope and/or patient. This datum may be located externally of the endoscope and either internally or externally to the body of the patient; thus, the interaction between the endoscope and the datum may be through direct contact or through non-contact interactions.

An instrumented endoscope may accomplish measurement by polling the status of the entire scope (or at least a portion of the scope length), and then determining the endoscope position in relation to an anatomical boundary or landmark such as, e.g., the anus in the case of a colonoscope. The polled information may be obtained by a number of sensors located along the length of the device. Because the sensed information may be obtained from the entire endoscope length (or at least a portion of its length), the direction of endoscope insertion or withdrawal from the body may be omitted because the instantaneous status of the endoscope may be provided by the sensors.

Aside from endoscopes being instrumented to measure insertion depth, other endoscope variations may be used in conjunction with a separate and external device that may or may not be attached to the body and which is configured to measure and/or record endoscope insertion depth. This device may be referred to as an external sensing device or as a datum or datum device. These terms are used interchangeably herein as the external sensing device may function, in part, as a point of reference relative to a position of the endoscope and/or patient. This datum may be located externally of the endoscope and either internally or externally of the body of the patient; thus, the interaction between the endoscope and the datum may be through direct contact or through non-contact interactions. Moreover, the datum may be configured to sense or read positional information by polling the status of sensors, which may be located along the body of the endoscope, as the endoscope passes into the body through, e.g., the anus. The datum may be positioned external to the patient and located, e.g., on the bed or platform that the patient is positioned upon, attached to a separate cart, or removably attached to the patient body, etc.

If the patient is positioned so that they are unable to move with any significant movement during a procedure, the datum may function as a fixed point of reference by securing it to another fixed point in the room. Alternatively, the datum may be attached directly to the patient in a fixed location relative to the point of entry of the endoscope into the patient's body. For instance, for colonoscopic procedures the datum may be positioned on the patient's body near the anus. The location where the datum is positioned is ideally a place that moves minimally relative to the anus because during such a procedure, the patient may shift position, twitch, flex, etc., and disturb the measurement of the endoscope. Therefore, the datum may be positioned in one of several places on the body.

One location may be along the natal cleft, i.e., the crease defined between the gluteal muscles typically extending from the anus towards the lower back. The natal cleft generally has little or no fat layers or musculature and does not move appreciably relative to the anus. Another location may be directly on the gluteal muscle adjacent to the anus.

In one alternative embodiment, there is provided an instrument having an elongate body; and a plurality of uniquely identified radio frequency identification chips spaced along the length of the elongate body. Additionally, the instrument may include a covering over the elongate body that contains the plurality of radio frequency identification chips. Additionally, the instrument may include a plurality of hinged segments along the length of the elongate body wherein each hinged segment of the plurality of hinged segments contains at least one uniquely identified radio frequency identification chip of the plurality of uniquely identified radio frequency identification chips. Alternatively, an antenna of at least one radio frequency identification chip of the plurality of radio frequency identification chips wraps at least partially around at least one hinged segment of the plurality of hinged segments. In another embodiment, the plurality of uniquely identified radio frequency identification chips are evenly spaced along the length of the elongate body. In another alternative, the plurality of uniquely identified radio frequency identification chips are spaced at different intervals along the length of the elongate body. Additionally, the plurality of uniquely identified radio frequency identification chips operate at a frequency of about 13.56 MHz or a frequency of about 2.45 GHz. In one embodiment, the one or more one radio frequency identification chips are contained within a 2 mm spacing along the length of the elongate body. In another embodiment, the one or more radio frequency identification chips are contained within a 1 cm spacing along the length of the elongate body. In yet another alternative, each radio frequency identification chip of the plurality of uniquely identified radio frequency identification chips is encoded with position information about the location of the radio frequency identification chip on the elongate body.

In another alternative embodiment, there is provided a system for determining the position of an instrument including an instrument; a plurality of uniquely identified radio frequency identification chips attached to the instrument; a reader connected to an antenna and adapted to communicate with each radio frequency identification chip in the plurality of uniquely identified radio frequency identification chips using the antenna. In another embodiment, the system includes a uniquely identified radio frequency identification chip separate from the radio frequency identification chips attached to the instrument and positioned within the detectable field of the antenna to always be detected by the reader without regard to the position of the instrument. In another alternative, least one radio frequency identification chip in the plurality of uniquely identified radio frequency identification chips attached to the instrument is configured to transmit an authentication code. In another alternative, the antenna and the radio frequency identification chips are configured to operate at a frequency of about 13.56 MHz or 2.45 GHz. In one embodiment, the instrument is an endoscope or a colonoscope. In another embodiment, the instrument is a segmented instrument having a controllable distal tip and a plurality of controllable proximal segments. In one embodiment, the antenna in the system is straight. In another alternative, the antenna has a circular shape sized to allow the instrument to pass through the circular shape. In one aspect, the circular shape is a circle. In another alternative, there is provided a flexible substrate wherein the uniquely identified radio frequency identification chip separate from the radio frequency identification chips attached to the instrument and the antenna are mounted. In one aspect, the flexible substrate includes an aperture sized to allow the passage of the instrument.

In yet another aspect, there is provided a method for determining the position of an instrument using radio frequency identification chips by providing a radio frequency identification chip reader and antenna; providing an instrument having a longitudinal axis and comprising a plurality of radio frequency identification chips placed along the longitudinal axis; moving the instrument relative to the antenna; and using information about a radio frequency identification chip detected by the antenna to determine the position of the instrument. In one aspect, the moving step includes passing the instrument through a hoop formed by the antenna. Another aspect includes providing information about the position of the instrument relative to the antenna to a system used to control the instrument. In one aspect, the step of providing a radio frequency identification chip reader and antenna comprises placing the antenna adjacent an opening in the body of a mammal. Additionally, the opening may be a natural opening or a surgically created opening. In another aspect, the using step comprises using information about a radio frequency identification chip detected by the antenna to determine the position of the instrument relative to the antenna. In another aspect, the information about a radio frequency identification chip includes an indication that the radio frequency identification chip has entered the opening in the body of the mammal. In one embodiment, the indication is that the reader no longer detects the radio frequency identification chip.

BRIEF DESCRIPTION OF THE DRAWINGS

FIG. 41 is a view of a segmented controllable instrument having RFID tags on each segment.

DETAILED DESCRIPTION OF THE INVENTION

Figure 1A:
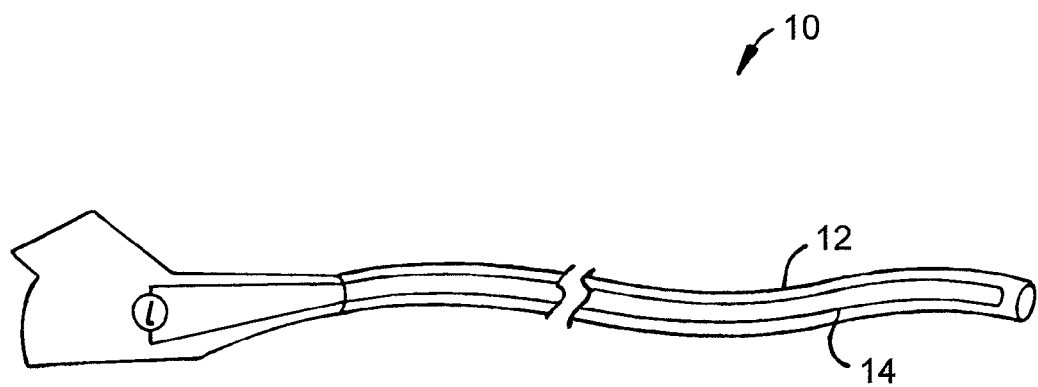
FIG. 1A shows an example of an endoscope having an electrical circuit throughout the length of the instrument.

A determination of the length of an endoscope or colonoscope inserted into a body organ within a patient, or generally into any enclosed space, is useful information which may be used to aid in mapping the body organ, anatomical landmarks, anomalies, etc., and/or to maintain real-time knowledge of the endoscope position within the body. The term endoscope and colonoscope may be used herein interchangeably but shall refer to the same type of device. This is particularly useful when used in conjunction with various endoscopes and/or colonoscopes having a distal steerable portion and an automatically controlled proximal portion which may be automatically controlled by, e.g., a controller. Examples of such devices are described in detail in the following granted patents and co-pending applications: U.S. Pat. No. 6,468,203; U.S. patent application Ser. No. 09/969,927 filed Oct. 2, 2001; U.S. patent application Ser. No. 10/229,577 filed Aug. 27, 2002; U.S. patent application Ser. No. 10/087,100 filed Mar. 1, 2002; and U.S. patent application Ser. No. 10/139,289 filed May 2, 2002, each of which has been incorporated by reference above.

There are at least two different approaches which may be utilized in determining endoscopic insertion depth and/or position when an endoscope has been inserted within the body. One method is to utilize a fully instrumented endoscopic device which incorporates features or elements which are configured to determine the endoscope's depth of insertion and to relay this information to the operator, surgeon, nurse, or technician involved in carrying out a procedure.

Another method is to utilize a sensing device separate from and external to the endoscope and which interacts with the endoscope to determine which portion of the endoscope has passed through or by a reference boundary. The external sensing device may also be referred to herein interchangeably as a datum or datum device as it may function, in part, as a point of reference relative to a position of the endoscope and/or patient. This datum may be located externally of the endoscope and either internally or externally to the body of the patient; thus, the interaction between the endoscope and the datum may be through direct contact or through non-contact interactions.

Instrumented Endoscopes

One method of determination for endoscopic insertion depth and/or position is through an endoscopic device which may be configured to determine its depth of insertion. That is, an endoscopic device may be configured to indicate the portion of the endoscope that has been inserted into a body organ without the need for a separate or external sensing device. This type of determination may reflect an endoscope configured such that its depth measurement is independent of its progress during insertion or withdrawal into the body organ and instead reflects its depth instantaneously without regards to its insertion history.

Such an endoscopic device may accomplish this, in part, by polling the status of the entire scope (or at least a portion of the scope length), and then determining the endoscope position in relation to an anatomical boundary or landmark such as, e.g., the anus in the case of a colonoscope. The polled information may be obtained by a number of sensors located along the length of the device, as described in further detail below. Because the sensed information may be obtained from the entire endoscope length (or at least a portion of its length), the direction of endoscope insertion or withdrawal from the body may be omitted because the instantaneous status of the endoscope may be provided by the sensors. Directional information or history of the endoscope position during an exploratory or diagnostic procedure may optionally be recorded and/or stored by reviewing the endoscope time history of insertion depth.

One variation is seen in FIG. 1A which shows endoscope assembly 10. Endoscope 12 may be configured to have at least a single circuit 14 wired through the length of the shaft of endoscope 12. Circuit 14 may also be wired through only a portion of the shaft length or through a majority of the shaft length depending upon the desired proportion of the shaft that the operator, surgeon, or technician desires to act as a sensor. The single circuit 14 may thus configure the endoscope 12 to function as a single continuous sensor. Depending upon the type of sensors implemented, as described in further detail below, changes in an output variable received by the sensors may be measured and recorded. The degree of change in the output variable may then be correlated to the length of the endoscope 12 inserted into the body. The change in the output variable may also be based upon varying environmental factors experienced by the endoscope 12. For instance, one example of an environmental factor which may instigate changes in the output variable sensed by the circuit 14 may include pressure sensed from the surrounding tissue, e.g., from the anus, where endoscope 12 is initially inserted into the body. Another factor may include changes in electrical conductivity, e.g., from the tissue, when the endoscope 12 is inserted into the body.

Endoscope 12 may alternatively be configured to detect and correlate the length of the endoscope 12 remaining outside the body rather than inside the body to indirectly calculate the insertion depth. Moreover, the endoscope 12 may additionally detect and correlate both the length of the endoscope 12 remaining outside the body as well as the length of endoscope 12 inserted within the body. Alternatively, endoscope 12 may sense the location of the orifice or anus 20 along the length of the device and then calculate either the length remaining outside the body or the insertion length relative to the position of anus 20.

Figure 1B:
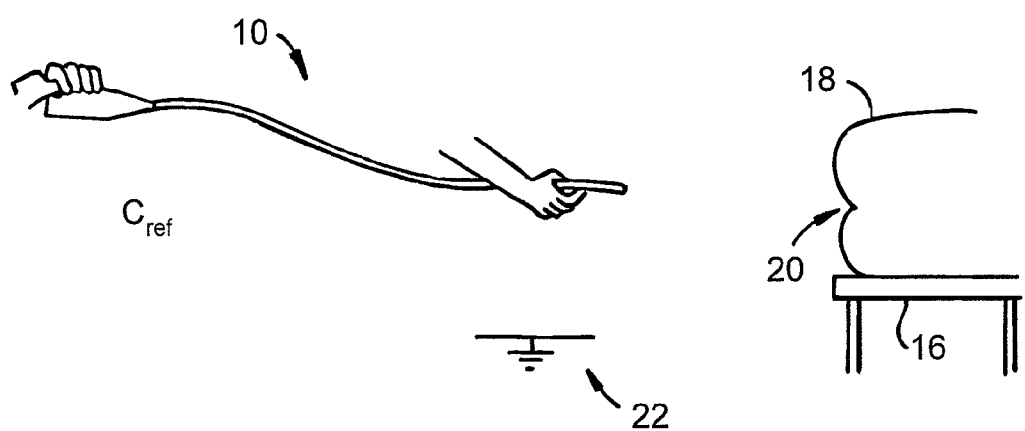
FIG. 1B shows an example of the device of FIG. 1A prior to being inserted into a patient.
Figure 1C:
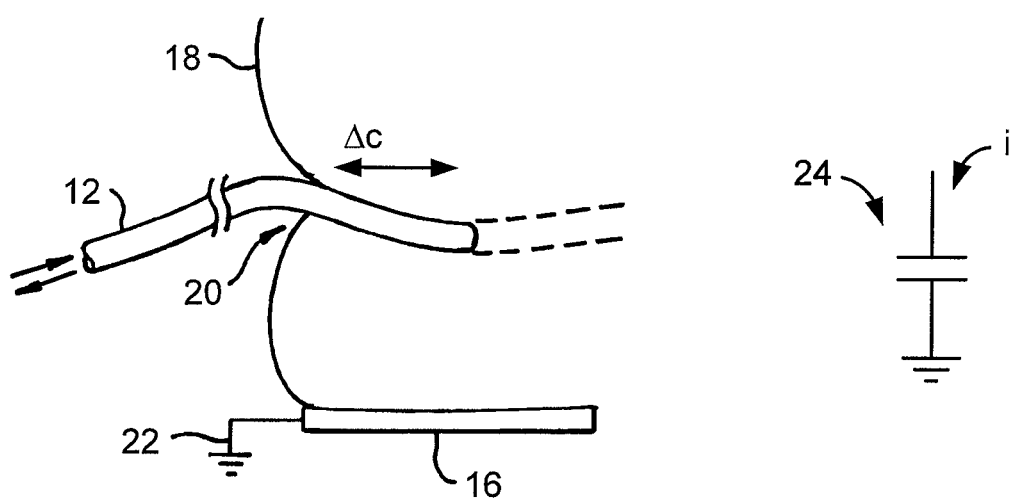
FIG. 1C shows a device sensing its position as it is advanced through the anus of the patient.

Another example of changing environmental factors leading to a change in an output variable is shown in FIGS. 1B and 1C, which show an example of endoscope assembly 10 configured as a capacitive sensing endoscopic device. As seen in FIG. 1B, patient 18 may be positioned upon table and/or grounding pad 16 which may be connected to electrical ground 22. FIG. 1C shows endoscope 12 inserted within anus 20 of patient 18. Prior to or while endoscope 12 is inserted in patient 18, a constant input current may be provided to endoscope 12 and the voltage may be measured in accordance. Endoscope 12 may thus act as a plate within a capacitor while grounding pad 16 placed under patient 18 may function as a second opposing plate to endoscope 12, as represented in the schematic 24. The resulting capacitance between endoscope 12 and grounding pad 16 may be calculated based upon the value of the current, i, over a time period, t, and/or upon the measured difference in phase shift between the input frequency and the resulting frequency. As endoscope 12 is inserted or withdrawn from anus 20, the calculated capacitance will vary according to differences in the dielectric constants between the tissue of patient 18 and that of air. This capacitance change may be constantly monitored and mapped against the length of endoscope 12 to indicate the length of insertion within patient 18.

Figure 1D:
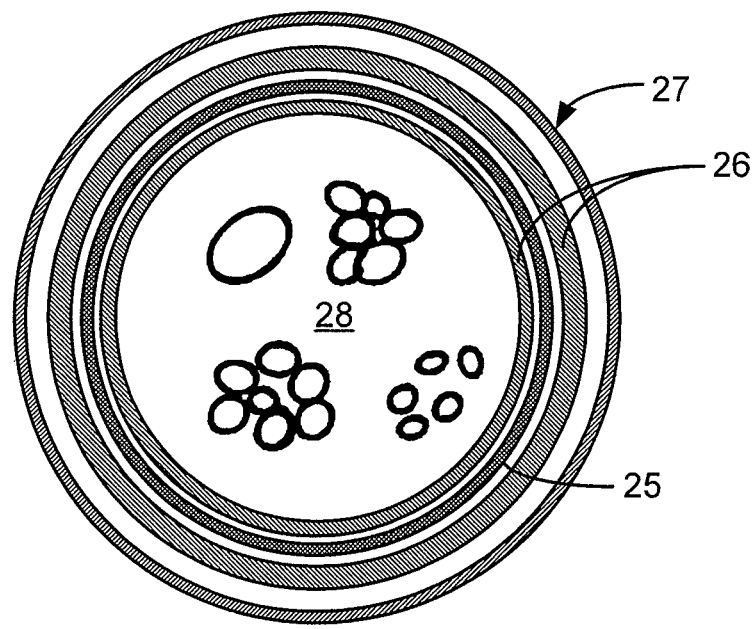
FIG. 1D shows a cross-sectional view of one variation of the endoscope of FIG. 1A.

Another variation on endoscopic sensing may utilize resistivity rather than capacitance. For instance, continuous circuit 14 may be configured into a single printed circuit with an overlay of conductive printed carbon. FIG. 1D shows one variation on a cross-section of endoscope 12 which may be configured as such. As seen, conductive printed carbon layer 25 may be positioned circumferentially within printed flex circuit 26 while surrounding endoscope interior 28. The endoscope 12 may be optionally covered by an outer jacket or sheath 27 to cover the endoscope and its electronics. In use, when the endoscope 12 is inserted into the patient 18 through, e.g., the anus 20, pressure from the surrounding tissue at the point of insertion into the body may force contact between carbon layer 25 and flex circuit 26 within endoscope 12 and thereby close the circuit 14 at the point of insertion. As endoscope 12 is inserted and withdrawn from anus 20, the contact point between carbon layer 25 and flex circuit 26 will vary according to where the pressure is applied at the point of insertion and the resistance of the circuit 14 at any one time may be measured and mapped against the length of endoscope 12 to indicate the length of insertion within anus 20.

Figure 2A:
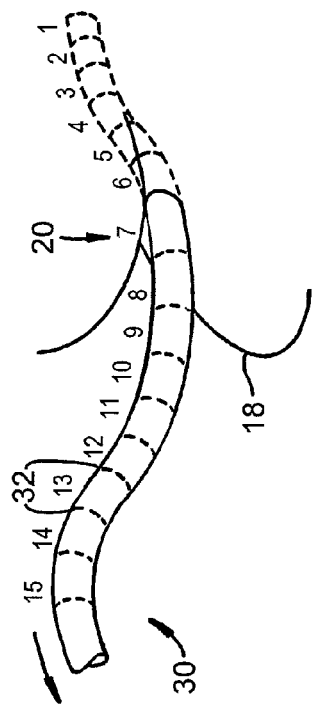
FIGS. 2A and 2B show an endoscopic device having a series of individual sensors or switches for sensing its insertion depth or position.
Figure 2B:
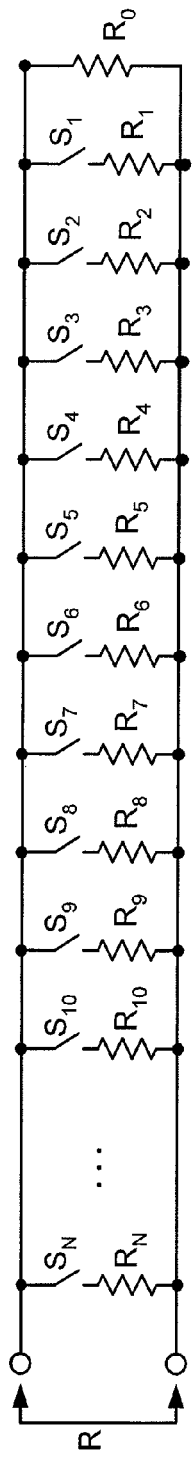

Another variation is shown in FIGS. 2A and 2B, which show an endoscopic device having a series of individual sensors or switches for sensing its insertion depth or position. Endoscope 30 is shown as having a continuous circuit with a plurality of open, individual switches or conductive sections 32 positioned along the length of the device 30. Switches, $S_1$ to $S_N$, may be positioned at regular intervals along endoscope 12. The spacing between the switches may vary and may depend upon the desired degree of accuracy in endoscope position determination. Switches may be positioned closely to one another to provide for a more accurate reading, while switches spaced farther apart from one another may provide for a less accurate determination. Moreover, the switches may be positioned at uniform distances from one another, or alternatively they may be spaced apart at irregular intervals, depending upon the desired results. The switches may also take a variety of electrically conductive forms, e.g., membrane switches, force sensitive resistors (FSR), etc.

Another variation on the type of switch which may be used is light-detecting transducers. The switches $S_1$ to $S_N$, may be configured as one of a variety of different types of photosensitive switches, e.g., photoemissive detectors, photoconductive cells, photovoltaic cells, photodiodes, phototransistors, etc. The switches $S_1$ to $S_N$, may be located at predetermined positions along the length of the endoscope 30. As the endoscope 30 is inserted into the patient 18, the change in ambient light from outside the patient 18 to inside the patient 18 may result in a voltage change in the switches inserted within the body 18. This transition may thereby indicate the insertion depth of the endoscope 30 within the body 18 or the length of the endoscope 30 still located outside the body 18. The types of photo-sensitive switches aforementioned may have a current running through them during a procedure, with the exception of photovoltaic switches, which may be powered entirely by the ambient light outside the body 18.

FIG. 2B shows a schematic representation 34 of the device of FIG. 2A. As shown, switches, $S_1$ to $S_N$, may be configured such that they are in parallel to one another. Insertion or withdrawal of the endoscope 12 within patient 18 may activate or close a switch through, e.g., interaction with electrically conductive tissue, pressure from the anus closing the switch, changes in moisture or pH, temperature changes, light intensity changes, etc. The closing of a particular switch will vary according to how deep the endoscope 12 is inserted within the anus 20. When a particular switch is electrically activated, a corresponding resistance value, ranging from $R_1$ to $R_N$, may be measured and then mapped against the endoscope 12 to indicate the length of insertion.

Figure 3A:
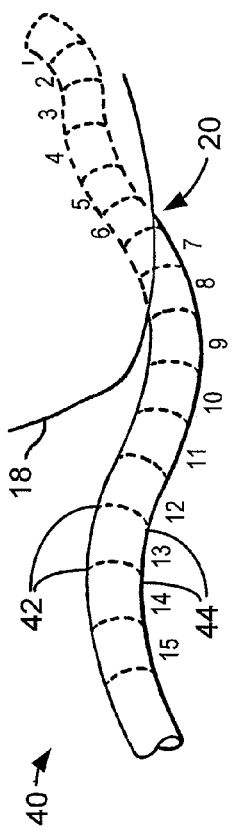
FIG. 3A shows another example of an endoscope which may have a number of sensors positioned along the length at discrete locations.
Figure 3B:
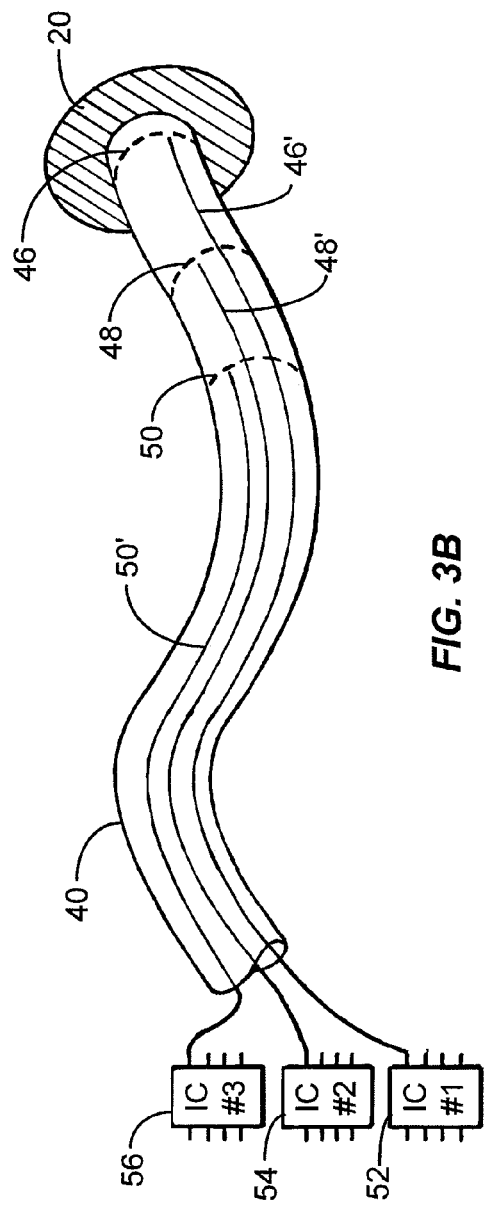
FIG. 3B shows the device of FIG. 3A with individual sensor wires leading to each of the sensors along the length.

Another variation is shown in FIGS. 3A and 3B which show an endoscope 40 having a number of sensors positioned along the length of the endoscope 40 at discrete locations. In this variation, a number of sensor wires may be placed along the length of the endoscope 12 such that each wire terminates at subsequent locations along the endoscope 12, as shown in FIG. 3B. Although only three wires are shown, this is merely intended to be illustrative and any number of fewer or additional wires may be utilized depending upon the desired length of the endoscope 12 to be instrumented. The placement of the distal ends of sensor wires 46', 48', 50' may coincide with the number of vertebrae or links of the endoscope 12 structure. The sensor wires 46', 48', 50' may be simply routed through-within the endoscope 12 length or they may be placed along the exterior of the device. The distal ends of the wires may be exposed to allow for communication with the tissue or they may alternatively be each connected to corresponding conductors 42 which divide the endoscope 12 up into a number of segments 44. These optional conductors 42 may be formed in the shape of rings to allow for circumferential contact with the tissue. Each sensor wire 46', 48', 50' may thus be in electrical communication with a corresponding conductor 46, 48, 50, respectively, and so on, depending upon the number of wires and corresponding conductors utilized. The individual sensors may also be networked together on a single bus and more complex networking and placement of sensors may also be implemented to yield additional information, e.g., rotational position of the endoscope 12. The proximal ends of the sensor wires 46', 48', 50' may each be connected to a corresponding processor 52, 54, 56, respectively, such that the length of the endoscope 12 inserted within the anus 20 may be determined by polling the status of each individual sensor wire 46', 48', 50'.

Figure 4:
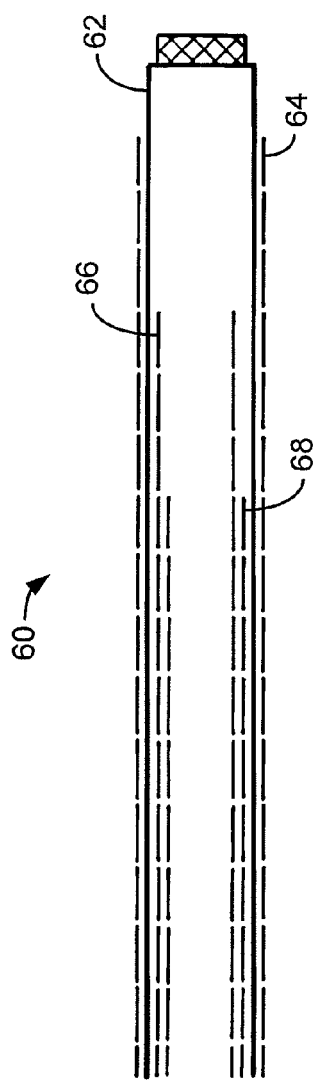
FIG. 4 shows another example in which pairs of sensor wires may be placed along the length of the endoscope terminating at discrete locations.

FIG. 4 shows another endoscopic assembly variation 60 in which corresponding pairs of wire sensors may be positioned along an endoscope 62 body. A first pair 64 of wire sensors may extend along the endoscope 62 and terminate at a first distal location; a second pair 66 of wire sensors may also extend along the endoscope 62 and terminate at a second distal location which is proximal of the first distal location; and a third pair 68 of wire sensors may also extend along the endoscope 62 and terminate at a third distal location which is proximal of the second distal location, and so on. Any number of wire pairs may be used and the distances between each of the first, second, third, etc., distal locations may be uniform or irregular, depending upon the desired measurement results. This variation 60 may operate in the same manner as above by measuring which pair of wire sensors is disrupted when inserted or withdrawn from a patient.

Figure 5A:
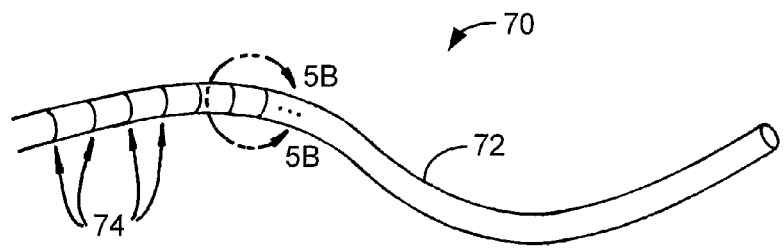
FIGS. 5A to 5D show another example of an endoscope in which the endoscope position may be determined in part by the resistance measured between adjacent sensor rings.
Figure 5B:
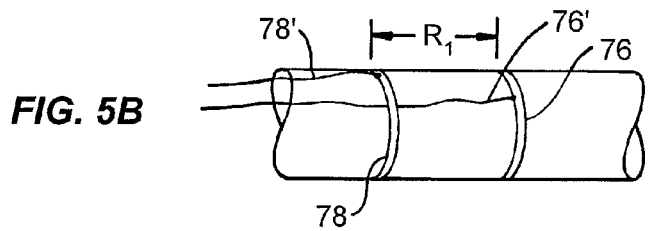
Figure 5C:
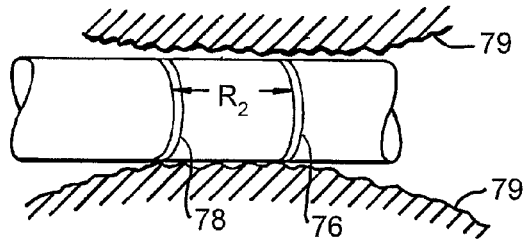
Figure 5D:
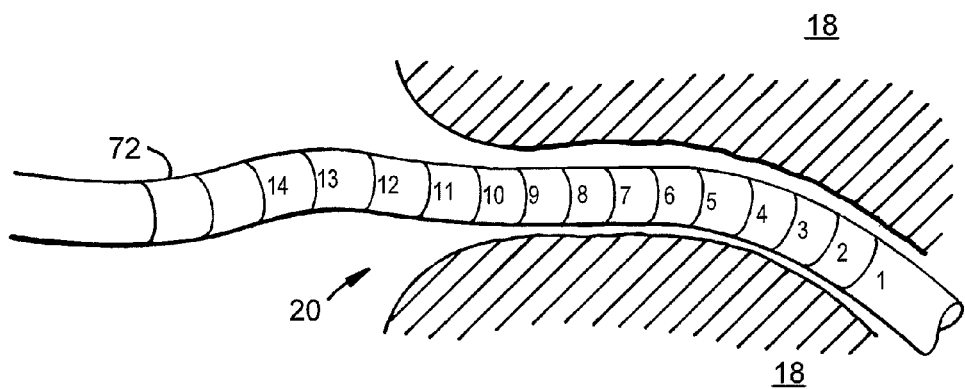

Yet another example is shown in FIGS. 5A to 5D which shows endoscope assembly 70 which may comprise an endoscope 72 having at least one or more, preferably at least two or more, conductive sensors 74 positioned along the length of endoscope 72. Sensors 74 may be in the shape of rings and may be further configured to measure resistance between each adjacent ring. FIG. 5B is a detailed view of a portion of endoscope 72 which shows first sensor 76 and adjacent second sensor 78. Each sensor 76, 78 may be connected to a separate sensor wire 76', 78' such that the electrical resistance, e.g., $R_1$, between adjacent sensors, e.g., sensors 76, 78, may be measured when contacting a region of tissue. FIG. 5C shows sensors 76, 78 contacting tissue 79. As the endoscope 72 is advanced or withdrawn from the tissue, resistance values between adjacent sensors may be measured to determine the position of the endoscope 72 within the patient 18. As seen in FIG. 5D, resistance values may be subsequently measured between each adjacent sensor, shown as sensors 1, 2, 3, etc., as the device is advanced into patient 18. This may be accomplished, in part, by correlating measured resistance values between sensors where $R \approx \infty$. when sensors are measured outside of the body, and $R \ll$ when sensors are measured inside the body when surrounded by tissue.

As mentioned above, other output variables aside from pressure or force, capacitance, and resistance measurements may also be employed to determine endoscopic insertion depth. For instance, moisture or pH sensors may be utilized since moisture or pH values change dramatically with insertion into the body. Temperature or heat flux sensing may also be utilized by placing temperature sensors, e.g., thermistors, thermocouples, etc., at varying locations along the endoscope body. Temperature sensing may take advantage of the temperature differences between air and the body. Another alternative may include heating or cooling the interior of the endoscope at ranges above or below body temperature. Thus, the resultant heat flux into or out of the endoscope, depending upon the interior endoscope temperature, may be monitored to determine which portion of the endoscope are in contact with the body tissue. Another alternative may include light sensing by positioning light sensors at locations along the endoscope body. Thus, light intensity differences may be determined between outside and inside the body to map endoscope insertion depth. Alternatively, sound waves or other pressure waves, ultrasound, inductive proximity sensors, etc., may also be utilized.

Figure 6:
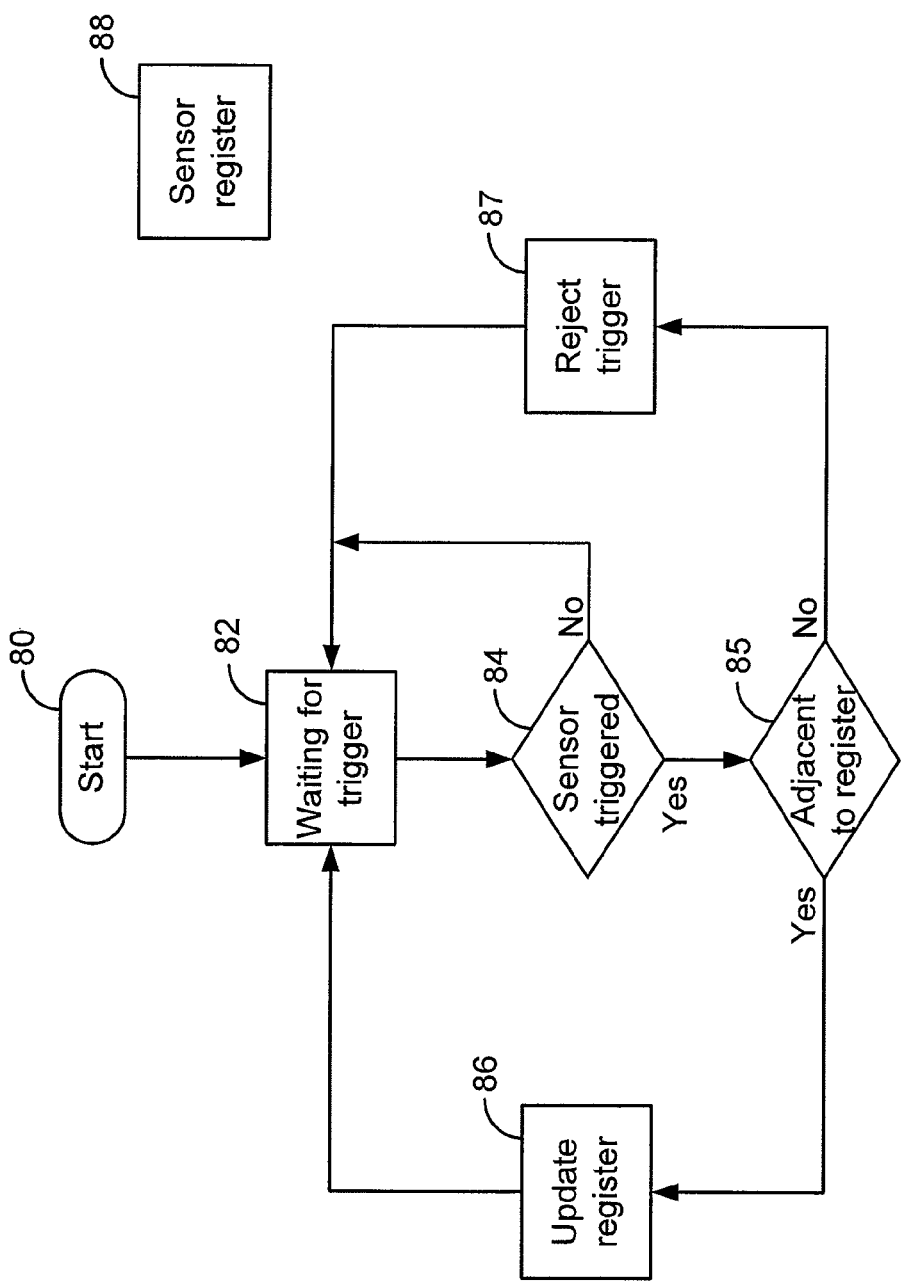
FIG. 6 shows an example of an algorithm which may be utilized for determining and recording insertion depth of an endoscope.

In utilizing sensors positioned upon the endoscope body, an algorithm may be utilized for determining and recording the insertion depth of the endoscope within a patient, as shown in FIG. 6. This variation on an algorithm operates on the general principle that each of the sensors are triggered sequentially as the endoscope is inserted or withdrawn from the patient. A register may be used to record and keep track of the latest insertion depth, i.e., the most recent and valid triggered sensor. The endoscope and algorithm may be configured such that sensor readings that are considered valid are those readings which are triggered by the same sensor or adjacent sensors such that insertion, withdrawal, or no motion may be indicated. Other sensor triggers can be ignored or rejected while valid sensor triggers may cause the register to update.

Such an algorithm may be implemented with any of the devices described above to eliminate false measurements and to maintain accurate insertion depth measurements. Step 80 indicates the start of the algorithm as the endoscope waits for a sensor to be triggered 82. If a sensor has not been triggered 84, the algorithm would indicate a "No" and the device would continue to wait for a trigger signal. Upon an indication that a sensor has been triggered 84, a comparison of the triggered signal takes place to compare whether the sensed signal is from an adjacent sensor 85 by comparing the triggered sensor information to stored register information in sensor register 88. If the triggered signal is not from an adjacent sensor, the signal is rejected as a false signal 87 and the endoscope goes back to waiting for a sensor to be triggered 82. However, if the triggered signal is from an adjacent sensor when compared to the value stored in register 88, register 88 is updated 86 with the new sensor information and the endoscope then continues to wait for another sensor to be triggered 82.

Endoscopes Using External Sensing Devices

Aside from endoscopes being instrumented to measure insertion depth, other endoscopes may be used in conjunction with a separate device configured to measure and/or record endoscope insertion depth. This separate device may be referred to as an external sensing device or as a datum or datum device. These terms are used interchangeably herein as the external sensing device may function, in part, as a point of reference relative to a position of the endoscope and/or patient. This datum may be located externally of the endoscope and either internally or externally to the body of the patient; thus, the interaction between the endoscope and the datum may be through direct contact or through non-contact interactions. Moreover, the datum may be configured to sense or read positional information by polling the status of sensors or transponders, which may be located along the body of the endoscope, as the endoscope passes into the body through, e.g., the anus. Alternatively, the datum may be configured to detect sensors or transponders only within a limited region or area. The datum may be positioned external to the patient and located, e.g., on the bed or platform that the patient is positioned upon, attached to a separate cart, or removably attached either internally or externally to the patient body, etc.

Figure 7A:
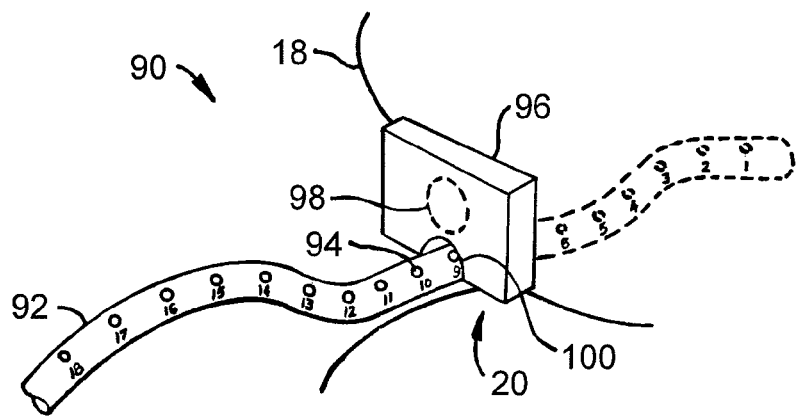
FIGS. 7A and 7B show an example of an endoscope which may utilize an external device for determining endoscope position.
Figure 7B:
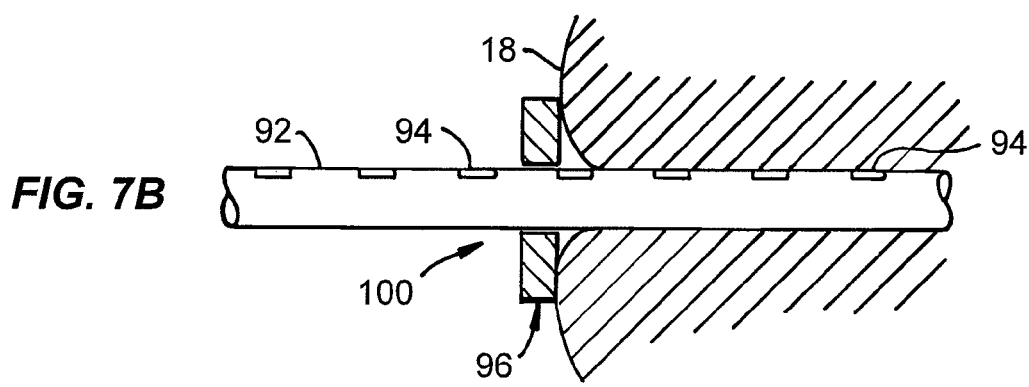

FIGS. 7A and 7B show one variation in using an endoscope assembly 90 in conjunction with external sensing device or datum 96. Datum 96 may be positioned externally of patient 18 adjacent to an opening into a body cavity, e.g., anus 20 for colonoscopic procedures. Datum 96 may accordingly have a sensor or reader 98 located next to opening 100, which may be used as a guide for passage of endoscope 92 therethrough into anus 20. Endoscope 92 may be configured to have a number of tags 94, e.g., sensors, transponders, etc., located along the body of endoscope 92. These tags 94 may be positioned at regular intervals along endoscope 92. The spacing between the tags 94 may vary and may also depend upon the desired degree of accuracy in endoscope position determination. Tags 94 may be positioned closely to one another to provide for a more accurate reading, while tags 94 spaced farther apart from one another may provide for a less accurate determination. Moreover, tags 94 may be positioned at uniform distances from one another, or alternatively they may be spaced apart are irregular intervals, depending upon the desired results. Moreover, tags 94 may be positioned along the entire length of endoscope 92 or only along a portion of it, depending upon the desired results. As shown in FIG. 7B, as endoscope 92 is passed through datum 96 via opening 100 and into anus 20, reader 98 located within datum 96 may sense each of the tags 94 as they pass through opening 100. Accordingly, the direction and insertion depth of endoscope 92 may be recorded and/or maintained for real-time positional information of the endoscope 92.

Any number of technologies may be utilized with tags 94. For instance, one variation may have tags 94 configured as RF identification tags or antennas. Reader 98 may accordingly be configured as a RF receiving device. Each tag 94 may be encoded with, e.g., position information such as the distance of a particular tag 94 from the distal end of endoscope 92. The reader 98 may be configured to thus read in only certain regions or zones, e.g., reader 98 may read only those RF tags passing through opening 100 or only those tags adjacent to anus 20. Alternatively, the RF tags may be configured to transmit the status of, e.g., pressure switches as described above, to datum 96 to determine the length of insertion.

Another variation on tags 94 may be to configure the tags for ultrasonic sensing. For example, each tag 94 may be configured as piezoelectric transducers or speakers positioned along the endoscope 92. The reader 98 may thus be configured as an ultrasonic receiver for receiving positional information from tuned transducers or tags 94 each of which relay its positional information. Alternatively, optical sensors may be used as tags 94. In this variation, each tag 94 may be configured as a passive encoded marker located on an outer surface of endoscope 92. These markers may be in the form of a conventional bar code, custom bar code, color patterns, etc., and each may be further configured to indicate directional motion, i.e., insertion or withdrawal. Furthermore, each tag 94 may be configured as active encoded markers, e.g., LEDs which may be blinking in coded patterns. Reader 98 may thus be configured as an optical sensor.

Another alternative may be to configure tags 94 and reader 98 for infrared (IR) sensing in which case IR emitters may be positioned along the length of endoscope 92 such that each IR emitter or tag 94 is configured to emit light at a specific frequency according to its position along the endoscope 92. Reader 98 may thus be configured as an IR receiver for receiving the different frequencies of light and mapping the specific frequency detected against the length of endoscope 92. Yet another alternative may be to have tags 94 configured magnetically such that a magnetic reader in datum 96 can read the position of the device, as described in further detail below.

Yet another alternative may be to configure the datum and endoscope assembly as a linear cable transducer assembly. In this variation, reader 98 may be configured as a transducer having a cable, wire, or some other flexible member extending from reader 98 and attached to the distal end of endoscope 92. While the datum 96 remains external to the patient and further remains in a fixed position relative to the patient, the endoscope 92 may be advanced within the patient while pulling the cable or wire from reader 98. The proximal end of the cable or wire may be attached to a spool of cable or wire in electrical communication with a multi-turn potentiometer. To retract the cable or wire when the endoscope 92 is withdrawn, the spool may be biased to urge the retraction of the cable or wire back onto the spool. Thus, the change of wire length may be correlated to an output of the reader 98 or of the potentiometer to a length of the extended cable and thus the length of the endoscope 92 inserted within the patient.

Yet another alternative may be to mount rollers connected to, e.g., multi-turn potentiometers, encoders, etc., on datum 96. These rollers may be configured to be in direct contact with the endoscope 92 such that the rollers rotate in a first direction when endoscope 92 is advanced and the rollers rotate in the opposite direction when endoscope 92 is withdrawn. The turning and number of revolutions turned by the rollers may be correlated into a length of the insertion depth of endoscope 92.

Yet another alternative may be to use the endoscopes, or any of the endoscopes described herein, in conjunction with conventional imaging technologies which are able to produce images within the body of a patient. For instance, any one of the imaging technologies such as x-ray, fluoroscopy, computed tomography (CT), magnetic resonance imaging (MRI), magnetic field location systems, etc., may be used in conjunction with the endoscopes described herein for determining the insertion depth.

In yet another alternative, the datum may be used to sense the positional information from the endoscope through the use of one or several pressure sensors located on the datum, e.g., datum 96. The pressure sensor may be positioned upon datum 96 such that it may press up against the endoscope 92 as it is advanced or withdrawn. This pressure sensor may be configured, e.g., as a switch, or it alternatively be configured to sense certain features on the endoscope 92, e.g., patterned textures, depressions, detents, etc., which are located at predetermined lengths or length intervals to indicate to the pressure switch the insertion depth of endoscope 92.

Figure 7C:
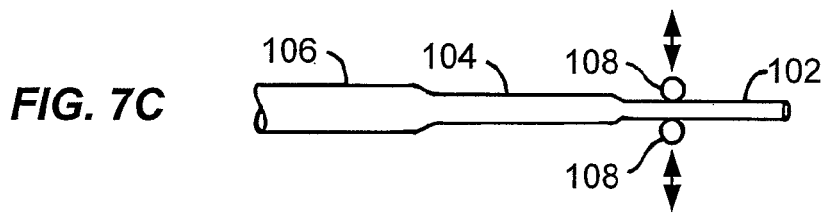
FIG. 7C shows another example of an endoscope having a non-uniform diameter utilizing an external device for determining endoscope position.

Yet another alternative is to sense changes in the diameter of the endoscope body inserted into the patient, as seen in FIG. 7C. The insertion length of the endoscope may have multiple sections each having a unique diameter, e.g., a distal most section 102 may have the smallest diameter and each successive proximal section 104, 106 may have incrementally larger diameters. Alternatively, successive sections may have alternating diameter sizes where a first section may have a first diameter, a second section may have a second larger diameter, and the third section may have a diameter equal to the first diameter or larger than the second diameter, and so on. The differences in endoscopic diameter may be used to detect the endoscopic insertion depth by using a datum 108 which may be configured to maintain contact with the endoscope and move according to the diameter changes of the endoscope, as shown by the arrows. This diameter referencing device and method may be used independently or in conjunction with any of the other methods described herein as a check to ensure that the position of the endoscope concurs with the results using other methods of sensing.

Figure 8:
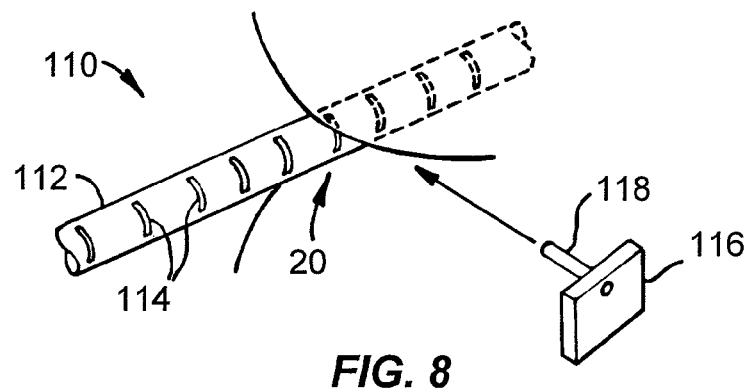
FIG. 8 shows another example of an external device which may be used to determine endoscope position.

FIG. 8 shows another example in endoscope assembly 110 in which endoscope 112 may have a number of sensors or tags 114 located along the body of the endoscope 112. As endoscope 112 is advanced or withdrawn from anus 20, datum 116, which may be mounted externally of the patient and at a distance from endoscope 112, may have a receiver or reader 118 configured in any of the variations described above. For instance, receiver or reader 118 may be adapted to function as a RF receiver, ultrasonic receiver, optical sensor, or as any of the other variations described above, to read only those tags 114 adjacent to anus 20 and to map their position on the endoscope 112 and thus, the length of insertion.

If reader 118 were configured as an optical sensor, it may further utilize a light source, e.g., LED, laser, carbon, etc., within datum 116. This light source may be utilized along with a CCD or CMOS imaging system connected to a digital signal processor (DSP) within reader 118. The light may be used to illuminate markings located at predetermined intervals along endoscope 112. Alternatively, the markings may be omitted entirely and the CCD or CMOS imaging system may be used to simply detect irregularities normally present along the surface of an endoscope. While the endoscope is moved past the light source- and reader 118, the movement of the endoscope may be detected and correlated accordingly to indicate insertion depth.

Figure 9:
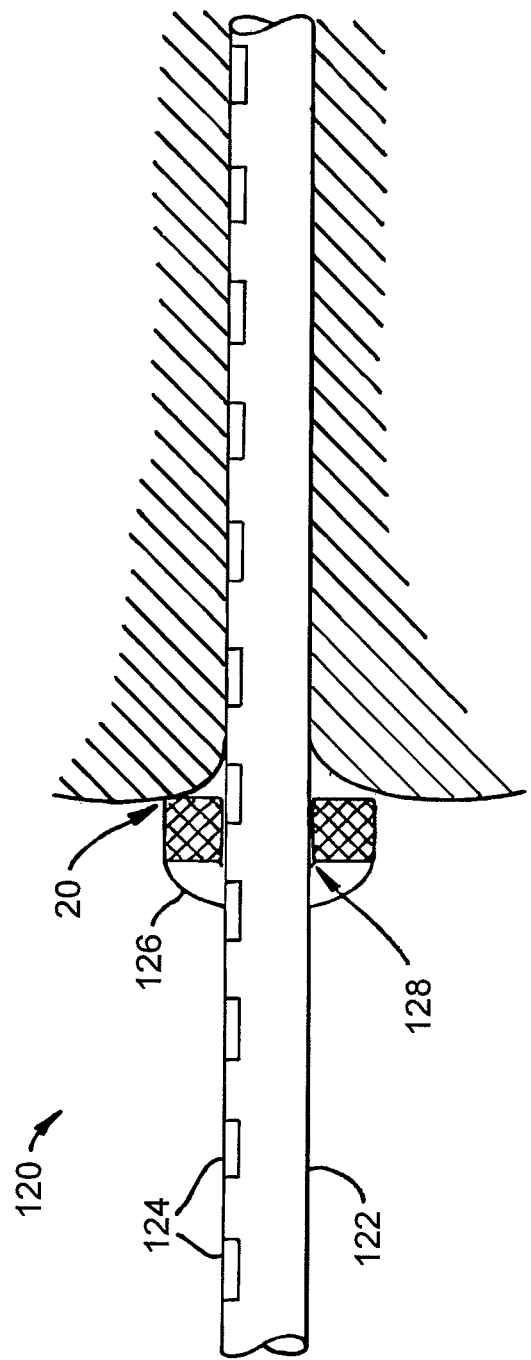
FIG. 9 shows another example of an external device which may be used to detect sensors positioned on the endoscope.

FIG. 9 shows another variation with endoscope assembly 120 in which endoscope 122 may have a number of sensors 124 located along the length of endoscope 122. These sensors 124 may be configured as Hall-effect type sensors, as will be described in greater detail below. The datum 126 may be configured as a ring magnet defining an endoscope guide 128 F therethrough such that the magnetic field is perpendicularly defined relative to the sensors 124. Thus, sensors 124 may interact with magnet 126 as they each pass through guide 128. As a Hall sensor 124 passes through datum 126, the sensor 124 may experience a voltage difference indicating the passage of a certain sensor through datum 126. These types of sensors will be described in greater detail below.

Figure 10:
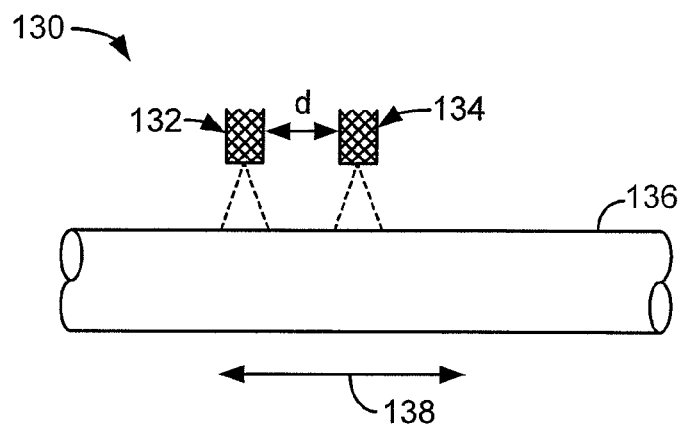
FIG. 10 shows one example of determining endoscope insertion and/or withdrawal using at least two sensors.
Figure 11A:
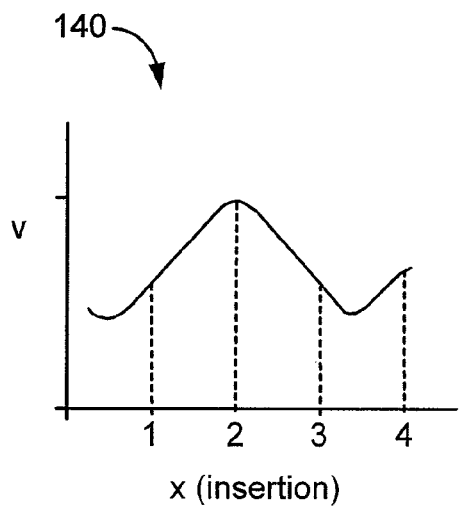
FIGS. 11A and 11B show examples of plots indicating sensor readings from the two sensors of FIG. 10 which may be used to determine whether the endoscope is being advanced or withdrawn.
Figure 11B:
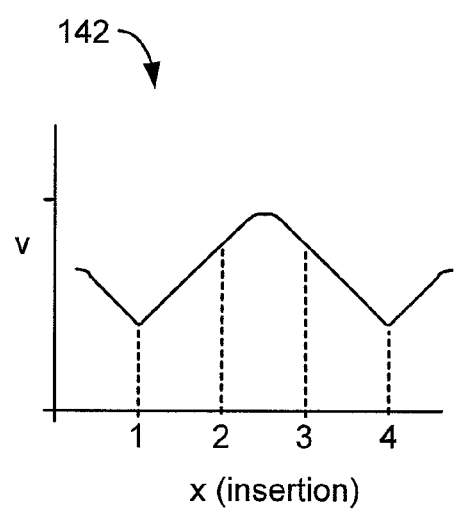

In order to determine the direction of the endoscope when it is either advanced or withdrawn from the patient, directional information may be obtained using any of the examples described above. Another example is to utilize at least two or more sensors positioned at a predetermined distance from one another. FIG. 10 shows one variation illustrating sensor detection assembly 130 with first sensor 132 and second sensor 134. First and second sensors 132, 134 may be positioned at a predetermined distance, d, from one another. As endoscope 136 is advanced or withdrawn past sensor assembly 130, the direction of travel 138 of endoscope 136 may be determined by examining and comparing the signals received from each sensor 132, 134. By determining which sensor has a rising edge or input signal first received relative to the other sensor, the direction of travel 138 may be determined. As shown in FIG. 1A, plot 140 generally illustrates signals received from first sensor 132. From position x=1 to position x=2, a rise in the signal is measured thus sensing a peak in advance of the signal measured from position x=1 to position x=2 in plot 142, which is the signal received from second sensor 134, as seen in FIG. 11B. Thus, a first direction of travel, e.g., insertion, may be indicated by the relative comparisons between signals in plots 140 and 142. If endoscope 136 were traveling in the opposite direction, e.g., withdrawal, second sensor 134 would sense a peak in advance of first sensor 132.

A more detailed description for determining the endoscope's direction of travel follows below. FIGS. 12A to 12D illustrate various cases for determining endoscopic direction of travel using first sensor 150 and second sensor 152. First and second sensors 150, 152 are preferably at a predetermined distance from one another while an endoscope is passed adjacent to the sensors. For the purposes of this illustration, a direction to the right shall indicate a first direction of travel for an endoscope device, e.g., insertion into a body, while a direction to the left shall indicate a second direction of travel opposite to the first direction, e.g., withdrawal from the body.

Figure 12A:
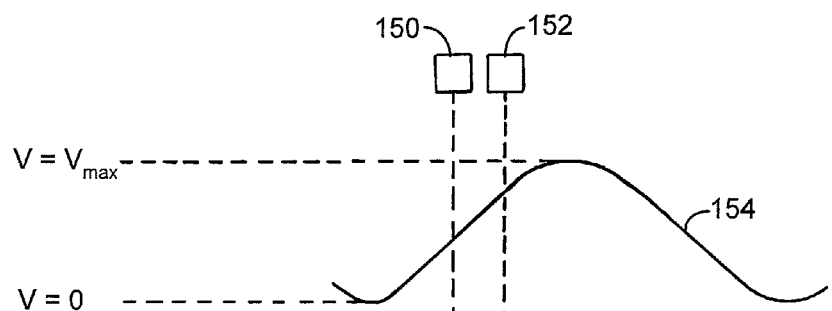
FIGS. 12A to 12D show at least four situations, respectively, on how the direction of travel for the endoscope may be determined using the two sensors of FIG. 10.
Figure 12B:
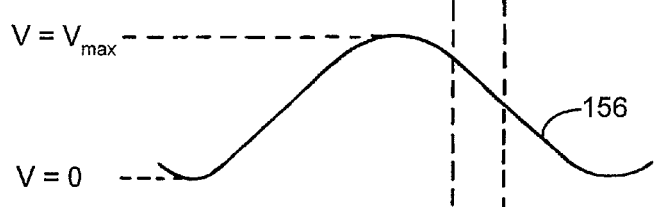

FIG. 12A shows a situation in which first sensor 150 measures a voltage less than the voltage measured by second sensor 152, as indicated by plot 154. If first and second sensors 150, 152 both measure a decrease in voltage, this may indicate a motion of the endoscope to the right while an increase voltage in both first and second sensors 150, 152 may indicate a motion of the endoscope to the left. FIG. 12B shows another situation in which first sensor 150 measures a voltage greater than the voltage measured by second sensor 152, as indicated by plot 156. If first and second sensors 150, 152 both measure an increase in voltage, this may indicate a motion of the endoscope to the right. However, if both first and second sensors 150, 152 measure a decrease in voltage, this may indicate a motion of the endoscope to the left.

Figure 12C:
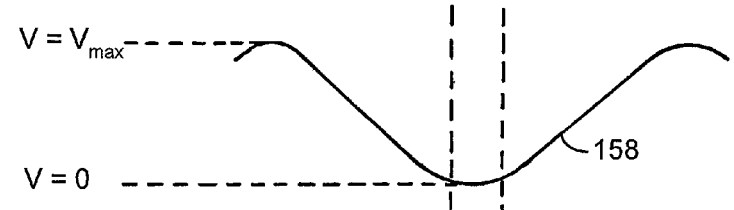
Figure 12D:
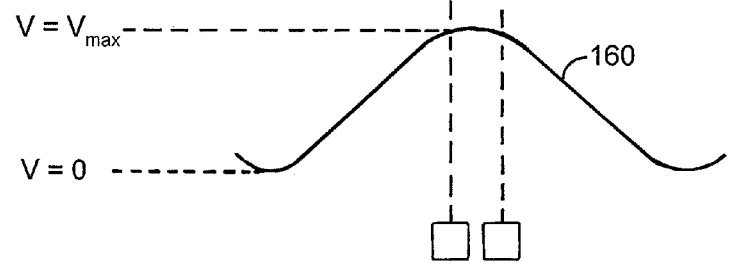

FIG. 12C shows another situation where first sensor 150 measures a voltage equal to a voltage measured by second sensor 152, as shown by plot 158. In this case, if first sensor 150 measures an increase in voltage prior to second sensor 152 also measuring an increase in voltage, this may be an indication of the endoscope moving to the right. On the other hand, if second sensor 152 measures an increase prior to first sensor 150 measuring an increase in voltage, this may indicate movement of the endoscope to the left. FIG. 12D shows a final situation in plot 160 where first sensor 150 again measures a voltage equal to a voltage measured by second sensor 152. In this case, the opposite to that shown in FIG. 12C occurs. For instance, if the voltage measured by first sensor 150 decreases prior to the voltage measured by second sensor 152, this indicates a movement of the endoscope to the right. However, if second sensor 152 measures a voltage which decreases prior to a decrease in voltage measured by first sensor 150, this may indicate a movement of the endoscope to the left.

Figure 13:
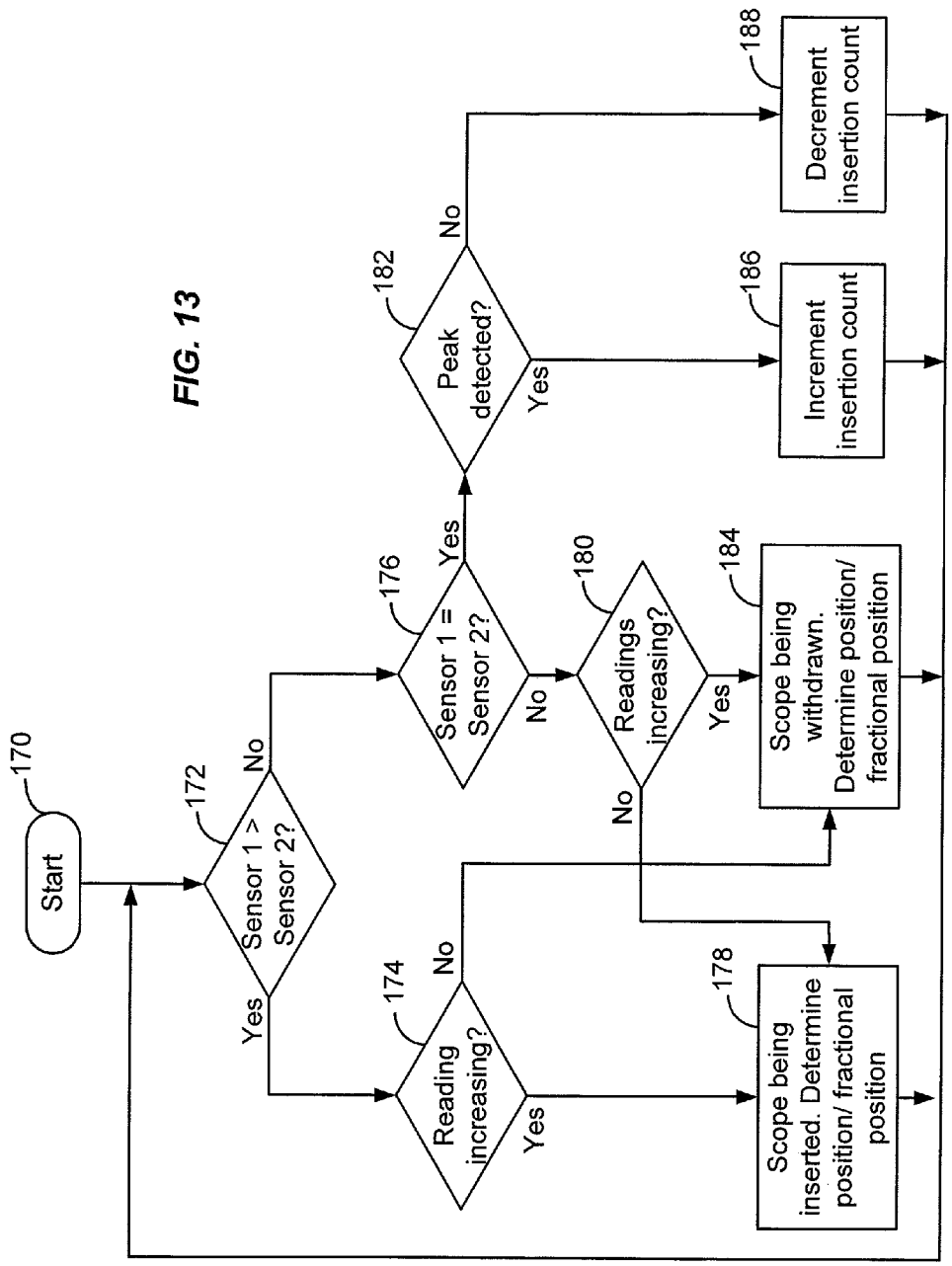
FIG. 13 shows an example of an algorithm which may be utilized for determining the endoscope direction of travel.

FIG. 13 shows one variation of an algorithm which may be implemented as one method for determining whether an endoscope is being advanced or withdrawn from the body. FIG. 13 illustrates how the various determinations described above may be combined into one variation for an algorithm. As seen, the algorithm begins with step 170. In step 172 an initial step of determining whether first sensor 150 measures a voltage greater than second sensor 152 is performed. If first sensor 150 does measure a voltage greater than second sensor 152, then a second determination may be performed in step 174 where a determination may be made as to whether the voltages measured by both sensors 150, 152 are increasing or not. If both voltages are increasing, step 178 may indicate that the endoscope is being inserted. At this point, the position of the endoscope and its fractional position, i.e., the distance traveled by the endoscope since its last measurement, may be determined and the algorithm may then return to step 172 to await the next measurement.

If, however, first sensor 150 does not measure a voltage greater than second sensor 152 in step 172, another determination may be performed in step 176 to determine whether the voltages measured by sensors 150, 152 are equal. If the voltages are not equivalent, the algorithm proceeds to step 180 where yet another determination may be performed in step 180 to determine if both voltages are increasing. If they are not, then step 178 is performed, as described above. If both voltages are increasing, then step 184 may indicate that the endoscope is being withdrawn. At this point, the position of the endoscope and its fractional position, i.e., the distance traveled by the endoscope since its last measurement, may again be determined and the algorithm may then return to step 172 to await the next measurement.

In step 176, if the voltages measured by first sensor 150 and second sensor 152 are equivalent, then the algorithm may await to determine whether a peak voltage is detected in step 182. If a peak voltage is detected, step 186 increments the insertion count. However, if a peak is not detected, then step 188 decrements the insertion count. Regardless of whether the insertion count is incremented or decremented, the algorithm may return to step 172 to await the next measurement.

Endoscopes Using Magnetic Sensing Devices

One particular variation on measuring endoscopic insertion depth may utilize magnetic sensing, in particular, taking advantage of the Hall effect. Generally, the Hall effect is the appearance of a transverse voltage difference in a sensor, e.g., a conductor, carrying a current perpendicular to a magnetic field. This voltage difference is directly proportional to the flux density through the sensing element. A permanent magnet, electromagnet, or other magnetic field source may be incorporated into a Hall effect sensor to provide the magnetic field. If a passing object, such as another permanent magnet, ferrous material, or other magnetic field-altering material, alters the magnetic field, the change in the Hall-effect voltage may be measured by the transducer.

Figure 14:
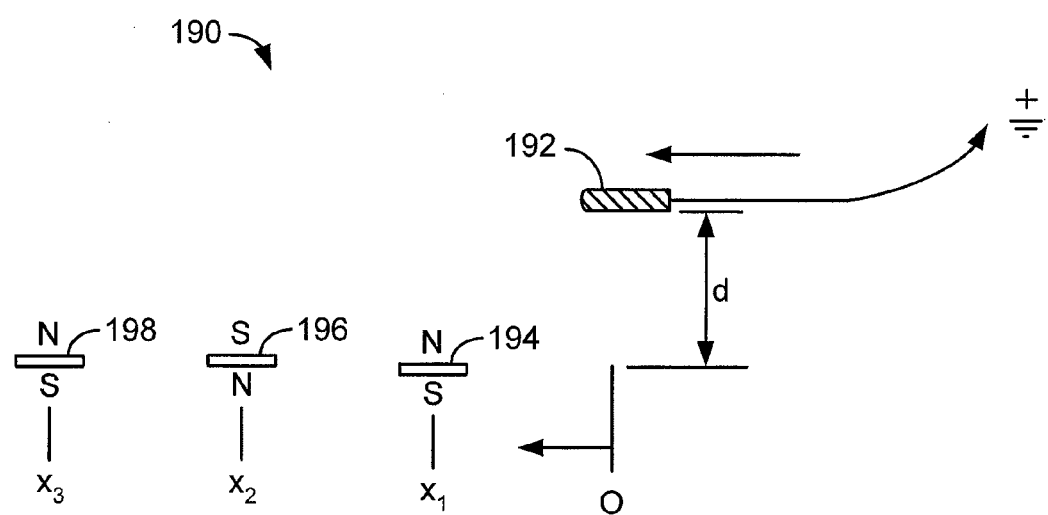
FIG. 14 shows a simplified example for determining endoscope position with an external device.

FIG. 14 illustrates generally Hall effect sensor assembly 190 which shows conductor or sensor 192 maintained at a distance, d, as it is passed over magnets 194, 196, 198 at distances $x_1$, $x_2$, $x_3$, respectively. Each magnet may be positioned such that the polarity of adjacent magnets is opposite to one another or such that the polarity of adjacent magnets is the same. As sensor 192 is passed, voltage differences may be measured to indicate which magnet sensor 192 is adjacent to.

Figure 15:
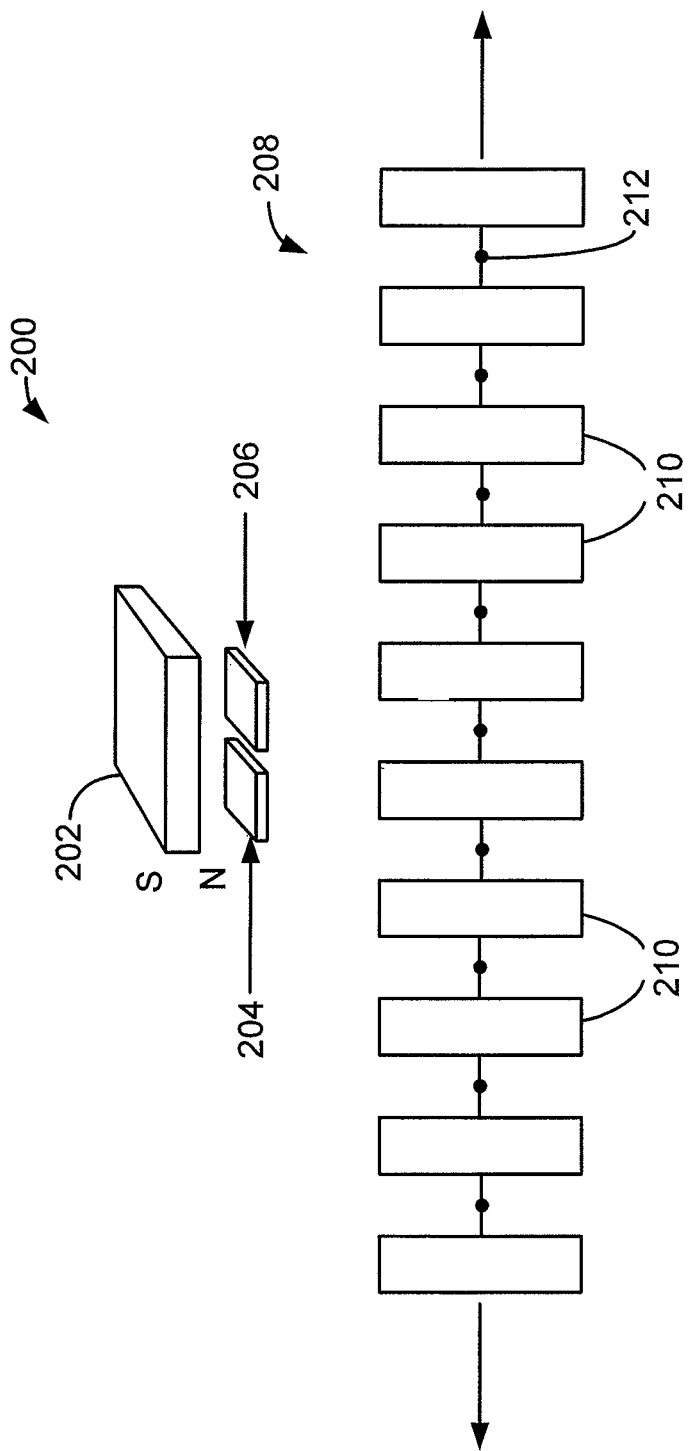
FIG. 15 shows an example illustrating the positioning which may be utilized for an external device with an endoscope.

FIG. 15 shows one variation illustrating the general application for implementing Hall effect sensors for endoscopic position measurement. As shown, sensor assembly 200 illustrates one variation having magnet 202 with first sensor 204 and second sensor 206 adjacent to magnet 202. Magnet 202 may be a permanent magnet or it may also be an electromagnet. First and second sensors 204, 206 are connected to a power supply (not shown) and are positioned from one another at a predetermined distance. Both sensors 204, 206 may also be located at a predetermined distance from magnet 202. A general representation of endoscope 208 is shown to reveal the individual links or vertebrae 210 that may comprise part of the structure of the endoscope, as described in further detail in any of the references incorporated above. Each vertebrae 210 is shown as being schematically connected to adjacent vertebrae via joints 212 which may allow for endoscope articulation through tortuous paths. Endoscope 208 may be passed by sensor assembly 200 at a predetermined distance as it is inserted or withdrawn from an opening in a patient. Each or a selected number of vertebrae 210 may be made of a ferrous material or other material that may alter or affect a magnetic field or have ferrous materials incorporated in the vertebrae 210. Thus, as endoscope 208 passes first and second sensors 204, 206, the ferrous vertebrae 210 may pass through and disrupt a magnetic field generated by magnet 202 and cause a corresponding voltage measurement to be sensed by sensors 204, 206. Direction of travel for endoscope 208, i.e., insertion or withdrawal, as well as depth of endoscope insertion may be determined by applying any of the methods described above.

Figure 16:
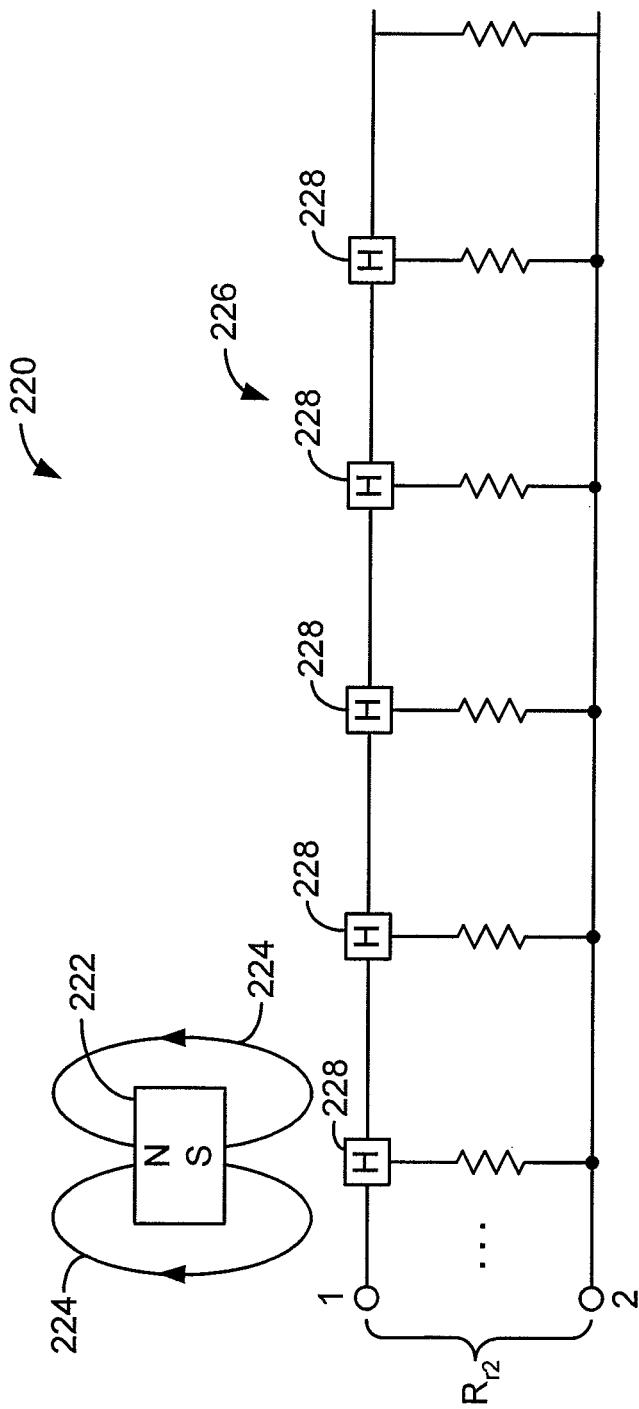
FIG. 16 shows a schematic variation utilizing a single magnetic device and multiple sensors.

Another variation is shown in FIG. 16 which illustrates a schematic representation 220 of Hall effect sensing in which the sensors may be located on the endoscope 226 itself. Magnet 222 may be positioned adjacent to, e.g., the anus of a patient, such that endoscope 226 passes adjacent to magnet 222 when inserted or withdrawn from the patient. Endoscope 226 may have a number of discrete Hall switches 228 positioned along the body of endoscope 226. As endoscope 226 passes magnet 222, the magnetic field lines 224 may disrupt a switch 228 passing adjacently. Hall switches 228 may be bipolar, unipolar, latched, analog, etc. and may be used to determine the total resistance RI 2 in order to determine insertion length of the endoscope 226.

Figure 17A:
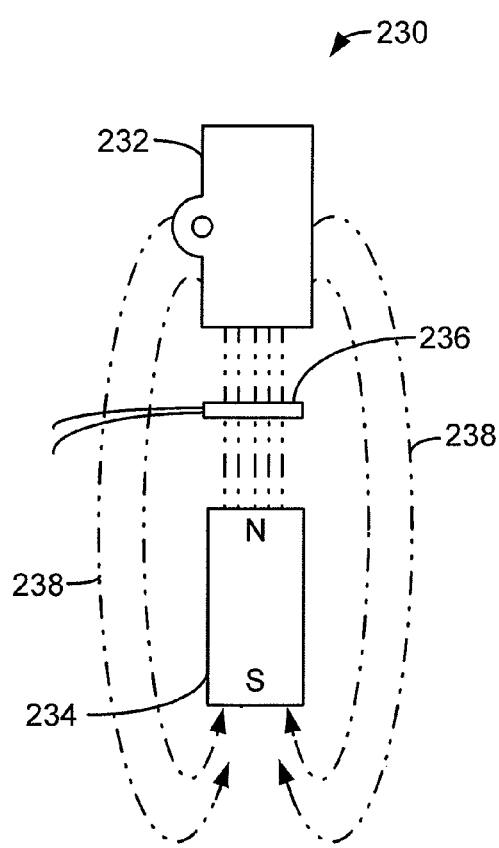
FIGS. 17A and 17B illustrate one example for sensing individual segments of an endoscopic device as it passes the sensor.
Figure 17B:
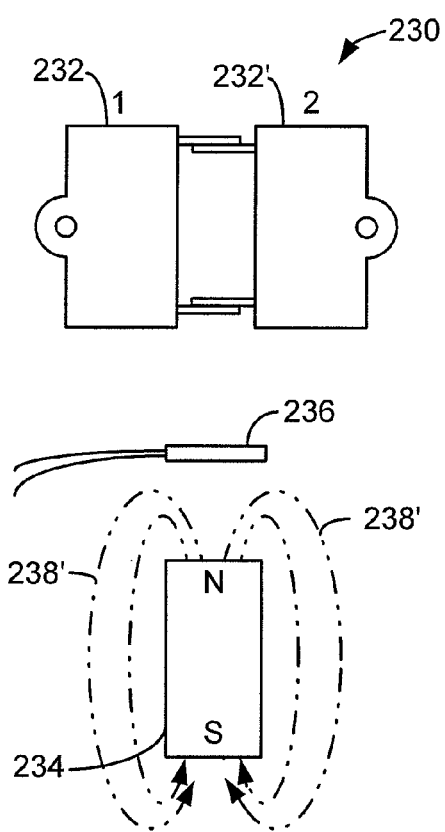

FIGS. 17A and 17B show another variation for Hall sensor positioning. FIG. 17A shows a sensor assembly 230 adjacent to an individual vertebrae 232 of an endoscope. A single vertebrae 232 is shown only for the sake of clarity. As seen, when vertebrae 232 is directly adjacent to magnet 234, magnetic flux lines 238 are disrupted and are forced to pass through sensor 236. Flux lines 238 passing through sensor 236 may cause a disruption in the current flowing therethrough and may thus indicate the passage of the endoscope. FIG. 17B shows the assembly of FIG. 17A when endoscope 230 has been advanced or withdrawn fractionally such that magnet 234 is positioned inbetween adjacent vertebrae 232 and 232'. When a vertebra is not immediately adjacent to magnet 234, flux lines 238' may return to their normal undisturbed state such that sensor 236 is also undisturbed by magnetic flux. The resumption of current within sensor 236 may indicate that endoscope 230 has been moved relative to sensor assembly 230.

Figure 18:
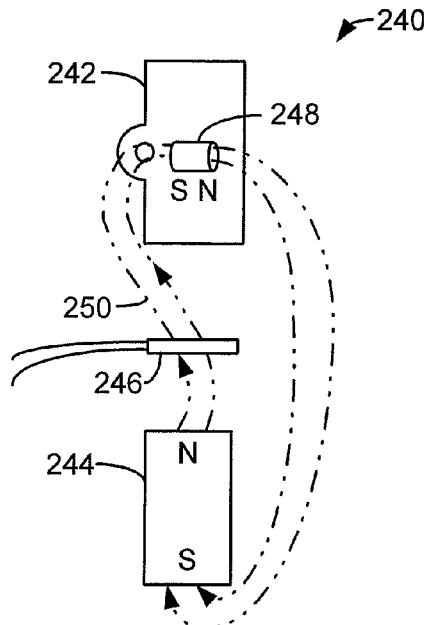
FIG. 18 shows another example for sensing individual segments of an endoscopic device having discrete permanent magnets or electromagnets positioned along the endoscope.

FIG. 18 shows another variation in assembly 240 where a discrete magnet 248 may be positioned on individual vertebrae 242 to produce a more pronounced effect in sensor measurement. Magnets 248 may be positioned along the longitudinal axis of the endoscope for creating a uniform magnetic field radially about the endoscope. Discrete magnets 248 may be permanent magnets or they may alternatively be electromagnets. In either case, they may be placed on as many or as few vertebrae or at various selected positions along the endoscope body depending upon the desired measurement results. As shown, when vertebrae 242 having discrete magnet 248 mounted thereon is brought into the vicinity of magnet 244, the interaction between the magnets produces an enhanced flux interaction 250 such that Hall sensor 246 is able to sense a more pronounced measurement. The polarity of each individual magnet 248 located along the endoscope body may be varied from location to location but the polarity of adjacent magnets on the endoscope body are preferably opposite to one another.

Alternatively, a number of magnets each having a unique magnetic signature may be placed at predetermined positions along the length of the endoscope. Each magnet 248 may be mapped to its location along the endoscope so when a magnet having a specific magnetic signature is detected, the insertion depth of the endoscope may be correlated. The magnets 248 may have unique magnetic signatures, e.g., measurable variations in magnetic field strength, alternating magnetic fields (if electromagnets are utilized), reversed polarity, etc.

Figure 19A:
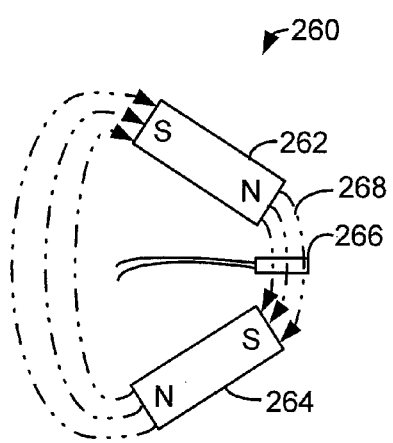
FIGS. 19A and 19B illustrate another example for sensing individual segments of an endoscopic device using multiple permanent magnets or electromagnets.
Figure 19B:
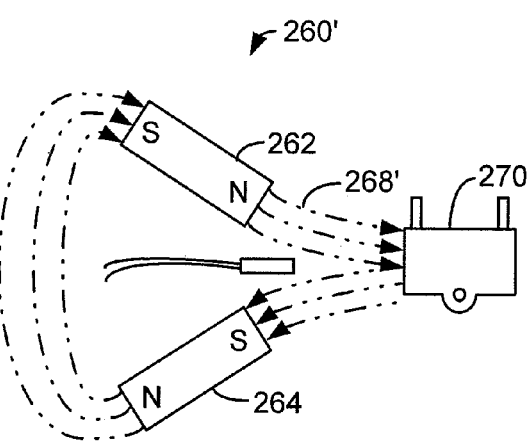

FIGS. 19A and 19B show yet another variation in assembly 260 in which more than one magnet may be used in alternative configurations. A first magnet 262 may be positioned at an angle relative to a second magnet 264 such that the combined flux lines 268 interact in accordance with each magnet. Thus, the polarity of each magnet 262, 264 may be opposite to one another as shown in the figures. Sensor 266 may be positioned such that the undisturbed field lines 268 pass through sensor 266. As vertebrae 270 is passed adjacent to sensor 266, the disturbed flux lines 268', as shown in assembly 260' in FIG. 19B, may be altered such that they no longer pass through sensor 266 due to the interaction with vertebrae 270. Alternatively, the field lines 268 passing through sensor 266 may be altered in strength as vertebrae 270 passes.

Figure 20:
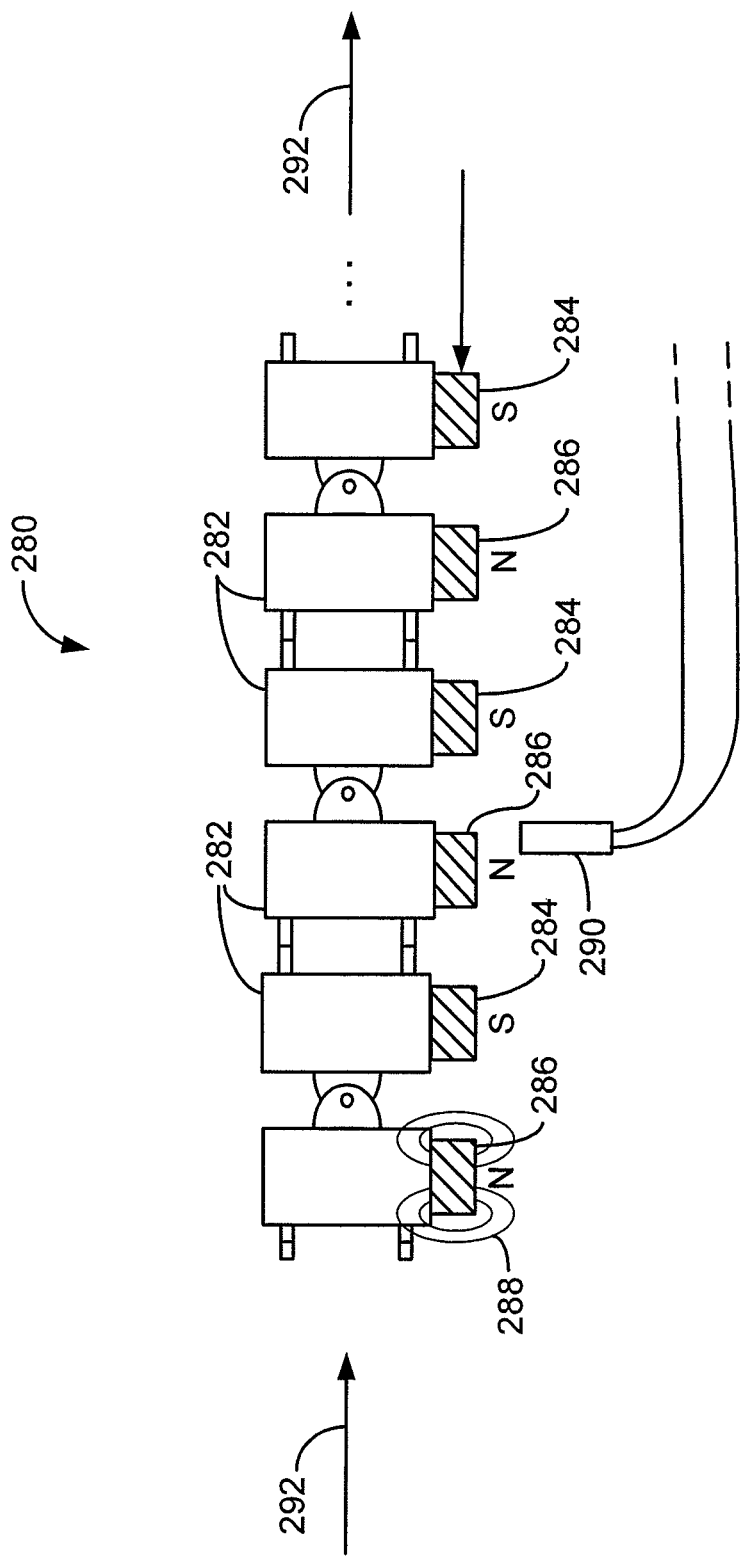
FIG. 20 shows only the vertebrae of an endoscopic device, for clarity, with discrete permanent magnets or electromagnets positioned along the endoscope.

FIG. 20 shows yet another variation in which discrete magnets may be placed on each individual vertebrae of an endoscope assembly. As shown, sensor assembly 280 shows only the vertebrae 282 of an endoscope for clarity. Discrete magnets 284 having a first orientation may be placed on alternating vertebrae 282 while magnets 286 having a second orientation may be placed on alternating vertebrae 282 inbetween magnets 284. Thus, when the endoscope is moved, e.g., along the direction of travel 292, flux lines 288 having alternating directions on each vertebrae 282 can be sensed by sensor 290. The measured alternating flux lines may be used as an indication of endoscope movement in a first or second direction. Each of the magnets may be positioned along the periphery of the vertebrae on a single side; however, they may also be positioned circumferentially, as described below in further detail.

Figure 21A:
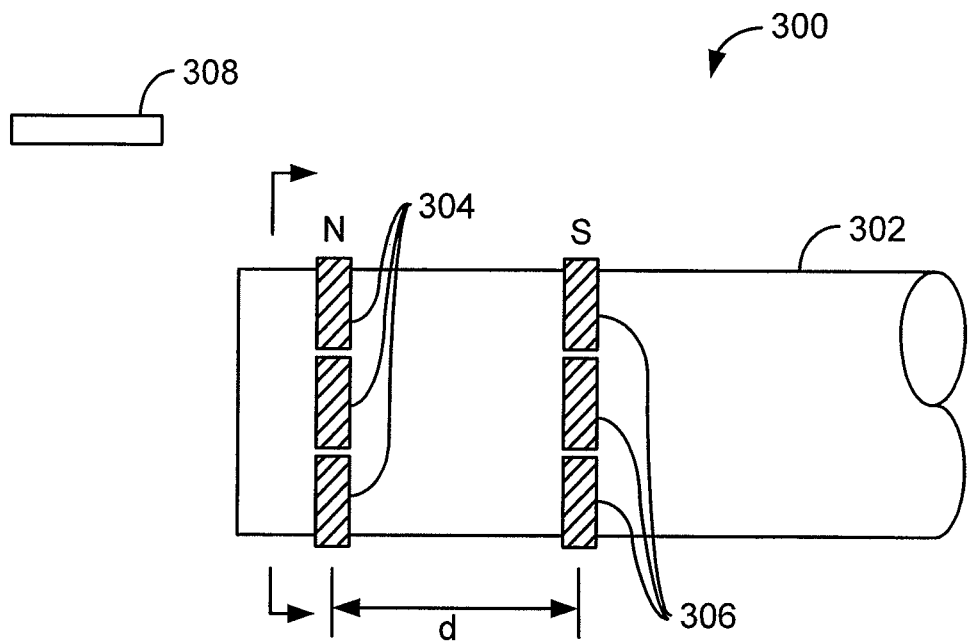
FIGS. 21A and 21B show side and cross-sectional views, respectively, of another example for magnet positioning along the endoscope.
Figure 21B:
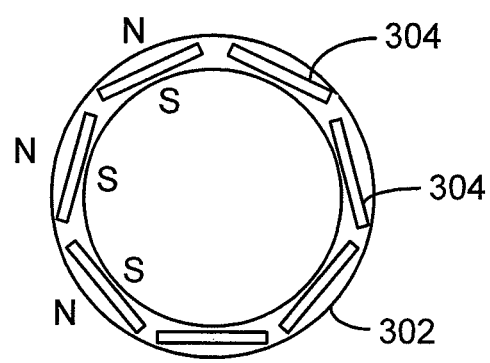

FIGS. 21A and 21B show side and cross-sectional views, respectively, of another alternative in magnet positioning. FIG. 21A shows a side view of endoscope assembly 300 in which a number of magnets 304 having a first orientation may be positioned circumferentially about endoscope 302. A number of magnets 306 having a second orientation opposite to the first orientation may also be positioned circumferentially about endoscope 302 separated a distance, d, longitudinally away from magnets 304. With discrete magnets positioned circumferentially about endoscope 302, the rotational orientation of endoscope 302 becomes less important as it passes sensor 308 in determining the insertion depth of the device. FIG. 21B shows a cross-sectional view of the device of FIG. 21A and shows one example of how magnets 304 may be positioned about the circumference. Although this variation illustrates magnets 304 having a "N" orientation radially outward and a "S" orientation radially inward of endoscope 302, this orientation may be reversed so long as the adjacent set of circumferential magnets is preferably likewise reversed. Moreover, although seven magnets are shown in each circumferential set in the figure, any number of fewer or more magnets may be used as practicable.

Figure 22A:
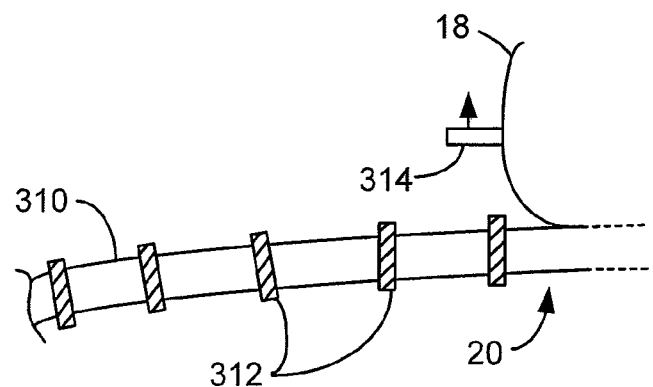
FIGS. 22A and 22B show another example for applying ferrous material, other materials that may alter or affect a magnetic field, permanent magnets, or electromagnets along the endoscope.
Figure 22B:
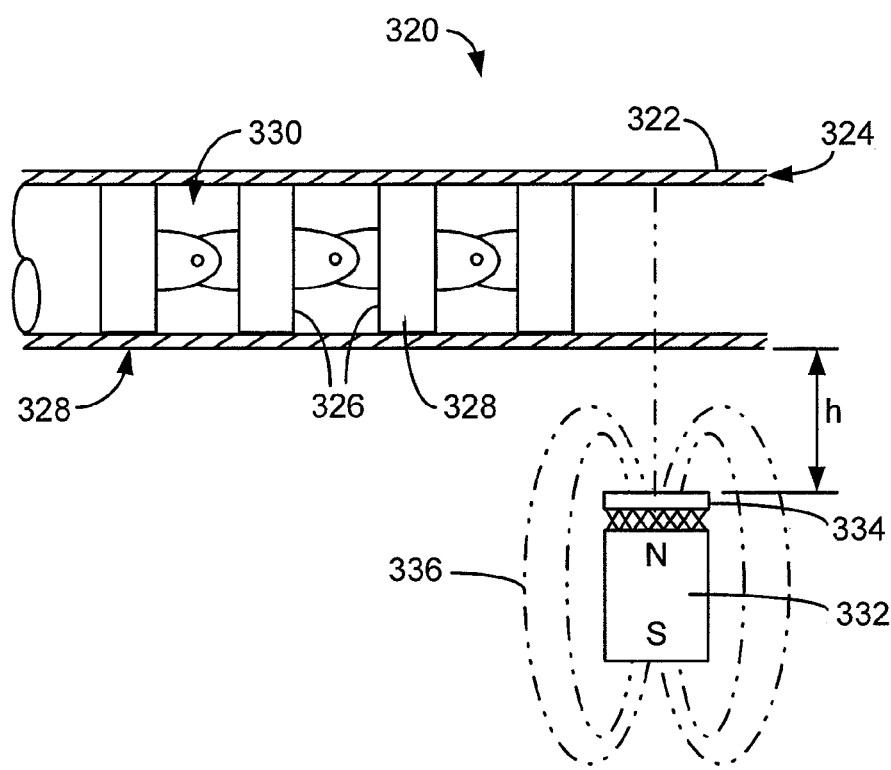

FIG. 22A shows yet another variation in which endoscope 310 may have discrete circumferentially positioned magnets 312 placed at each vertebrae 312 on an outer surface of the endoscope 310. As endoscope 310 is passed into anus 20, Hall sensor 314 may be positioned adjacent to anus 20 such that sensor 314 is able to read or measure the discrete magnets 312 as they pass into anus 20. FIG. 22B shows yet another variation in which endoscope assembly 320 may have endoscope 322 in which individual vertebrae 326 may have some ferromagnetic material 328 integrated or mounted onto or within the vertebrae 326. The ferromagnetic material 328 may be in the form of a band, coating, or other non-obstructive shape for integration onto vertebrae 326 or for coating over portions of vertebrae 326. A sheath or skin 324 may be placed over the vertebrae 326 to provide for a lubricious surface. Inbetween vertebrae 326, non-magnetic regions 330 may be maintained to provide for the separation between vertebrae 326 and between ferromagnetic material 328. Moreover, ferromagnetic material 328 may be applied retroactively not only to endoscopes having vertebrae, but also other conventional endoscopes for which a determination of insertion depth is desired. As endoscope 322 passes magnet 332, sensor 334 may detect disturbances in flux lines 336 as the regions having the ferromagnetic material 328 passes. Additionally, endoscope 322 may be passed at a distance, h, from sensor 334 which is sufficiently close to enable an accurate measurement but far enough away so as not to interfere with endoscope 322 movement.

Figure 23:
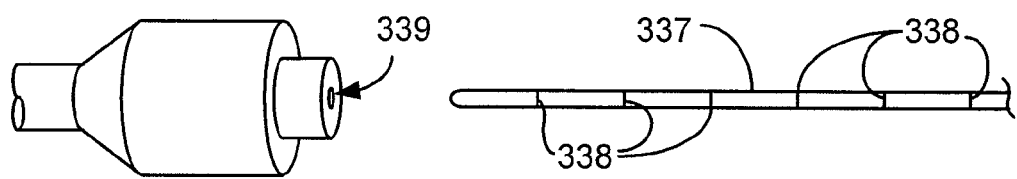
FIG. 23 shows another example in which magnets or ferrous material, or other materials that may alter or affect a magnetic field, may be positioned along an elongate support or tool which may then be positioned within the working lumen of a conventional endoscope.

FIG. 23 shows yet another variation in which conventional endoscopes may be used with any of the Hall sensor datum devices described herein. As shown, elongate support or tool 337 may have a number of magnets 338, or ferrous material or other materials that may alter or affect a magnetic field, positioned along the tool at predetermined intervals. Magnets 338 may be positioned along the length of tool 337 such that the adjacent magnets are either alternating in polarity or uniform in polarity. Furthermore, magnets 338 may be made integrally within the tool 337 or they may be made as wireforms or members which may be crimped about tool 337. Tool 337 may be positioned within the working lumen 339 of any conventional endoscope for use with a datum device as described herein. The inclusion of the tool 337 may then enable the determination of insertion depth of a conventional or instrumented endoscope. If a conventional endoscope is used, tool 337 may be securely held within the working lumen 339 during an exploratory procedure. Tool 337 may optionally be removed during a procedure to allow for the insertion of another tool and then reinserted within lumen 339 at a later time to proceed with the insertion and/or withdrawal of the endoscope.

Figure 24A:
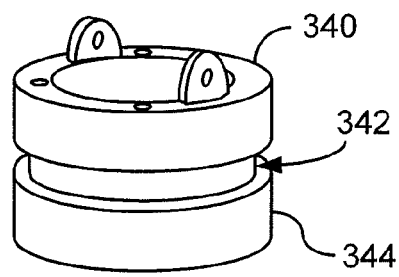
FIGS. 24A to 24C show various examples for attaching ferrous materials or other materials that may alter or affect a magnetic field to individual vertebrae of an endoscope.
Figure 24B:
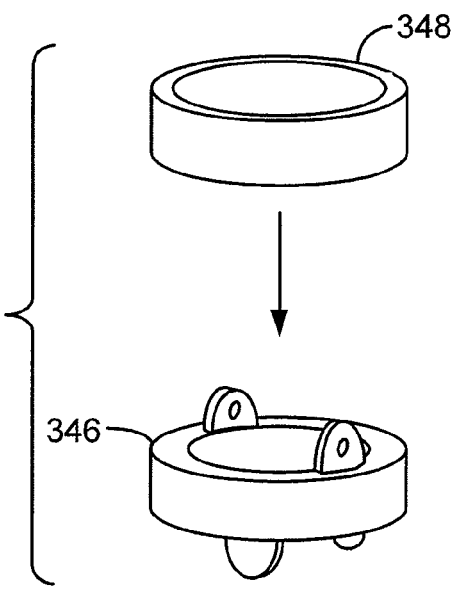
Figure 24C:
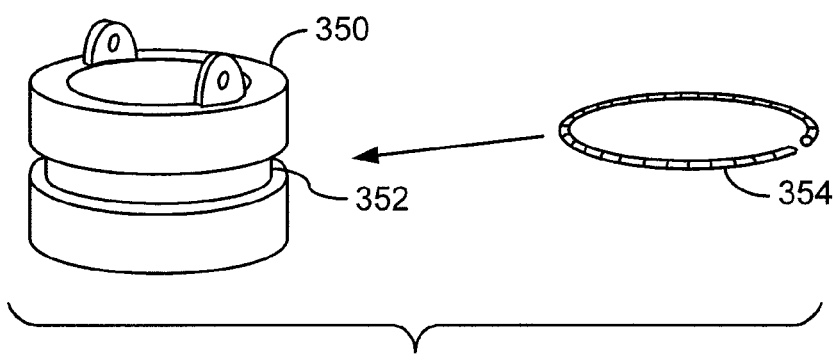

FIGS. 24A to 24C show perspective views of alternative variations for attaching permanent magnets, ferrous materials, or other materials that may alter or affect a magnetic field, onto individual vertebrae. FIG. 24A shows one variation in which vertebrae 340 may be manufactured with a notch or channel 342 circumferentially defined along its outer surface 344. A ring made of a ferrous material or other material that may alter or affect a magnetic field, such as permanent magnets, may be placed within notch 342. FIG. 24B shows another variation in which a formed ring 348 made of a permanent magnet or other such materials may be separately formed and attached onto vertebrae 346. FIG. 24C shows yet another variation in which a wire form 354 made from a ferrous material or other material that may alter or affect a magnetic field, such as a permanent magnet, may be placed within notch 352 of vertebrae 350. Alternatively, ferrous powder may be molded into a circumferential shape and placed within notch 352. Another alternative may be to simply manufacture the entire vertebrae from a ferrous metal or simply cover a vertebrae or a portion of the vertebrae with a ferrous coating.

Figure 25A:
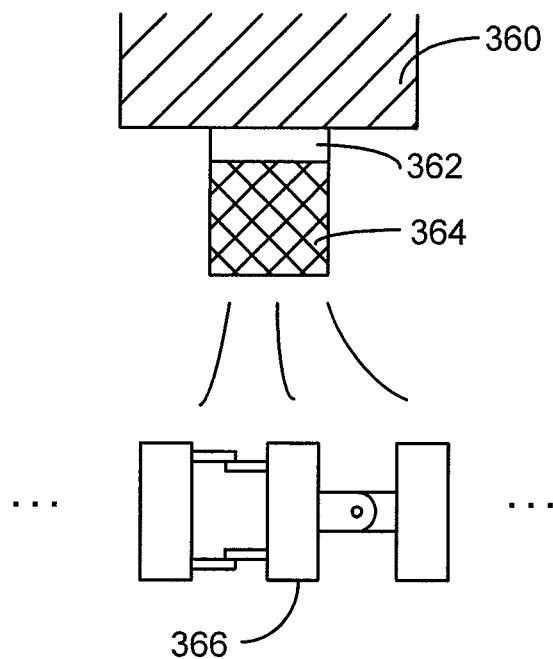
FIGS. 25A and 25B show examples of alternative sensing mechanisms using, e.g., force measurement.
Figure 25B:
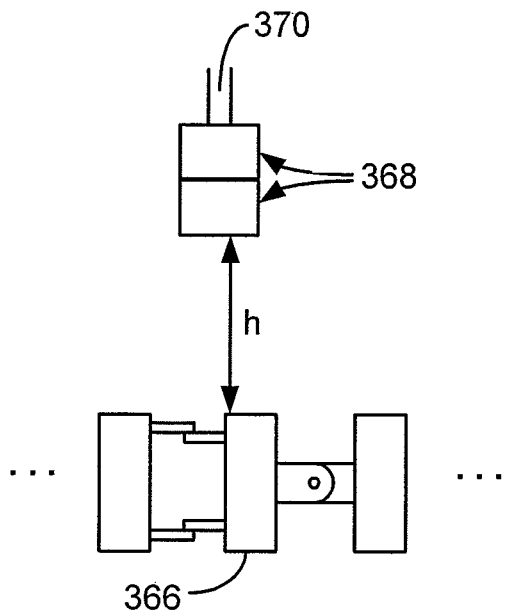

Another alternative for utilizing Hall sensors is seen in FIGS. 25A and 25B. The variation in FIG. 25A may have a fixed platform 360 upon which a magnet 364 may be mounted. A pressure sensor or microforce sensor 362 may be placed in between magnet 364 and platform 360. As an endoscope is passed adjacent to magnet 364, the magnet 364 may be attracted to vertebrae 366 as it passes adjacently. Vertebrae 366 may optionally include ferrous materials or other materials that may alter or affect a magnetic field as described above to enhance the attraction and/or repulsion. As magnet 364 is pulled or repulsed by the magnetic force, pressure sensor 362 may record the corresponding positive or negative force values for correlating to endoscope insertion depth. FIG. 25B shows another example in which magnets 368 may be attached to a pressure gauge 370, e.g., a Chatillon® gauge made by Ametek, Inc. As the endoscope passes magnets 368 at some distance, h, the attraction and/or repulsion between magnets 368 and vertebrae 366 may be accordingly measured by gauge 370 and similarly correlated to endoscope insertion depth.

Figure 26A:
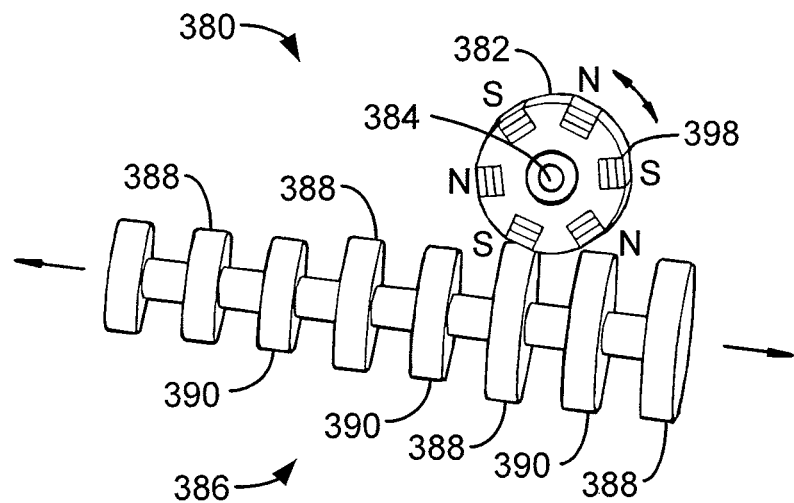
FIGS. 26A and 26B show another example of alternative sensing mechanisms using, e.g., a rotatable wheel having discrete permanent magnets or electromagnets integrated within or upon the wheel.
Figure 26B:
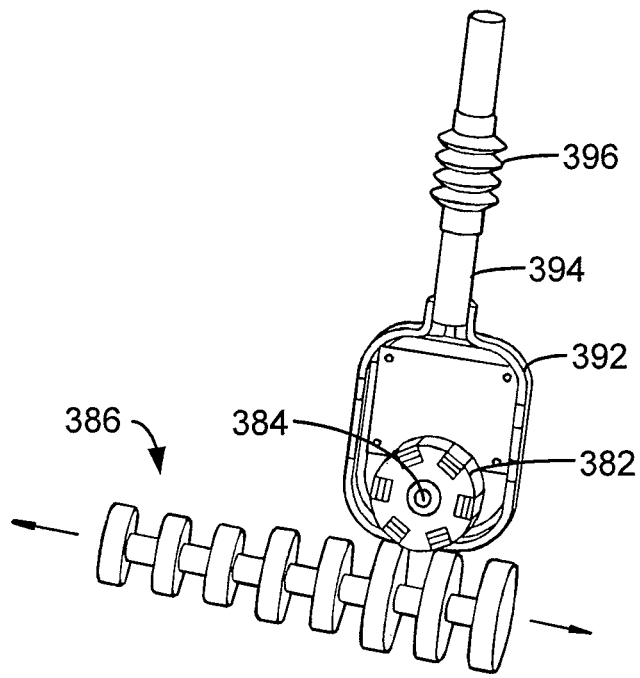

Yet another variation is shown in FIGS. 26A and 26B in assembly 380. Rather than utilizing the linear motion of an endoscope past a static datum, a rotatable datum 382 may be used to record insertion length. Datum wheel 382 may be configured to rotate about pivot 384 while sensing the movement of endoscope 386, which shows only schematic representations of the vertebrae for clarity. The datum wheel 382 may have a number of magnets 398 incorporated around the circumference of wheel 382. Each magnet may be arranged in alternating pole configurations or alternatively in the same pole arrangement. Each of the magnets 398 are also preferably spaced apart from one another at intervals equal to the linear distances between the magnets 388, 390 or permanent magnet located along the body of endoscope 386. Ferrous materials, or materials that may otherwise alter a magnetic field, may be used in place of the permanent magnets. As endoscope 386 is moved past datum wheel 382, wheel 382 rotates in corresponding fashion with the linear movement of endoscope 386 past the datum 382.

The rotation of datum wheel 382 that results when endoscope 386 is moved past can be sensed by a variety of methods. One example includes rotary optical encoders, another example includes sensing the movement of magnets 398 on datum wheel 382 as they rotate relative to a fixed point as measured by, e.g., Hall effect sensors or magnetoresistive sensors. As datum wheel 382 rotates with the linear movement of endoscope 386, datum wheel 382 may directly touch endoscope 386 or a thin material may separate the wheel 382 from the body of endoscope 386. FIG. 26B shows one variation of an assembly view of datum wheel 382 which may be rotatably attached to housing 392. Housing 392 may be connected to stem or support 394, which may extend from housing 392 and provide a support member for affixing datum wheel 382 to the patient, an examination table, a stand, or any other platform. Support 394 may also be used to route any cables, wires, connectors, etc., to housing 392 and/or datum wheel 382. The associated sensors and various support electronics, e.g., rotary encoders, magnetic field sensors, etc., may also be located within housing 392. Support 394 may further include an optional flexible joint 396 to allow datum wheel 382 to track the movement of endoscope 386 as it passes into or out of a patient.

Examples of External Sensing Devices

The external sensing devices, or datum, may function in part as a point of reference relative to a position of the endoscope and/or patient, as described above. The datum may accordingly be located externally of the endoscope and either internally or externally to the body of the patient. If the patient is positioned so that they are unable to move with any significant movement during a procedure, the datum may function as a fixed point of reference by securing it to another fixed point in the room, e.g., examination table, procedure cart, etc. Alternatively, the datum may be attached directly to the patient in a fixed location relative to the point of entry of the endoscope into the patient's body. The datum variations described herein may utilize any of the sensing and measurement methods described above.

For instance, for colonoscopic procedures the datum may be positioned on the patient's body near the anus. The location where the datum is positioned is ideally a place that moves minimally relative to the anus because during such a procedure, the patient may shift position, twitch, flex, etc., and disturb the measurement of the endoscope. Therefore, the datum may be positioned in one of several places on the body.

One location may be along the natal cleft, i.e., the crease defined between the gluteal muscles typically extending from the anus towards the lower back. The natal cleft generally has little or no fat layers or musculature and does not move appreciably relative to the anus. Another location may be directly on the gluteal muscle adjacent to the anus.

Figure 27:
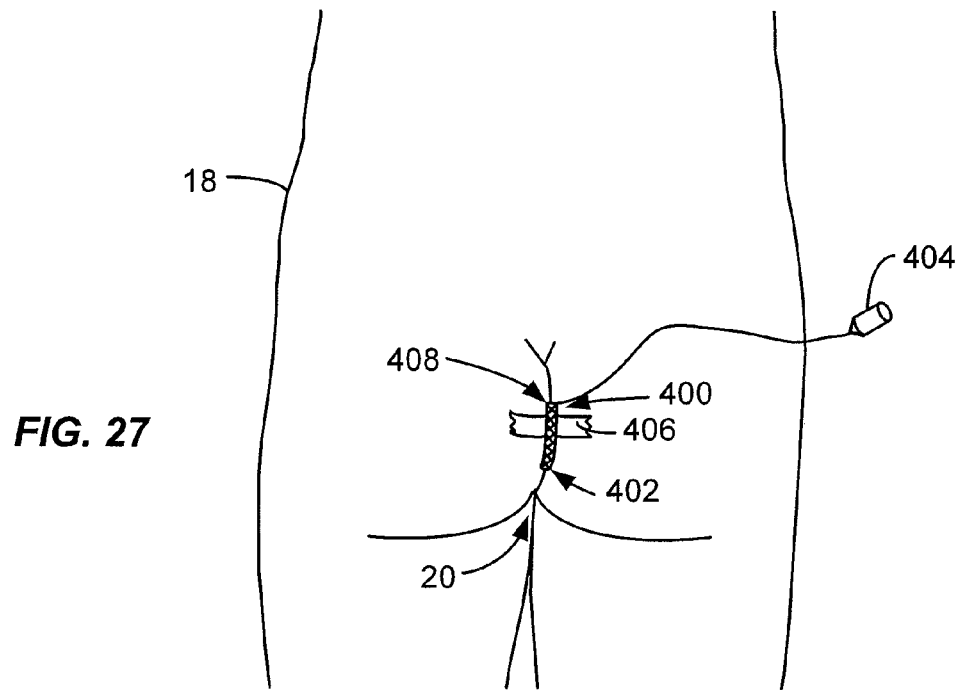
FIG. 27 shows one example of a datum which may be positioned along or within the natal cleft.

One variation for the datum for positioning along the natal cleft 408 is shown in FIG. 27. Datum 400 may have sensor 402 positioned in the distal tip of the sensing device, which may be placed adjacent to anus 20. The datum itself may be positioned within the natal cleft 408 and temporarily held in place on the patient with adhesive 406. The datum may have a connector 404 extending via a wire or cable for connection to a processor (not shown).

Figure 28:
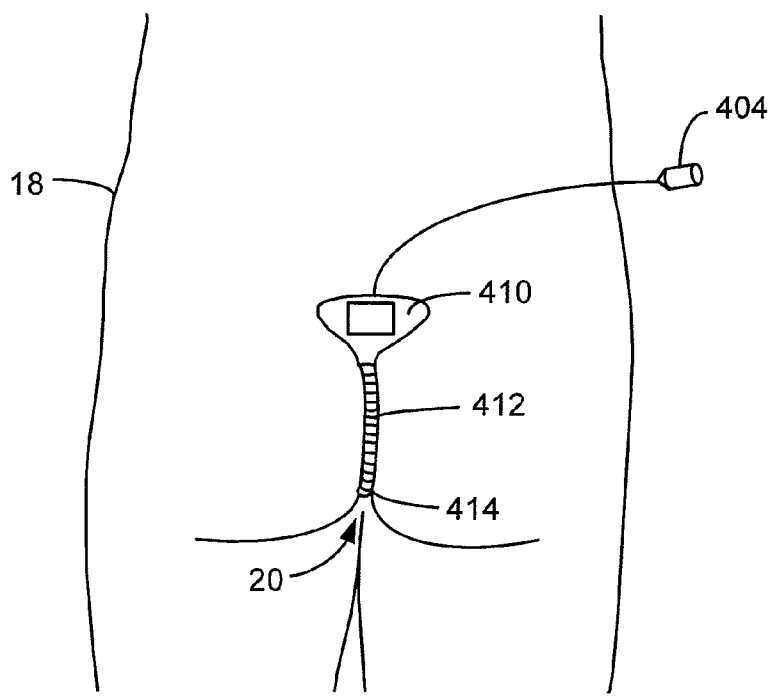
FIG. 28 shows another example of a datum which may also be aligned along or within the natal cleft using a flexible and elongate member.

Another variation is shown in FIG. 28 in which the datum 410 may have a base comprising a substrate. The substrate may have an adhesive side that may be placed against the small of the patient's back. An elongate flexible member or arm 412 may extend from the substrate and lie within or against the natal cleft such that the distal end 414 of member 412 is adjacent to anus 20. Distal end 414 may have a sensor mounted within for sensing the movement of an endoscope as it is passed through anus 20. The flexible member 412 may be secured along the natal cleft using, e.g., adhesive tape, to prevent excessive movement of the device.

Figure 29A:
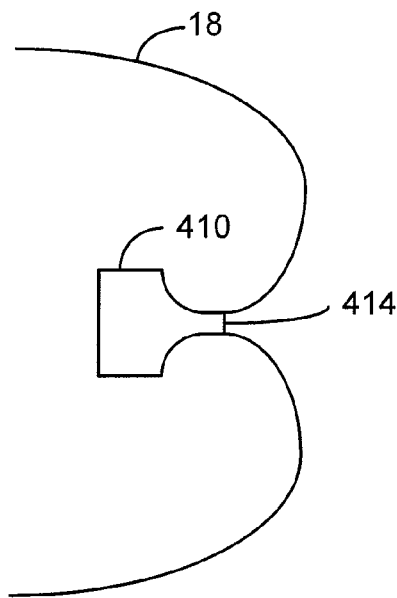
FIGS. 29A and 29B show one possible configuration for the datum sensor.
Figure 29B:
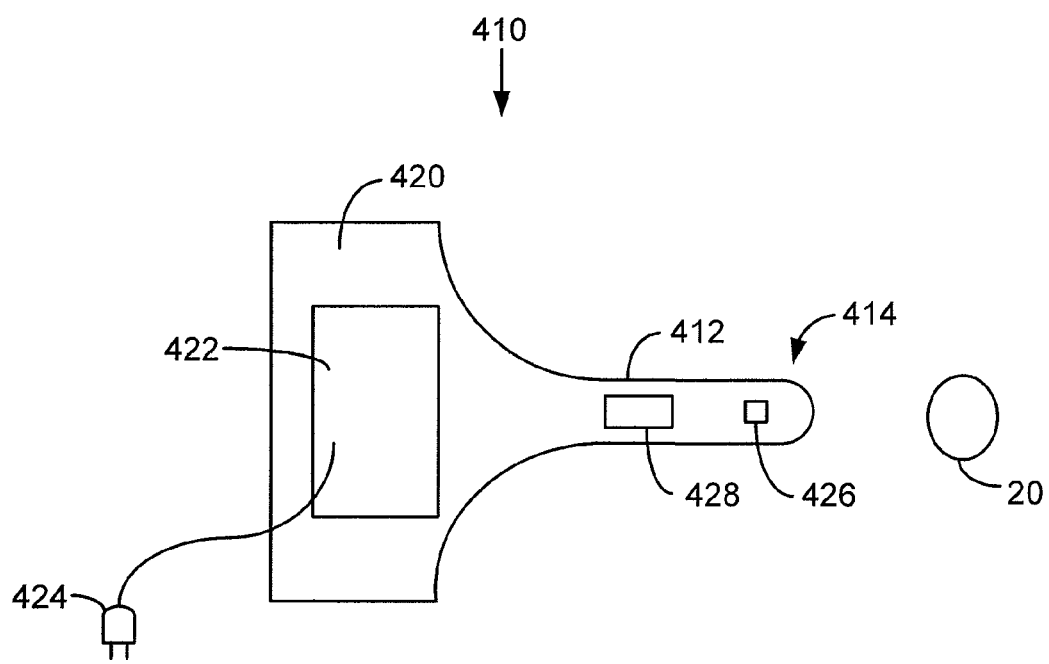

FIGS. 29A and 29B show a detailed view of a variation of the datum device 410 of FIG. 28. FIG. 29A shows another view for possible positioning of datum 410 on patient 18. The substrate may be positioned proximal of anus 20 while member 412 extends along the natal cleft for positioning sensor tip 414 proximally adjacent to anus 20. FIG. 29B shows datum 410 laid out and having a substrate 420 upon which sensors and electronics may be positioned. Substrate 420, as mentioned above, may have an adhesive backing for temporary placement against the patient 18. Moreover, datum 410, or any of the other datum examples described herein, may be optionally configured to be disposable for one-time use on a patient. Support electronics 422 may optionally be placed upon substrate 420 and sensor 426 may be positioned within the distal end 414 at or near the end of the flexible member or arm 412. An optional magnet 428 may be positioned along member 412 proximally of sensor 426. Connector 424 may extend via a wire or cable from datum 410 for connection to a processor.

Figure 30A:
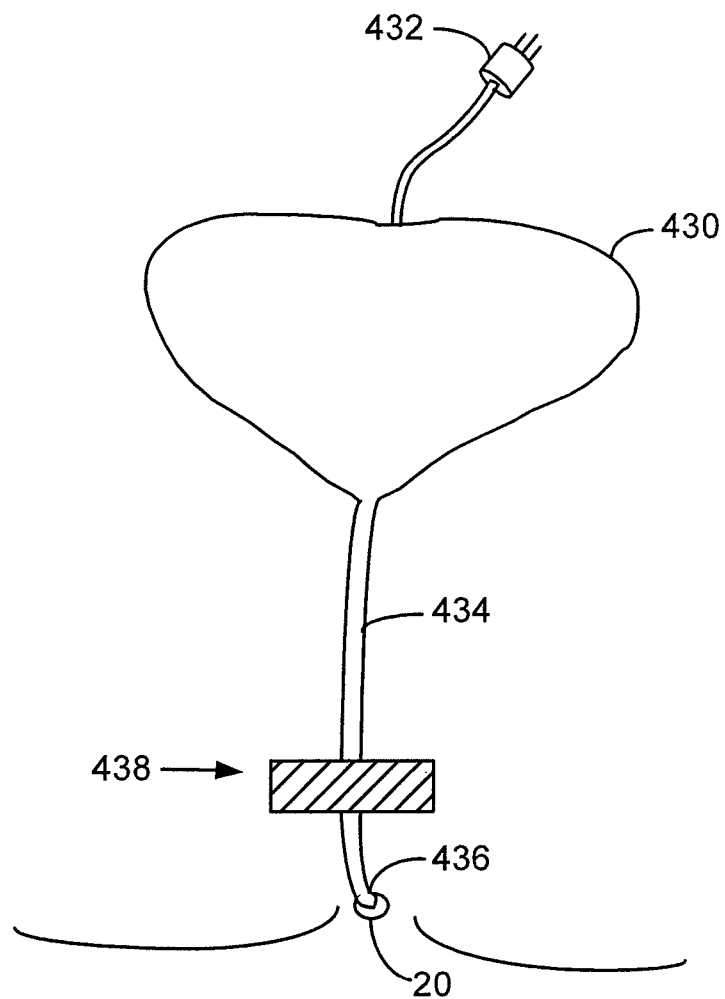
FIGS. 30 A and 30B show another example of datum positioning for securing the sensor to the patient.
Figure 30B:
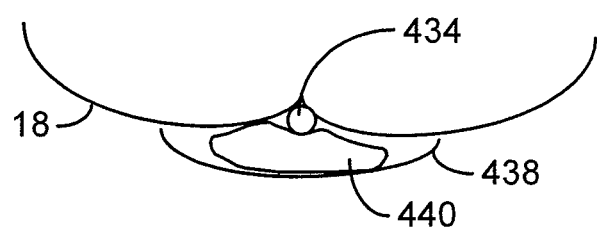

Another variation is shown in FIGS. 30A and 30B which shows datum substrate 430 having sensor 436 positioned within the distal end of elongate flexible assembly 434 for placement adjacent to anus 20. Connector 432 may be provided for connection to a processor. Here, elongate assembly 434 may be secured against or within the natal cleft by use of, e.g., an adhesive strip 438. FIG. 30B shows a cross-sectional top-down view of elongate assembly 434 positioned against the natal cleft. A sponge, silicone wedge, or some other wedging device 440 may be positioned inbetween elongate assembly 434 and adhesive strip 438 to ensure secure positioning of the datum device relative to anus 20.

Figure 31:
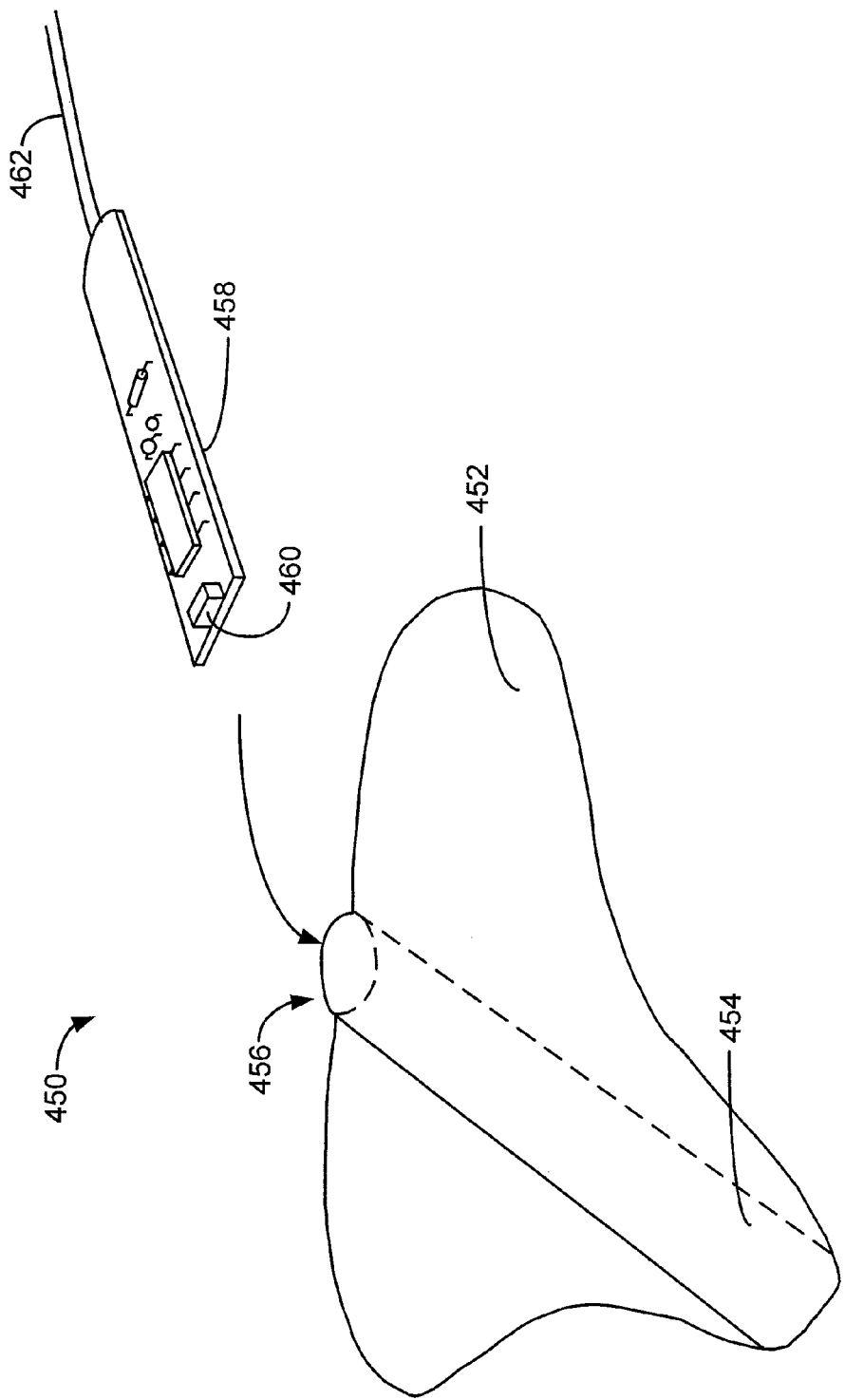
FIG. 31 shows another example of a datum for use with a sensor within a disposable substrate.

FIG. 31 shows another variation on the datum device which may utilize a disposable substrate. Datum assembly 450 may have substrate 452 for placement against the patient. A retaining pocket 454 may be defined within or upon substrate 452 and it may be configured to allow for a reusable electronic sensor assembly 458 to be placed within pocket 454. Sensor assembly 458 may have a wire or cable 462 extending therefrom and it may further have a sensor 460 positioned or potted upon sensor assembly 458. The sensor assembly 458 may be positioned within pocket 454 by slipping sensor assembly 458 through an opening 456 defined within substrate 452 and sensor assembly 458 is preferably positioned within pocket 454 such that sensor 460 is positioned at the distal end of substrate 452 to allow for positioning adjacent the anus.

Figure 32A:
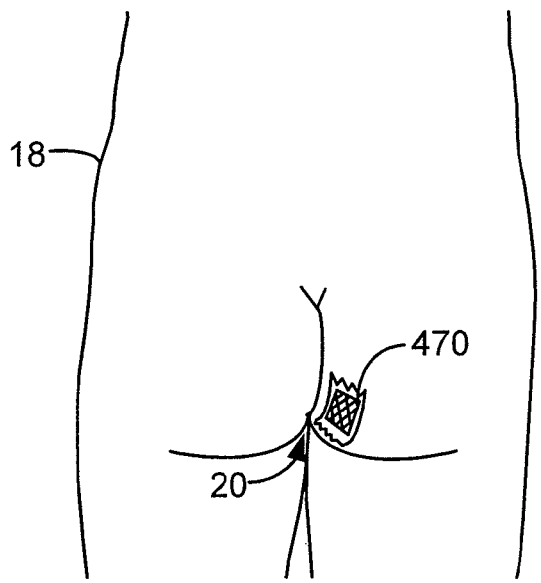
FIGS. 32A and 32B show another example of a datum which may be positioned on a single cheek adjacent to the anus.
Figure 32B:
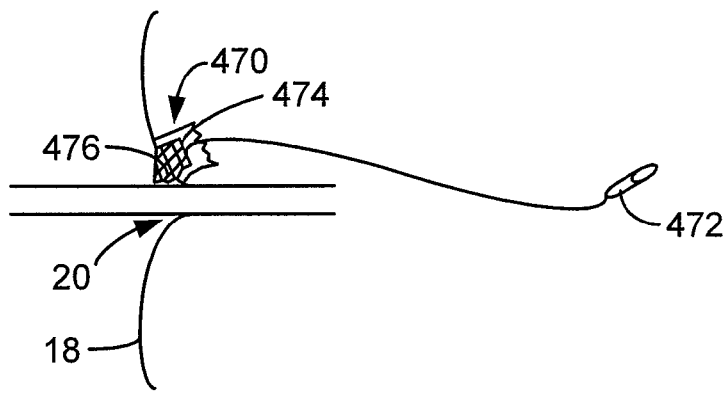

Another variation for positioning a datum is directly on the gluteal muscle adjacent to the anus. Generally, the sensor and associated circuitry may be incorporated into a patch or small chassis that may then be attached to the muscle adjacent to the anus. The entire datum assembly may optionally be mounted onto a bandage-like package with an adhesive backing. FIGS. 32A and 32B show a variation in datum 470 which is formed into a small chassis having connector 472 extending therefrom. Datum 470 may be attached temporarily to patient 18 via adhesive 474 adjacent to anus 20. A guide, ramp, or other similar structure 476 for situating, orienting, or guiding endoscope relative to datum 470 may be optionally incorporated into the device.

Figure 33A:
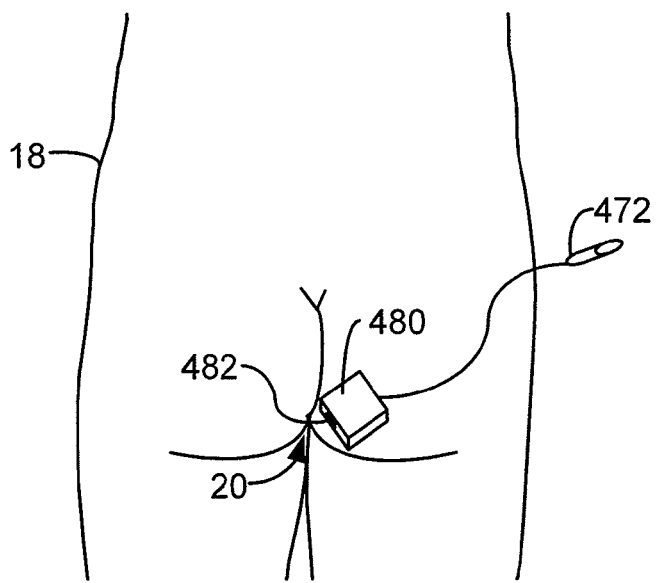
FIGS. 33A to 33C show another example of a datum which may also be positioned on a single cheek adjacent to the anus.
Figure 33B:
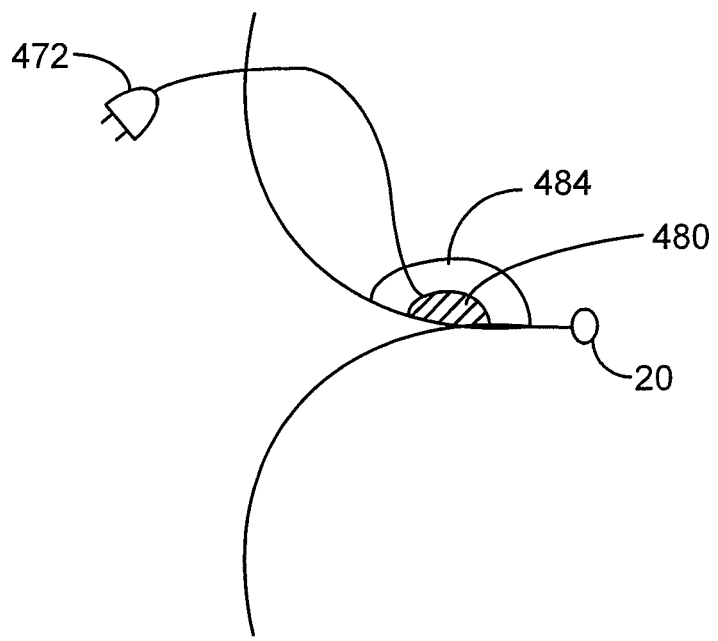
Figure 33C:
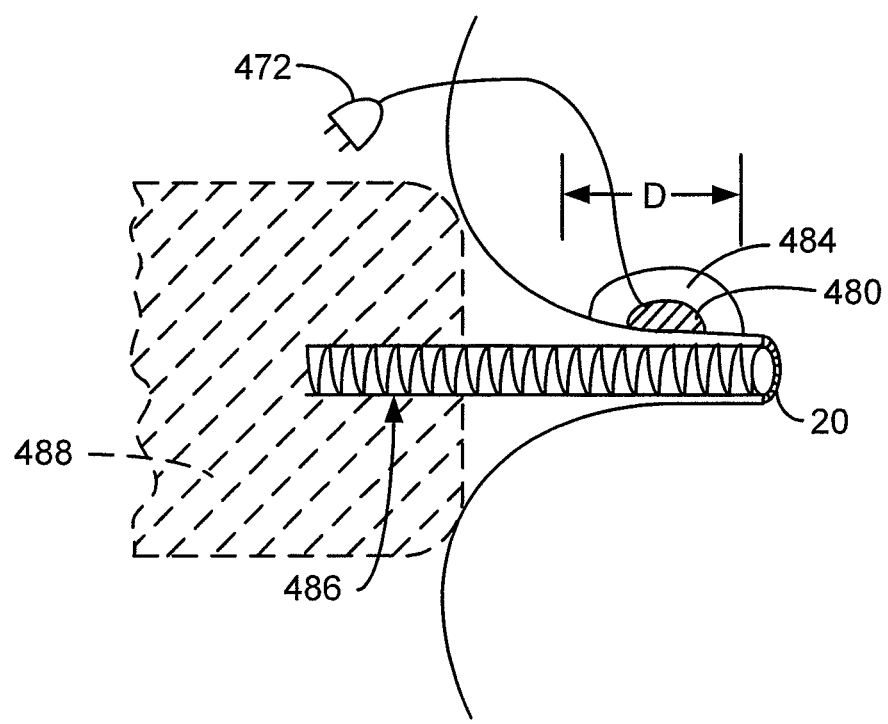

FIG. 33A shows another variation of the device in datum 480. In this example, datum 480 may be in the form of a patch with sensor 482 positioned thereon. The device may be placed upon one of the gluteal muscles such that sensor 482 is adjacent to anus 20. FIG. 33B shows a detailed view of how datum 480 may be positioned upon the gluteal muscle adjacent to anus 20. Adhesive 484 may be placed over datum 480 to temporarily hold it onto the gluteal muscle as shown. FIG. 33C shows an example of how datum 480 may interact with endoscope 486 as it is advanced or withdrawn from anus 20. Because datum 480 may have a relatively small diameter, D, discomfort may be reduced for the patient and close proximity to anus 20 may be assured. As endoscope 486 moves past datum 480, the sensors within datum 480 may measure the insertion depth. Zone 488 shows generally the zone of operation, i.e., the region within which the operator's or surgeon's hands generally operate during a colonoscopy procedure. Because of the small diameter of datum 480 and its position adjacent anus 20, it is generally out of the way of the operator or surgeon during a procedure and thereby allows for unhindered operation of the endoscope 486 while maintaining accurate measurement or sensing with datum 480.

Figure 34:
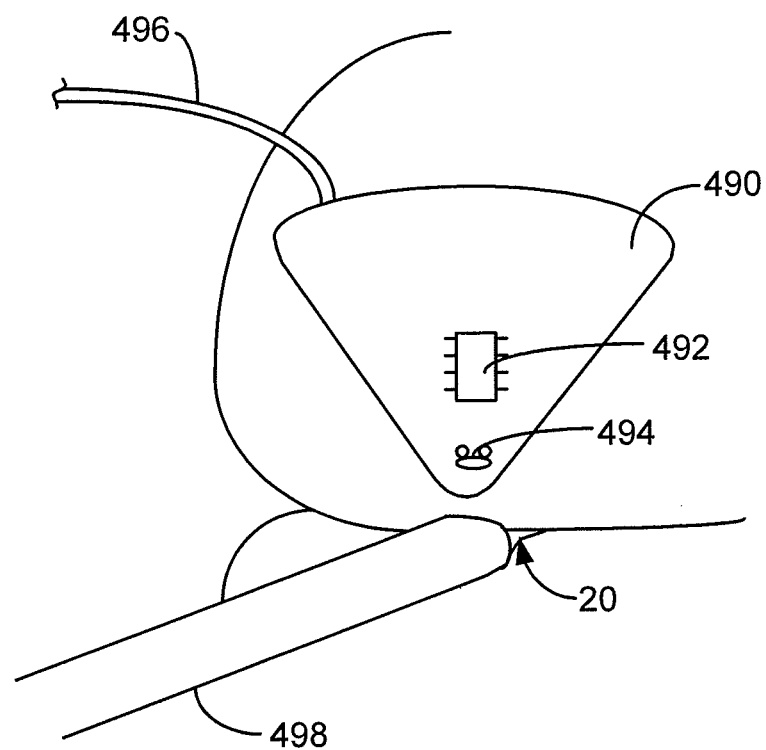
FIG. 34 shows yet another example of a datum which may also be positioned on a single cheek adjacent to the anus.

FIG. 34 shows yet another variation in datum 490 which may have a substrate with sensor 494 mounted at one end. Support electronics 492 may be optionally mounted on datum 490 and wire or cable 496 may be used to transmit the measured signals from sensor 494. Datum 490 may be in a triangular shape for placement upon a single gluteal muscle, as shown, such that a vertex of the substrate is positioned adjacent to anus 20 to allow sensor 494 to sense or measure signals as endoscope 498 is advanced or withdrawn into anus 20. Although shown in this variation in a triangular pattern, this is not intended to be limiting and is intended merely to illustrate one possible shape for the datum.

Figure 35:
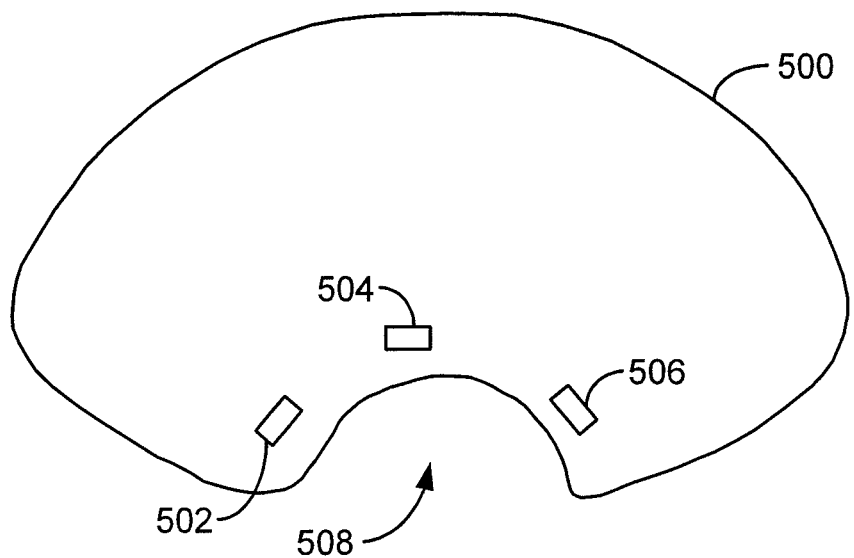
FIG. 35 shows yet another example of a datum having multiple sensors which may also be positioned on a single cheek adjacent to the anus.

Another variation is shown in FIG. 35 in which datum 500 may incorporate multiple sensors. Datum 500 may be placed on a single gluteal muscle and it may define an insertion region 508 at which the anus of the patient may be positioned. Each of the sensors 502, 504, 506 may thereby be configured to sense or read the endoscope as it passes through or past the insertion region 508. Although three sensors are shown in this configuration, fewer or more sensors may be utilized depending upon the configuration of the datum 500 and the desired signal processing results.

Figure 36:
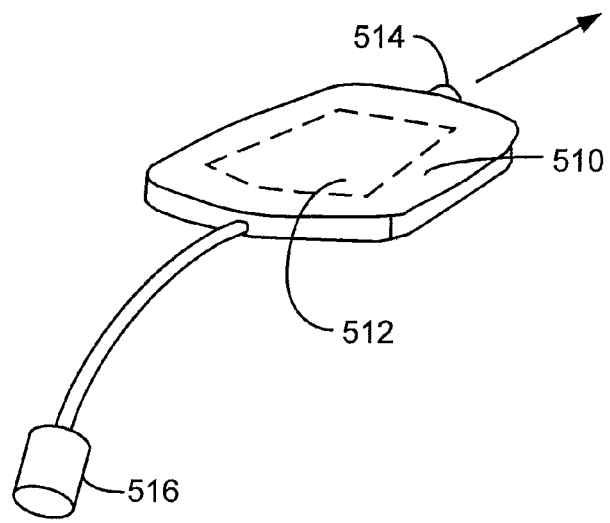
FIG. 36 shows an example of an encased datum.

FIG. 36 shows yet another variation in which datum 510 may be encased in a rigid housing. Datum 510 may thus encapsulate support electronics 512 within with sensor 514 directed towards one end of the housing. The housing may incorporate a connector 516 attached via a wire or cable extending from the datum 510. The rigid housing may be temporarily adhered to the patient on a gluteal muscle in the same fashion as described above.

Figure 37:
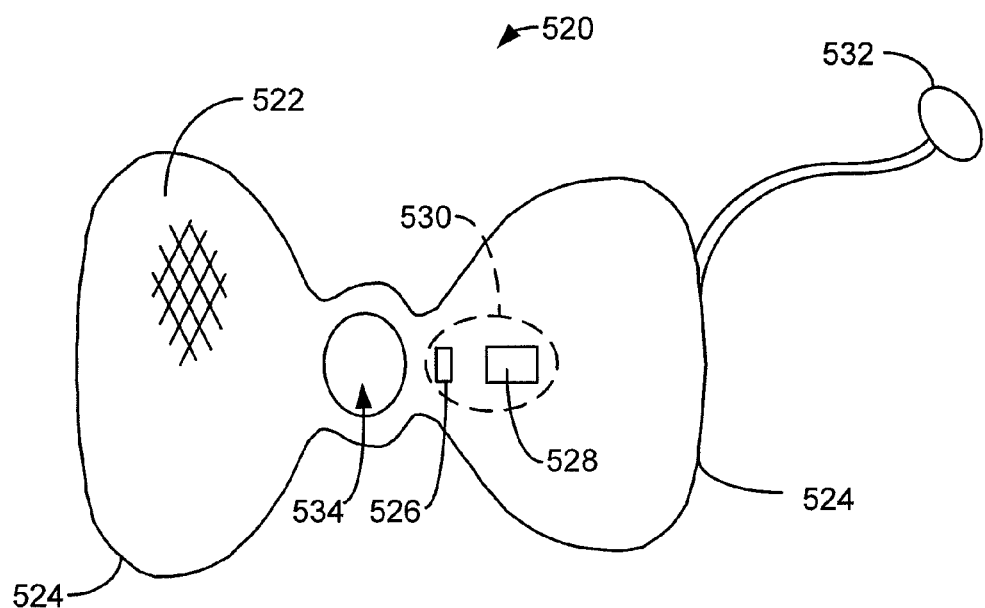
FIG. 37 shows an example of a datum which may be placed upon both cheeks while spanning the natal cleft.

FIG. 37 shows yet another variation in which datum 520 may be configured to extend across the natal cleft to position an opening defined in the datum over the anus of the patient. As shown, an adhesive substrate 522 may be configured, e.g., into a "butterfly" configuration. Substrate 522 may have at least two wings or flaps 524 for adhering to each gluteal muscle across the natal cleft while sensor 526 and support electronics 528 may be contained adjacent an opening 534 defined at or near the center of substrate 522. Sensor 526 and support electronics 528 may be potted or contained within a housing 530 on substrate 522. Connector 532 may be attached via a wire or cable for connection to a processor.

Figure 38A:
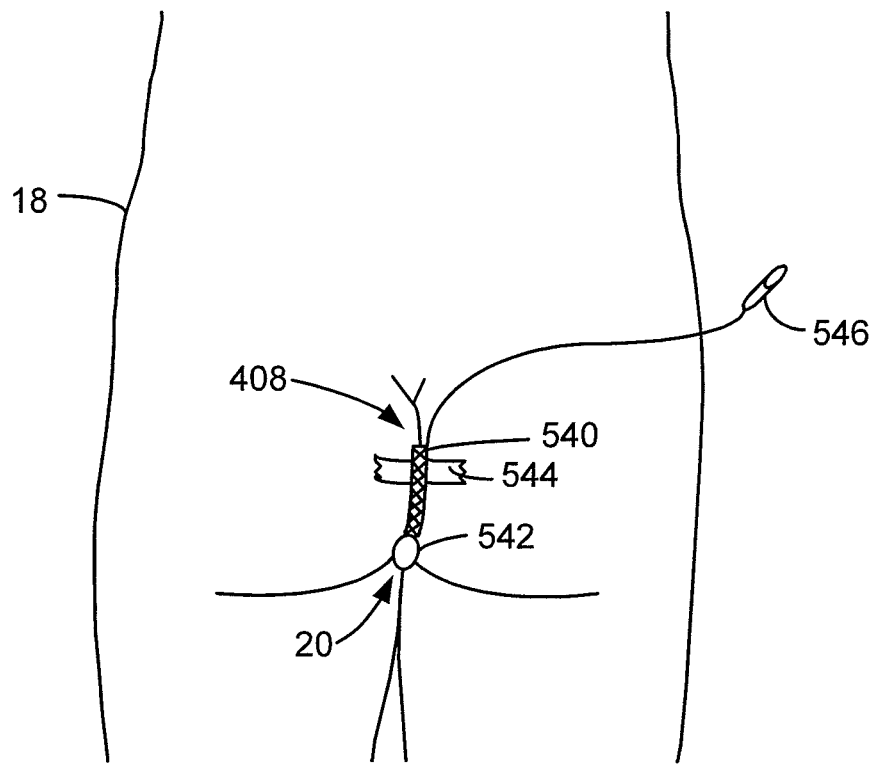
FIGS. 38A and 38B show an example of a datum which may be used to encircle the endoscope when in use.
Figure 38B:
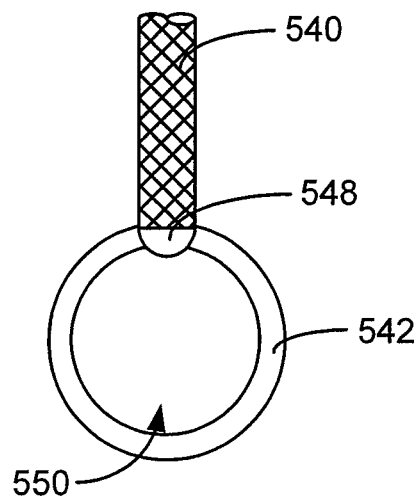

A datum device may also be configured to encircle an endoscope as it passes into the body. Such a datum configuration may be useful when using sensing technology such as RF. In the case of RF, the datum may be in a looped configuration to facilitate the exchange of RF signals with components or sensors mounted along the endoscope, as described above. One variation of a looped datum configuration is shown in FIGS. 38A and 38B. As shown, datum 540 may have a loop 542 defined at a distal end to function as a signal receiver, e.g., RF signals, and/or as a guide loop. The datum 540 may be aligned along the natal cleft 408 and secured in place with adhesive tape 544. A connector 546 may be attached to datum 540 via a wire or cable at a first end of datum 540 while sensor 548 may be positioned at the opposing end of datum 540. Sensor 548 may be positioned adjacent to anus 20, while loop 542 encircles the opening of anus 20. The loop 542 may define an insertion region 550 through which an endoscope may be passed. The loop 542 may be made of a thin, flexible material such as mylar and it optionally have an adhesive backing for placement upon the tissue surrounding anus 20. Although shown in a circle configuration, loop 542 may be in a variety of looped configuration and is not limited by its shape.

Figure 39:
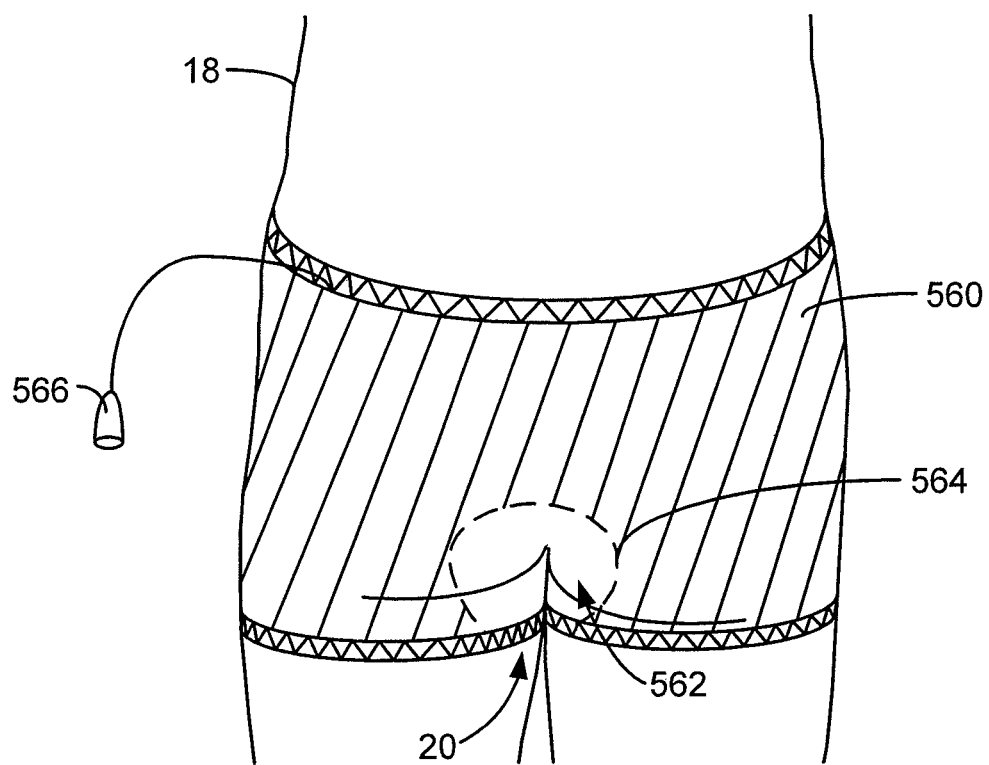
FIG. 39 shows an example of a datum which may be incorporated into the fabric of an undergarment in the region surrounding the anus.

Yet another variation is shown in FIG. 39 where a supporting garment 560, e.g., a pair of underpants, may define an opening 562 in the region surrounding the anus 20. A loop 564 may be incorporated into the fabric such that the loop surrounds the opening 562. The fabric in the middle of loop 564 may either be removable at the time of the procedure or omitted altogether. Connection to the loop 564 may be made through connector 566, which can be connected via a wire or cable extending from, e.g., the waistband, front, or side of garment 560.

Aside from colonoscopy, other applications may include uses in minimally invasive surgery (MIS). MIS typically depends upon the use of long, thin tools for insertion into the body via small incisions, e.g., often through a cannula. Instruments typically employed during MIS may include rigid endoscopes, laparoscopes, thoracoscopes, needle drivers, clamps, etc. Because each of these tools must pass through an opening in the body, a datum device may be used adjacent to that body opening for tracking instrument insertion depth. In situations where cannulas are used, the cannula itself may be instrumented through one of the methods described above.

For other types of endoscopy procedures, various types of flexible endoscopes may be used, e.g., upper endoscopes, duodenoscopes, sigmoidscopes, bronchoscopes, neuroscopes, ENT scopes, etc. Any of the devices and methods described above may be utilized and configured to maintain insertion depth for any of these types of endoscopes. For instance, for flexible endoscopes that enter the body transorally, a mouthpiece configured as a datum may be utilized.

In another embodiment of the present invention, there is provided an instrument, system and method for the use of RFID technology to the sensing of position. A series of RFID tags are affixed to an object that passes in close proximity to an RFID reader & antenna. The passage of the series of RFID tags allows the position of the object to be determined by identifying the RFID tags that respond to queries by the reader.

Specifically, one application of this concept relates to sensing the depth of insertion of a flexible endoscope into a patient during an endoscopic procedure. This application describes an application specific to colonoscopy. The techniques, methods, components and systems described herein may be used with any flexible endoscope and any endoscopic procedure. Other related concepts are described in U.S. patent application Ser. No. 10/384,252 published as U.S. Patent Application No. 2004/0176683, which is incorporated herein by reference in its entirety.

There are 4 major families of RFID technologies, categorized by their operating frequencies:
1. Low frequency (LF): 125 kHz-135 kHz
2. High Frequency (HF): 13.56 MHz
3. Ultra-High Frequency (UHF): 868 MHz-928 MHz
4. Microwave: 2.45/5.8 GHz The embodiments described herein may be implemented within any of the above listed RFID families. HF RFID has the following advantages:
1. operates at frequencies that are not highly absorbed by water or living tissue
2. mature technology with many readily available components
3. compact components
4. high read rates (<0.25 s)
5. anti-collision (multiple RFID tags may be read simultaneously)

Other RFID families share some of these advantages; however HF is the only family that combines them all at the same time. The primary advantage of microwave RFID is the relatively small size of the RFID chip. The Hitachi µ-chip, for example, is about 0.4 mm×0.4 mm. This size allows the chip to be placed in nearly any location along, within or about an instrument.

RFID tags, readers and antennas are well known and widely commercially available. A typical RFID (Radio Frequency Identification) system is comprised of 4 basic elements: (1) RFID reader module; (2) RFID reader antenna, (3) RFID reader antenna cable and (4) RFID tag, chip or sensor.

RFID Reader Module

The RFID reader module is the source of the RF carrier wave used both to provide power to responding RFID tags, and to create the base carrier over which RF communications are achieved. The reader module can be off-the-shelf module such as the OBID® RFID Reader System provided by FEIG Electronic GmbH located in Weilburg, Germany or the Skyemodule M1 provided by SkyeTek, Inc. located in Westminster, Colo. The reader may include an anti-collision mechanism that allows for the orderly processing of responses from two or more RFID tags within the reader field range. Reader modules may be designed from conventional modular components or custom designed. Typically RFID readers are configured to operate with RFID tags that comply with ISO-15693, ISO-14443 and HF EPC, for example. Readers have a read range based on a number of factors such as antenna type (internal vs. external), surrounding structure that may interfere with operation and operating frequency. For example, an HF RFID reader may have a read range or reader field range of 9 cm with an internal antenna or 20 cm with an external antenna. In another example, a microwave RFID reader may have a reader field range of 1 m or more. Embodiments of the present invention utilize the entry and departure of individual RFID tags from a reader field range to determine the position of an instrument.

RFID Reader Antenna

The RFID reader antenna is the antenna used to broadcast the RF carrier wave created by the RFID reader module, and to receive the signal created by the RFID tag. The antenna is selected based on the operating frequency for the RFID system.

RFID Reader Antenna Cable

The RFID reader antenna cable is a conventional wired connection between the reader module and the reader antenna, typically impedance matched.

RFID Tags

An RFID tag is a conventional transponder that is excited and queried by an appropriate RFID reader assembly based on the operating frequency of the RFID system in use. RFID tags are passive ICs that receive power from the RF signal from the reader and generate electric power from the received RF signal. The RFID tag then transmits its ID or data to the reader. The response of a typical RFID tag may include but is not limited to: tag serial number, tag data field, placement within an item (i.e., distance from the distal end of an instrument or placement about the perimeter of an instrument) and/or sensor inputs. A typical RFID tag is comprised of an RFID integrated circuit (chip), an antenna, and discrete electronic components (e.g. inductors, capacitors, resistors, etc.). RFID tags are also referred to as short range contactless memory chips. Numerous various chips are commercially available and manufactured by STMicroelectronics of Geneva, Switzerland, among others. Another RFID IC is the µ-chip provided by Hitachi, Ltd., Japan. The RFID tag and reader may also be programmed to provide a number of other features such as: anti-clone, authentication, unique ID, and/or challenge/response. RFID tags may also include writable memory. One use of the writable memory would be to write the position orientation or other position information onto a specific tag as the instrument is assembled or as part of a tag initiation process. In this manner, the unique identification of a tag may be associated with a position on, in or about an instrument or component of an instrument. One exemplary write application would be to write onto tag memory the location of the tag relative to the distal end of the instrument. The write process may also include information related to the orientation of the tag on a portion of the instrument. Exemplary orientations may include 0, 90, 180 or 270 degree relative positions on a component of the instrument such as a vertebra or other structural member.

Figure 42A:
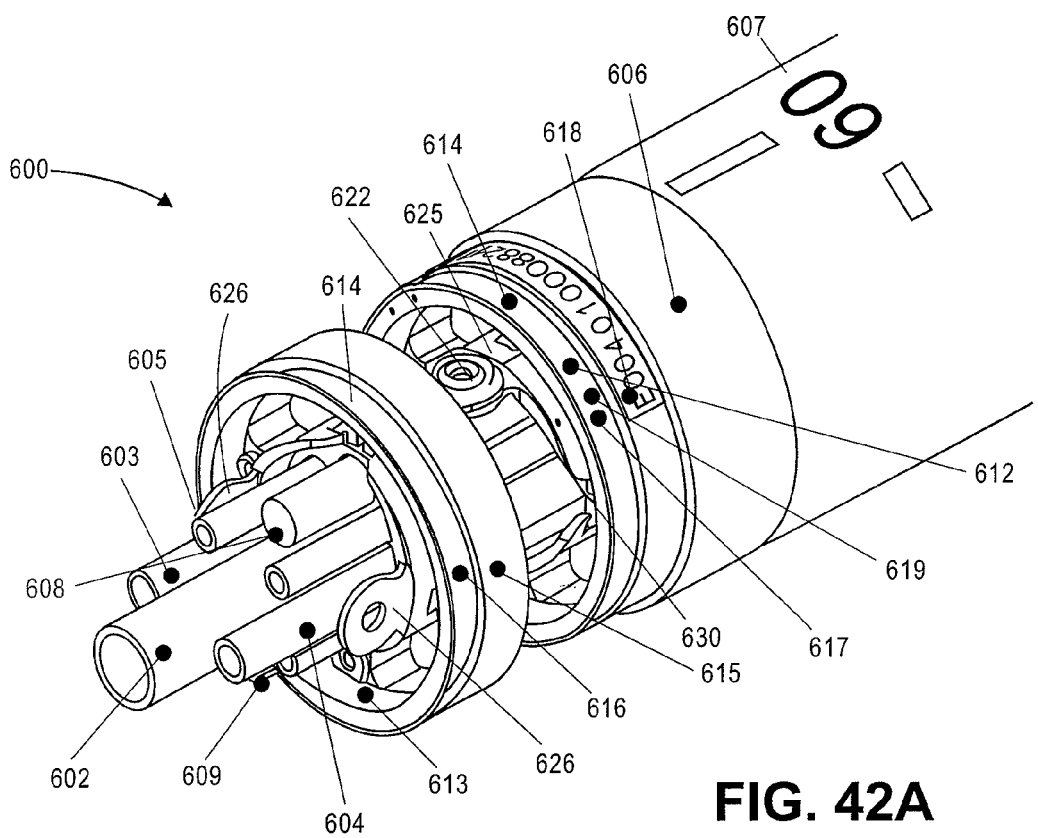
FIGS. 42A and 42B illustrate perspective and end views, respectively, of a segmented instrument having RFID tags located on each segment.
Figure 42B:
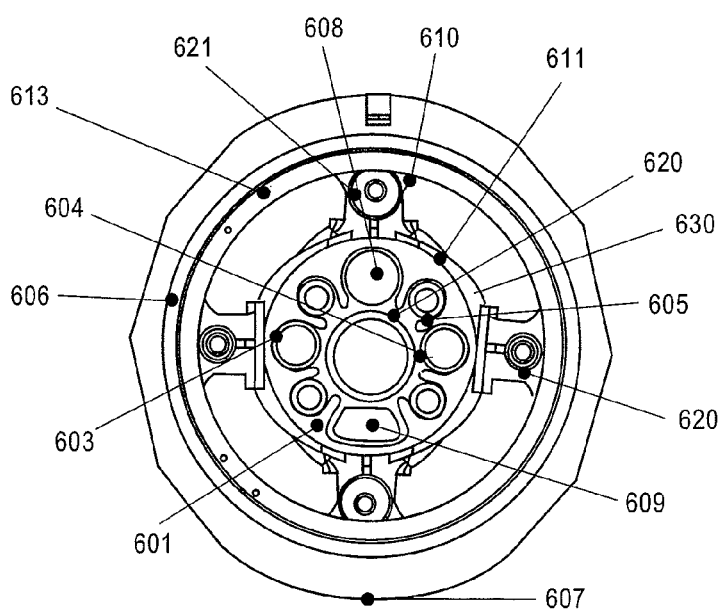

A plurality of RFID tags are provided on, in, about or along an instrument. FIGS. 45, 46, 47, and 41 provide non-limiting examples for various placement arrangements on, about or along an instrument. Additional specific but non-limiting examples of RFID tag placement include:
  a. RFID tags that are built into, or added onto, a articulating vertebra or other structural member of an instrument.
  b. RFID tags that are constructed into a stand alone structure that is then added-onto the structure of or a component of an instrument. One example is the RF bobbin illustrated in FIGS. 43A and 43B. As illustrated, the RFID IC and antenna is fabricated into a hoop that then slides over an exiting structural component of an instrument. FIGS. 42A and 42B illustrate the RF bobbin in FIGS. 43A and 43B in place on two hinged segments of an instrument.
  c. RFID tags may be placed in a variety of positions relative to the segments or sections of an instrument.
    i. The RFID tag may be placed inside or formed within a segment or section ring.
    ii. The RFID tag may be placed outside of a ring such as within the instrument skin or outer barrier that covers the instrument. The RFID tag may be placed on, in or along a component between instrument structure and instrument skin such as the mesh or tube sleeve 606 illustrated in FIG. 42A. Strips of RFID tags (such as a plurality of µ-chips for example) may be located in various positions along or about the instrument as illustrated in FIGS. 44, 41, 40, 45, 46, and 47.
  d. The number and placement of RFID tags on an individual vertebra, segment or structural element include, without limitation:

i. One RFID tag per vertebra ii. Multiple RFID tags per vertebra or other structural component of an instrument iii. One tag per multiple vertebrae, segment or section.

In addition to providing a number of RFID tags on, in, along or about an instrument, it is to be appreciated that different function and types of RFID tags can be used, such as, for example:

a. LF, HF, UHF, or microwave operating frequency.

b. More than one tag per vertebra or per structural component of an instrument.

c. RFID tags that respond only with their serial number ("bar code" style) in circumstances where no other storage or reporting of data is possible.

d. RFID tags may provide bar code plus other parameter, e.g., rotational position or "torque", switch open/closed, temperature, etc.

e. RFID tags may be used to help determine scope shape and/or position or other descriptors. Other exemplary functions include triangulation of RFID tag position, based on signal strength for example, including RFID for triangulation to determine position and/or rotation of scope f. Advanced technology and compact design RFID chips such as the p-chip or the so called "grain of sand" RFID tags from Hitachi, Ltd.

In some embodiments, the reader antenna is designed in the form of a "patch," or a flexible substrate or structure (see, for example, FIGS. 27-39, 48, 49, and 50) that supports the reader antenna and provides an aperture sized to receive an instrument. The substrate may include an adhesive backing so that it may be affixed to a surface while in use. One exemplary use is that the flexible substrate is affixed to a patient near the point of entry into the body. At least one RFID tag may be used near the antenna (i.e., within the reader field range) for anti-cloning or anti-counterfeiting functions and to continuously verify function of the reader module. A plurality of RFID tags may be provided on or in the instrument to assist in determining, for example, the depth of insertion of the instrument, instrument function and/or performance.

Figure 48:
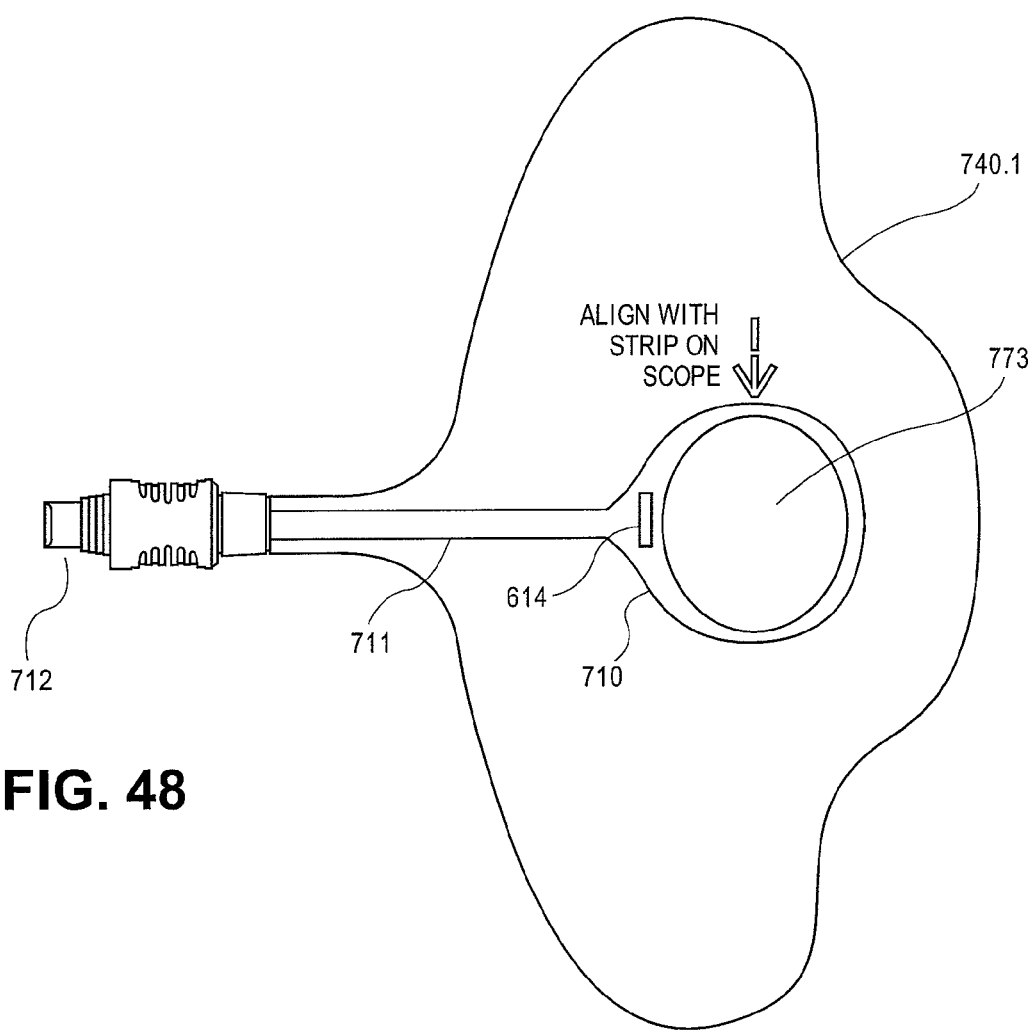
FIGS. 48, 49 and 50 are perspective views of alternative embodiments of flexible substrates used to support a reader antenna and RFID tag.
Figure 49:
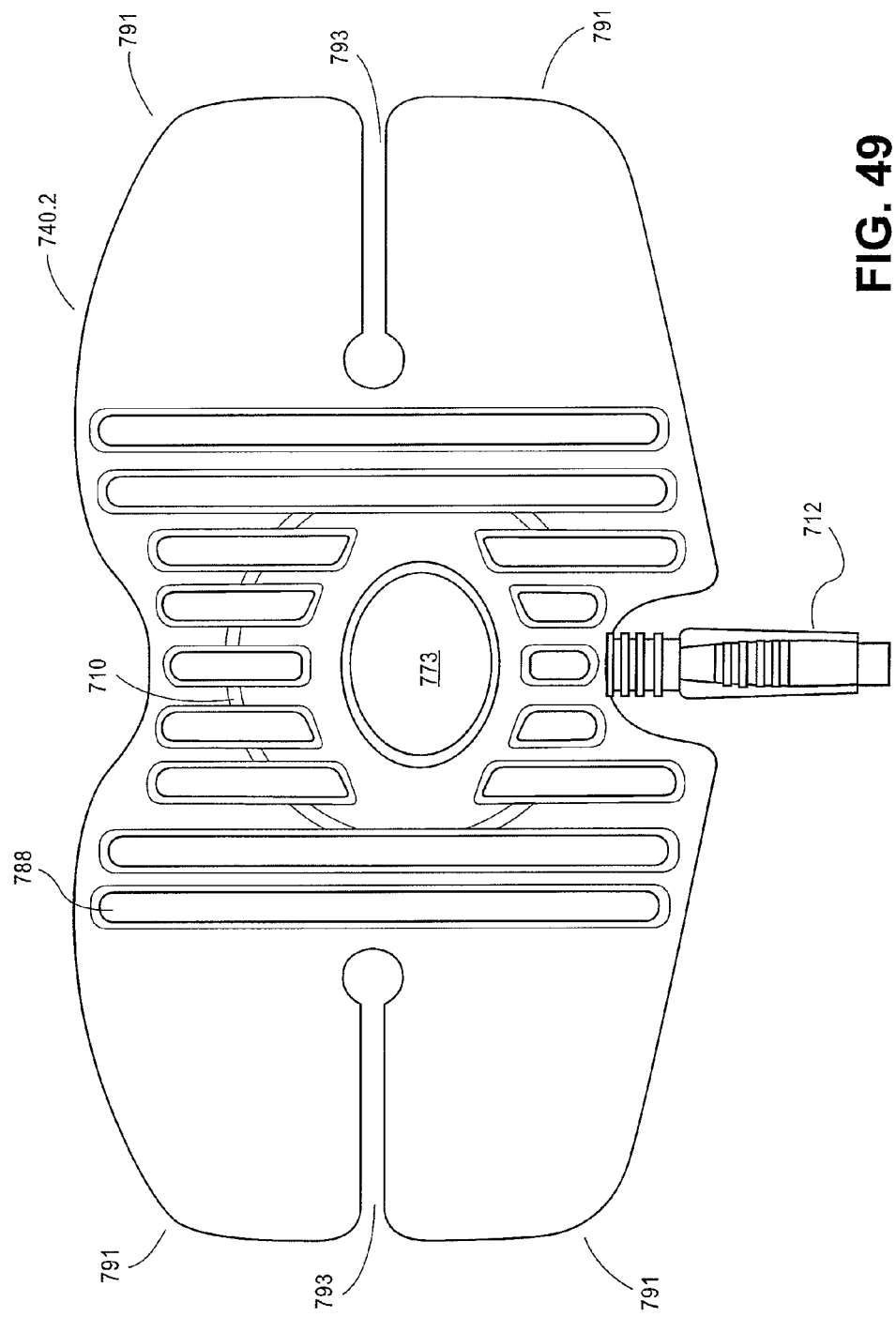
Figure 50:
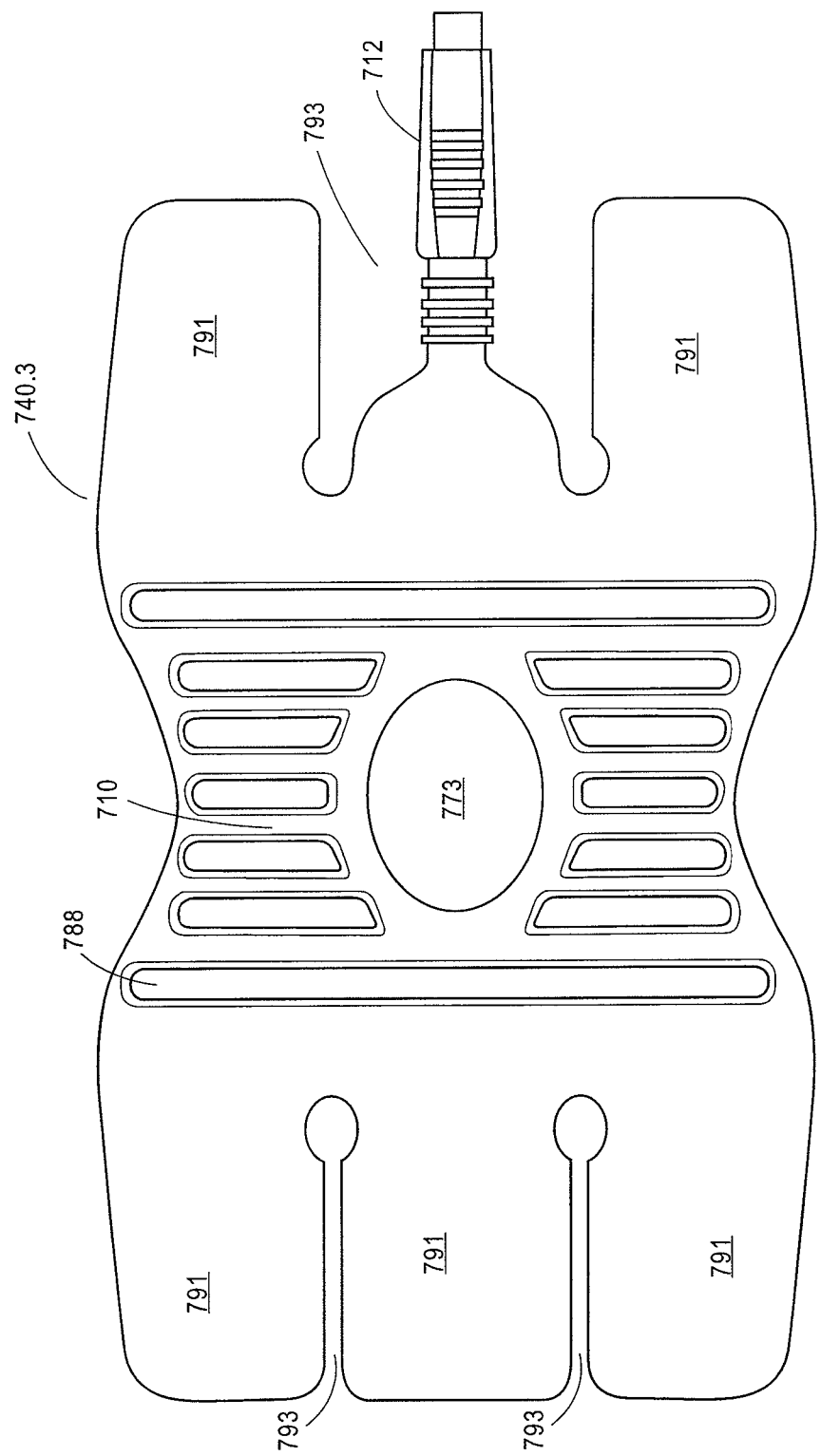

An RFID reader antenna may also optionally be provided with an RFID tag built into or located near the antenna. Many details of various reader antenna alternatives are illustrated in FIGS. 48, 49 and 50. One benefit of placing an RFID tag that remains within the reader field range is that the reader will always see one "known good" tag. The ability of the reader to be able to query a known tag may be used to verify system operation or to authenticate an antenna assembly (i.e., the antenna patch, see FIGS. 27-34 adapted for RFID applications and FIGS. 48, 49 and 50). The "known good" tag may also be used to confirm the RFID positioning system is functioning properly.

The system described herein provides a programmable device that is manufactured as part of a single-use medical device for the purpose of determining calibration, manufacturer, operator and other information. These functions are accomplished without a conventional wired interface. Instead, these functions are accomplished using a radiofrequency interface provided by the reader antenna and the RFID tag for real time device operation or performance monitoring. Additionally, the use of a "known good" tag provides an operational check of RFID reader antenna circuitry to verify integrity of the cable and antenna.

Another feature is an anti-counterfeiting or anti-clone feature: An RFID tag may be assigned a code unique to the system. System software could be require identification of a "recognized" tag prior to operation of the system. An embedded RFID tag in the flexible antenna substrate may be used to prevent counterfeiting and ensure that the device remains a single-use medical device. Counterfeiting is prevented or discouraged because of the unique code that can be programmed into the memory of the RFID tag thereby making the single-use medical device difficult for others to copy.

In order to prevent counterfeiting, an RFID tag integrated circuit and antenna may be fabricated into a single-use device. The single use device has an integrated RFID antenna. When connected to an RFID reader, the RFID antenna can read tags in the vicinity as well as the integrated tag. Software inside the RFID reader will perform a check of the single-use device by reading the RFID tag to ensure the attached single-use devices in genuine. If a known RFID tag is not read, the software will prevent use of the single-use device. In addition, the RFID tag embedded the antenna serves as an indicator that the RFID reader antenna is connected to the RFID reader. When the RFID reader is unconnected, the RFID tag in the single-use device will not be seen by the RFID reader. RFID reader antenna mount, patch or substrate could be, preferably, disposable, but could also be made to be reusable.

Figure 40:
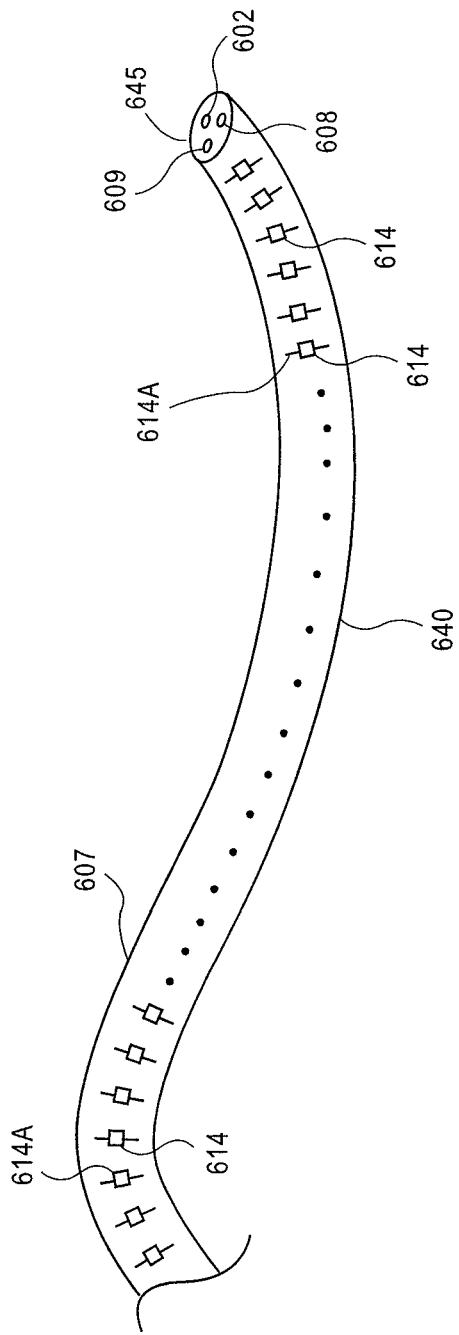
FIG. 40 illustrates a perspective view of a controllable instrument having a plurality of RFID tags along its length.

FIG. 40 illustrates an instrument having an elongate body 640. The elongate body includes a distal end 645. The instrument has working channel 602, a camera 608 and fiber optic bundle 609. In one embodiment, the instrument is an endoscope or a colonoscope. In another embodiment, the instrument is a segmented instrument having a controllable distal tip and a plurality of controllable proximal segments. A plurality of uniquely identified radio frequency identification chips 614 are spaced along the length of the elongate body 640. The chips 614 may be evenly spaced or spaced at different intervals along the length of the elongate body. In one embodiment, more than one radio frequency identification chip is contained within a 2 mm spacing along the length of the elongate body. In another embodiment, one or more radio frequency identification chips are contained within a 1 cm spacing along the length of the elongate body. In one alternative embodiment, each radio frequency identification chip of the plurality of uniquely identified radio frequency identification chips is encoded with position information about the location of the radio frequency identification chip on the elongate body. For example, each chip could be encoded to contain the distance from the chip to the distal end 645. In another example, the RFID chips attached to an instrument are configured to transmit an authentication code.

An antenna 614A is provided for each chip 614. The drawing is not to scale and the antenna 614A may be longer and have a different shape or orientation relative to the elongate body than illustrated. The covering 607 is placed over the elongate body and contains the plurality of radio frequency identification chips 614. An additional optional covering (not shown) may be placed over the covering 607 and chips 614. The chips 614 may also be embedded within a covering 607, between layers of a multilayered laminate structure. Alternatively, the chips 614 and antennas 614A could be mounted on an adhesive backing and secured to the covering 607. Optionally, the chips 614 and antennas 614A on the adhesive backing could be encapsulated in a protective biocompatible covering.

FIG. 41 illustrates an elongate body 640 including a plurality of hinged segments 630 along the length of the elongate body. The embodiment illustrated in FIG. 41 also includes a plurality of uniquely identified radio frequency identification chips 614 spaced along the length of the elongate body. In this embodiment, the radio frequency identification chips are evenly spaced along the length of the elongate body 640 because they are placed on, in or about similarly sized segments 630. Each hinged segment 630 includes segment hinges 626. Adjacent segment hinges 626 join to form a hinged connection 625 between each hinged segment 630. In the illustrated embodiment, each hinged segment 630 contains at least one uniquely identified radio frequency identification chip 614. While illustrated in the same position on each segment 630, the RFID chip 614 may be positioned in a different location on each segment or may be in the same location in similarly oriented segments. Here, similarly oriented segments may be determined by the location of the hinged connection 625 as being on the top/bottom (i.e., 12 o'clock and 6 o'clock positions) or the sides (3 o'clock and 9 o'clock positions). A cross section of an the RFID reader antenna 710 is also illustrated. It may be continuous ring that partially or completely encircles the elongate body 640. As the instrument advances in the direction of the arrow, chips 614 to the left of the antenna 710 will eventually enter the reader field range and become detected while chips to the right of the antenna 710 will eventually leave the reader field range and no longer respond.

FIGS. 42A and 42B illustrate perspective and end views, respectively, of another alternative embodiment of an instrument having a plurality of RFID tags 614. The instrument 600 includes an elongate body 640 and a plurality of uniquely identified radio frequency identification chips 614 spaced along the length of the elongate body. This embodiment also includes a plurality of hinged segments 630 along the length of the elongate body. Two segments 630 and segment hinges 626 are visible. One hinged connection 625 is visible and many more are present under skin or cover 607 but cannot be seen in this view. As in FIG. 41, FIG. 42A illustrates an embodiment where each hinged segment of the plurality of hinged segments contains at least one uniquely identified radio frequency identification chip 614.

FIG. 42A is a perspective, partial section view of an RFID enabled segmented, controllable instrument 600. The hinged segment links 630 form an articulating backbone that articulated along alternating hinged connections 625. The interior of the segment links 630 are hollow and are used to house the other components of the instrument 600. A working channel 602, water channel 603, air supply line 604, camera assembly 608, light fiber bundle 609 and steering tube coils 605 pass through the segment link interior. An organizing spacer 601 (best seen in FIG. 42B) fixes the relative position of the various components. An insertion tube skin 606 and skin 607 encapsulate the instrument 600.

Figure 43A:
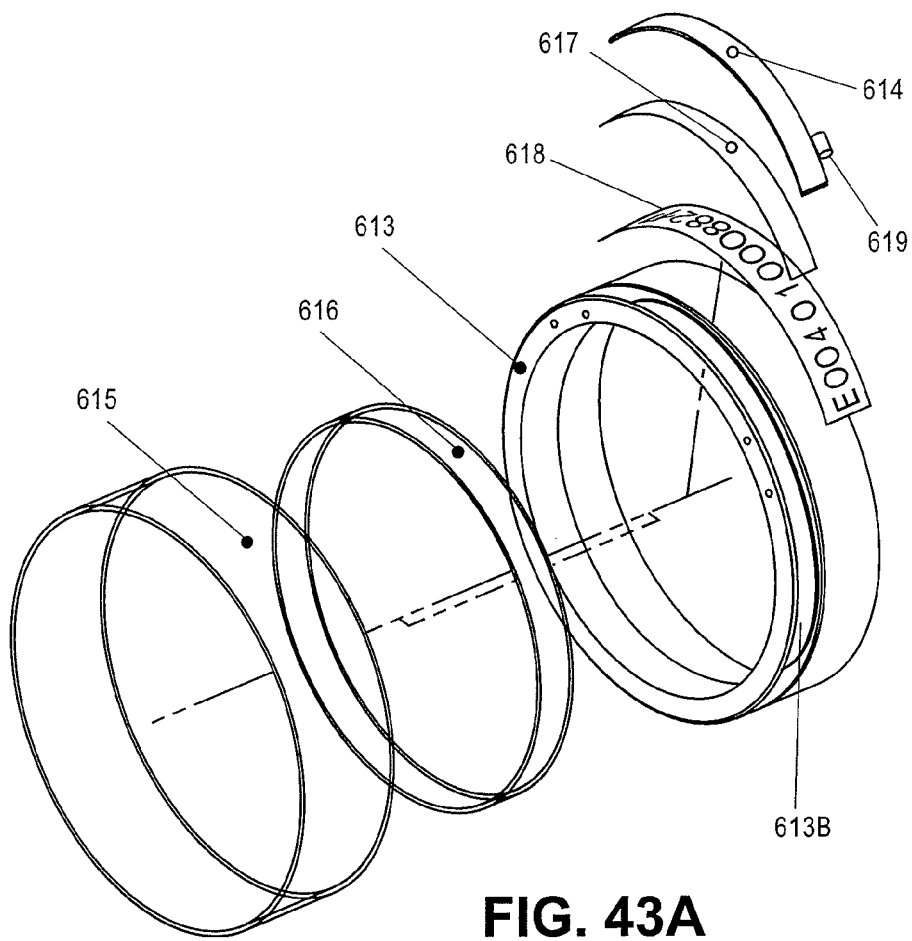
FIGS. 43A and 43B illustrate exploded and assembled views, respectively of the RFID tag used in the embodiments of FIGS. 42A and 42B.
Figure 43B:

An RFID bobbin 613A is best seen in FIGS. 43A and 43B. The bobbin 613 is a circular structure adapted to fit over the hinged segments without interfering with the segment movement. The bobbin 613 includes a recess 613B to stow the antenna RFID tag antenna 616. In this way the chip or a component of the chip wraps at least partially around at least one hinged segment. Depending on the RFID operating frequency, the dimensions of the hinged segments or other design criteria, the RFID antenna may wrap around the bobbin several times. The RFID chip 614 is attached to adhesive tape 617 and connected to antenna 616 with solder 619. An appropriate label 618 may be applied to the bobbin for identification and inventory purposes. The entire bobbin assembly is enclosed using heatshrink 615.

Figure 44:
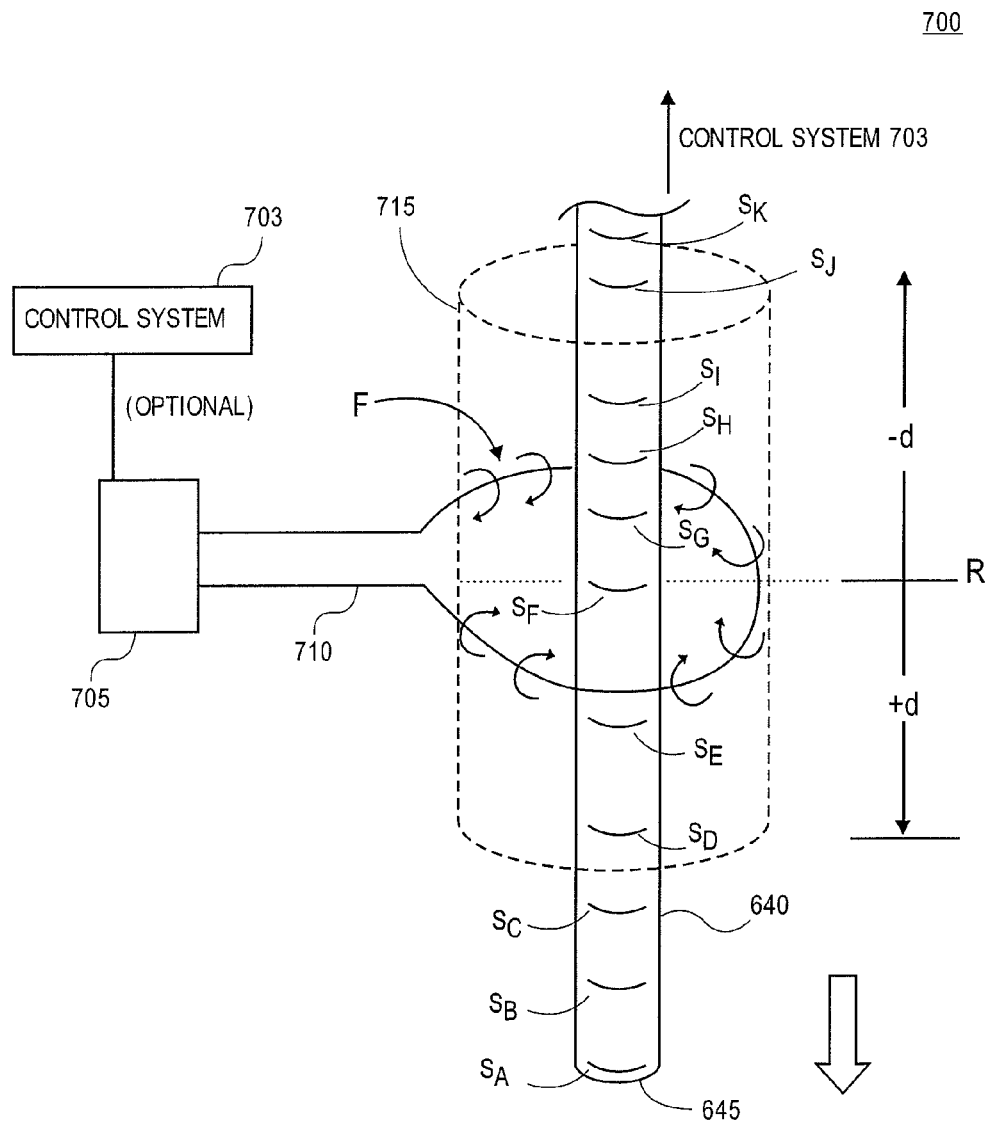
FIG. 44 illustrates an RFID system adapted to determine the position of an RFID equipped instrument.

FIG. 44 illustrates a system for determining the position of an instrument 700. The system 700 includes an instrument 640 and a plurality of uniquely identified radio frequency identification chips (i.e., SA-SK) attached to the instrument. A reader 705 is connected to an antenna 710. The reader 705 is adapted to communicate with each radio frequency identification chip using the antenna 710. As illustrated, the antenna 710 has a circular shape sized to allow the instrument 640 to pass through the circular shape. In one embodiment, the circular shape is a circle. Other shapes, such as oval, oblong or other shapes suited to allow the passage of instruments are also possible.

When the reader 705 provides energy to the antenna 710 a field F (indicated by the arrows looping around antenna 710). The field F is used by the reader 705 to power and communicate with the RFID chips SA-SK. The reader 705 has a reader field range 715 (indicated by the dashed lines) within which the reader can communicate with the RFID chips. If the antenna 710 is used to create a reference position R that approximately divides the reader field range into a +d direction and a −d direction. In this convention, +d indicates that the instrument 640 is moving to an increased depth with relation to the reference position R. Movement by the instrument in the opposition direction, −d, indicates decreasing depth or withdrawal of the instrument with regard to the reference position R. In this way, the position of an individual RFID chip may be determined relative a reference position R or with respect to the reader field range 715. Knowing the position of individual RFID tags can then be used to determine the position of the instrument 640.

Figure 45:
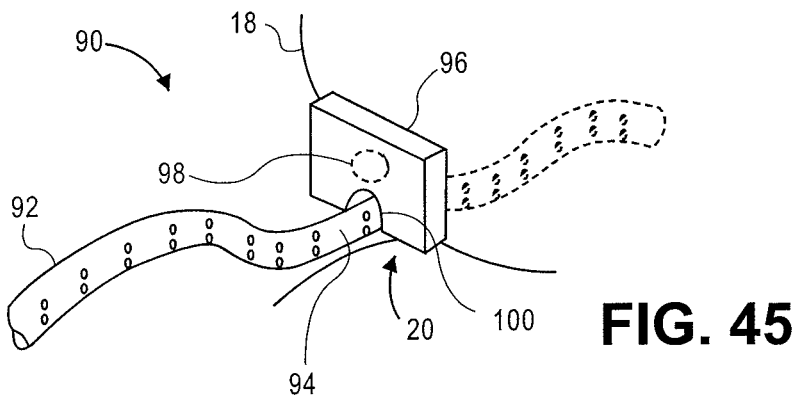
FIGS. 45 and 46 show one variation in using an RFID equipped controllable instrument used in conjunction with external sensing device or datum.
Figure 46:
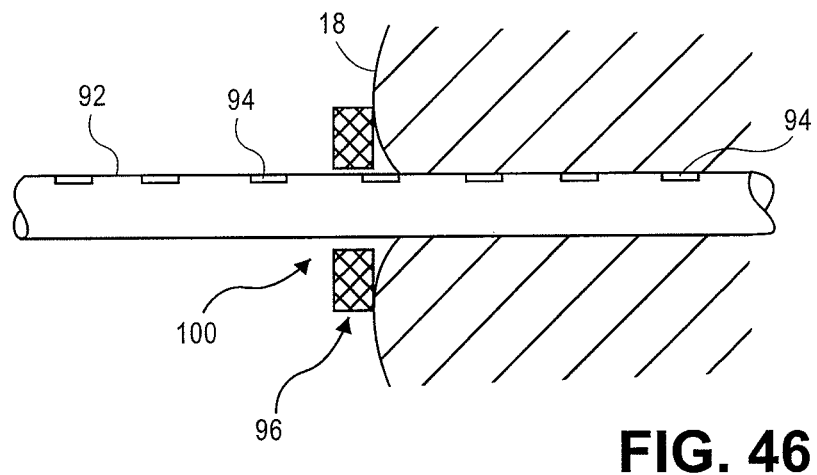

FIGS. 45 and 46 show one variation in using an endoscope assembly 90 in conjunction with external sensing device or datum 96 configured similar to the substrate 740. Datum 96 may be positioned externally of patient 18 adjacent to an opening into a body cavity, e.g., anus 20 for colonoscopic procedures. Datum 96 may include the RFID reader 98 located next to opening 100, which may be used as a guide for passage of endoscope 92. With proper placement next to the body, the opening 100 in the datum 96 may be used to guide the endoscope 92 there through into anus 20. Endoscope 92 may be configured to have a number of RFID tags 94 located along the body of endoscope 92. These tags 94 may be positioned at regular intervals along endoscope 92. The spacing between the RFID tags 94 may vary and may also depend upon the desired degree of accuracy in endoscope position determination. RFID tags 94 may be positioned closely to one another to provide for a higher resolution reading, while RFID tags 94 spaced farther apart from one another may provide for a lower resolution determination. Moreover, RFID tags 94 may be positioned at uniform distances from one another, or alternatively they may be spaced apart as irregular intervals, depending upon the desired results. Moreover, RFID tags 94 may be positioned along the entire length of endoscope 92 or only along a portion of it, depending upon the desired results. As shown in FIG. 46, as endoscope 92 is passed through datum 96 via opening 100 and into anus 20, RFID reader 98 located within datum 96 may sense each of the RFID tags 94 as they pass through opening 100. Accordingly, the direction and insertion depth of endoscope 92 may be recorded and/or maintained for real-time positional information of the endoscope 92.

Figure 47:
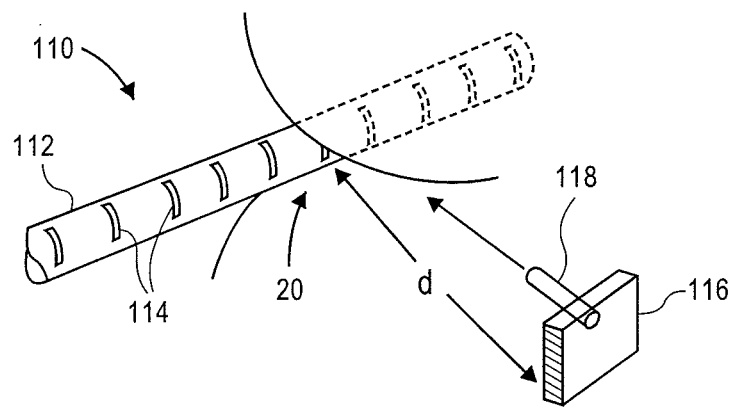
FIG. 47 illustrates another variation of an RFID equipped controllable instrument used in conjunction with a datum located a distance from the instrument.

FIG. 47 shows another example in endoscope assembly 110 in which endoscope 112 may have a number of RFID tags 114 located along the body of the endoscope 112. As endoscope 112 is advanced or withdrawn from anus 20, datum 116 (includes an RFID reader connected to an antenna 118), which may be mounted externally of the patient and at a distance from endoscope 112, may have a receiver or reader 118 configured in any of the variations described above. For instance, receiver or reader 118 may be adapted to function as a RFID reader as in any of the other variations described above. The reader may be placed a distance d from the opening 20 and at various orientations relative to the endoscope based upon several factors such as the operating frequency and interference caused by surrounding structures. The distance d and orientation are selected so that the endoscope 92 remains within the reader field range. As illustrated, the reader 116 is only reading those tags 114 adjacent to anus 20 and outside of the body. The RFID tags indicated in phantom are no longer read by the reader. The reader may be adapted to communicate with the control system 703 used to control the endoscope. In addition, the output from the reader 116 may be used to map RFID tag positions on the endoscope 112 and thus, the length of insertion of the endoscope 112 into a natural or surgically created body opening.

FIGS. 48, 49 and 50 illustrate alternative embodiments of a flexible substrate that is used to support the reader antenna 710 and the RFID chip 614U that is separate from the RFID chips 614 attached to the instrument. FIG. 48 illustrates a stingray shaped substrate 740.1 having an aperture 773 sized to allow passage of an instrument. The antenna 710 is positioned about the aperture 773 and is connected to the reader (not shown) via wires 711 and suitable connector 712. The RFID chip 614U is placed on the substrate 740.1 and within the reader field range so that it is always detected by antenna 710. FIG. 740.2 also contains an RFID chip 614U (present but not shown in FIGS. 48-50), an antenna 710 and an aperture 773. The substrate 740.2 differs from substrate 740.1 by slots 793 that are used to form flaps 791. Reinforcement elements or battens 788 are also provided in the substrate 740.2 for added support. The substrate 740.3 differs from the other substrates by different sized slots 793 that are used to form various flaps 791.

Figure 51:
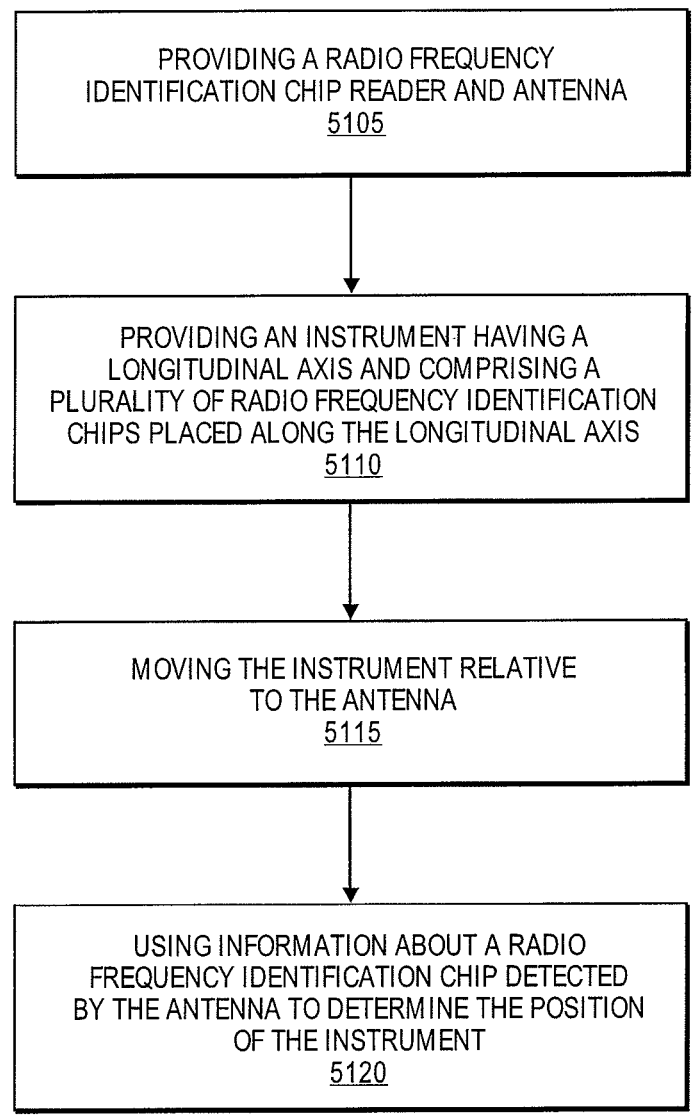
FIG. 51 illustrates a flow chart of one embodiment of a method for using RFID techniques to determine the position of an instrument.

FIG. 51 illustrates flow chart 5100 for an embodiment of a method for determining the position of an instrument using radio frequency identification chips. First, there is the step of providing a radio frequency identification chip reader and antenna (step 5105). Next, there is the step of providing an instrument having a longitudinal axis and comprising a plurality of radio frequency identification chips placed along the longitudinal axis (step 5110). Next, the instrument is moved relative to the antenna (step 5115). Finally, the step of using information about a radio frequency identification chip detected by the antenna to determine the position of the instrument (step 5120). An additional and optional step would be providing information about the position of the instrument relative to the antenna to a system used to control the instrument. One exemplary control system includes an electronic motion controller and actuators to facilitate the articulation of a steerable, articulating instrument having RFID features and functionalities as described herein. Additional details of the control system and controllable segmented instruments may be found in: U.S. Pat. No. 6,468,203; U.S. patent application Ser. No. 09/969,927 filed Oct. 2, 2001; U.S. patent application Ser. No. 10/229,577 filed Aug. 27, 2002; U.S. patent application Ser. No. 10/087,100 filed Mar. 1, 2002; and U.S. patent application Ser. No. 10/139,289 filed May 2, 2002, each of which is incorporated herein by reference in its entirety.

In one alternative embodiment, the moving step 5115 includes passing the instrument through a hoop formed by the antenna. The step of providing a radio frequency identification chip reader and antenna may also include placing the antenna adjacent an opening in the body of a mammal. The opening in the body of a mammal may be a natural opening or an opening that is created surgically.

In another alternative embodiment, the using step 5120 includes using information about a radio frequency identification chip detected by the antenna to determine the position of the instrument relative to the antenna. Additionally or alternatively, the information about a radio frequency identification chip may include an indication that the radio frequency identification chip has entered the opening in the body of the mammal. One indication may be that the reader no longer detects the radio frequency identification chip. The reader would not be able to detect a tag if the RF energy is being absorbed by the surrounding tissue as in the case of using RFID systems in some UHF and microwave frequencies.

The applications of the devices and methods discussed above are not limited to regions of the body but may include any number of further treatment applications. Other treatment sites may include other areas or regions of the body. Additionally, the present invention may be used in other environments such as exploratory procedures on piping systems, ducts, etc. Modification of the above-described assemblies and methods for carrying out the invention, and variations of aspects of the invention that are obvious to those of skill in the art are intended to be within the scope of the claims.

What is claimed is:

1. An instrument, comprising:
an elongate body, wherein at least a portion of the elongate body is flexible so as to be placed into a curved shape;
a plurality of radio frequency identification (RFID) chips spaced along a length of the elongate body, wherein each RFID chip of the plurality of RFID chips is encoded with unique position information that specifies the location of the RFID chip relative to a distal end of the elongate body; and
an insertion depth determining system in signal communication with each of the plurality of RFID chips to receive the unique position information encoded in each RFID chip, the insertion depth determining system configured to output a depth of insertion of the elongate body based on the unique position information received from a respective RFID chip.

2. The instrument of claim 1, further comprising:
a covering over the elongate body that contains the plurality of RFID chips.

3. The instrument of claim 1, further comprising:
a plurality of hinged segments along the length of the elongate body wherein each hinged segment of the plurality of hinged segments contains at least one RFID chip of the plurality of RFID chips.

4. The instrument of claim 3, wherein an antenna of at least one RFID chip of the plurality of RFID chips wraps at least partially around at least one hinged segment of the plurality of hinged segments.

5. The instrument of claim 1, wherein the plurality of RFID chips are evenly spaced along the length of the elongate body.

6. The instrument of claim 1, wherein the plurality of RFID chips are spaced at different intervals along the length of the elongate body.

7. The instrument of claim 1, wherein the plurality of RFID chips operate at a frequency of about 13.56 MHz.

8. The instrument of claim 1, wherein the plurality of RFID chips operate at a frequency of about 2.45 GHz.

9. The instrument of claim 1, wherein one or more RFID chips are contained within a 2 mm spacing along the length of the elongate body.

10. The instrument of claim 1, wherein one or more RFID chips are contained within a 1 cm spacing along the length of the elongate body.

11. The instrument of claim 1, wherein the depth of insertion of the elongate body is determined with reference to an anatomical landmark.

12. The instrument of claim 1, wherein the position information further comprises a position of a respective chip about a perimeter of the elongate body.

13. The instrument of claim 1, wherein the instrument is a medical instrument.

14. The instrument of claim 13, wherein the medical instrument is an endoscope.

15. The instrument of claim 1, wherein the instrument is a steerable, articulating instrument.

16. A system for determining the position of an instrument, comprising:
- an instrument;
- a plurality of uniquely identified radio frequency identification (RFID) chips attached to the instrument;
- a reader connected to an antenna and adapted to communicate with each RFID chip in the plurality of uniquely identified RFID chips using the antenna;
- a separate uniquely identified RFID chip distinct from the plurality of RFID chips attached to the instrument, the separate uniquely identified RFID chip positioned within the detectable field of the antenna so as to always be detected by the reader without regard to the position of the instrument; and
- a flexible substrate on which the separate uniquely identified RFID chip and the antenna are mounted.

17. The system for determining the position of an instrument of claim 16, wherein at least one RFID chip in the plurality of RFID chips attached to the instrument is configured to transmit an authentication code.

18. The system for determining the position of an instrument of claim 16, wherein the antenna and the RFID chips are configured to operate at a frequency of about 13.56 MHz.

19. The system for determining the position of an instrument of claim 16, wherein the antenna and the RFID chip are configured to operate at a frequency of about 2.45 GHz.

20. The system for determining the position of an instrument of claim 16, wherein the instrument is an endoscope or a colonoscope.

21. The system for determining the position of an instrument of claim 16, wherein the instrument is a segmented instrument having a controllable distal tip and a plurality of controllable proximal segments.

22. The system for determining the position of an instrument of claim 16, wherein the antenna is straight.

23. The system for determining the position of an instrument of claim 16, wherein the antenna has a circular shape sized to allow the instrument to pass through the circular shape.

24. The system for determining the position of an instrument of claim 23, wherein the circular shape is a circle.

25. The system for determining the position of an instrument of claim 16, the flexible substrate further comprising an aperture sized to allow the passage of the instrument.

26. The system for determining the position of an instrument according to claim 16, further comprising an insertion depth determining system configured to determine the depth of insertion of the instrument with reference to an anatomical landmark based on information recorded by the plurality of uniquely identified RFID chips.

27. A method of determining a depth of insertion of an endoscopic instrument using radio frequency identification (RFID) chips, comprising:
- providing a RFID chip reader and antenna;
- providing an endoscopic instrument having a longitudinal axis and comprising a plurality of RFID chips placed along the longitudinal axis of the endoscopic instrument, wherein each RFID chip of the plurality of RFID chips is encoded with unique position information that specifies the location of the RFID chip relative to a distal end of the longitudinal axis;
- moving the endoscopic instrument relative to the antenna to detect the unique position information from a respective RFID chip; and
- based on the detected unique position information, outputting the depth of insertion of the endoscopic instrument.

28. The method of determining a depth of insertion of an endoscopic instrument of claim 27, wherein the moving comprises passing the endoscopic instrument through a hoop formed by the antenna.

29. The method of determining a depth of insertion of an endoscopic instrument of claim 27, further comprising:
- providing information about the depth of insertion of the endoscopic instrument relative to the antenna to a system used to control the instrument.

30. The method of determining a depth of insertion of an endoscopic instrument of claim 27, wherein the providing a RFID chip reader and antenna comprises placing the antenna adjacent an opening in the body of a mammal.

31. The method of determining a depth of insertion of an endoscopic instrument of claim 30, wherein the opening in the body of a mammal is a natural opening.

32. The method of determining a depth of insertion of an endoscopic instrument of claim 30, wherein the opening in the body of a mammal is created surgically.

* * * * *